United States Patent
Kim et al.

(10) Patent No.: US 11,926,706 B2
(45) Date of Patent: Mar. 12, 2024

(54) DIAMINE COMPOUND, AND POLYIMIDE PRECURSOR AND POLYIMIDE FILM USING SAME

(71) Applicant: LG CHEM, LTD., Seoul (KR)

(72) Inventors: Minju Kim, Daejeon (KR); Jinyoung Park, Daejeon (KR); Hoyong Lee, Daejeon (KR); Cheol Jun Song, Daejeon (KR)

(73) Assignee: LG CHEM, LTD., Seoul (KR)

( * ) Notice: Subject to any disclaimer, the term of this patent is extended or adjusted under 35 U.S.C. 154(b) by 444 days.

(21) Appl. No.: 17/276,526

(22) PCT Filed: Jan. 22, 2020

(86) PCT No.: PCT/KR2020/001137
§ 371 (c)(1),
(2) Date: Mar. 16, 2021

(87) PCT Pub. No.: WO2020/153771
PCT Pub. Date: Jul. 30, 2020

(65) Prior Publication Data
US 2022/0041809 A1     Feb. 10, 2022

(30) Foreign Application Priority Data

Jan. 25, 2019   (KR) .......................... 10-2019-0009547
Jan. 15, 2020   (KR) .......................... 10-2020-0005487

(51) Int. Cl.
*C08G 73/10* (2006.01)
*C07D 209/48* (2006.01)
*C08J 5/18* (2006.01)

(52) U.S. Cl.
CPC ....... *C08G 73/1067* (2013.01); *C07D 209/48* (2013.01); *C08G 73/1032* (2013.01); *C08G 73/1064* (2013.01); *C08J 5/18* (2013.01); *C08J 2379/08* (2013.01)

(58) Field of Classification Search
None
See application file for complete search history.

(56) References Cited

U.S. PATENT DOCUMENTS

| | | | |
|---|---|---|---|
| 4,410,664 A * | 10/1983 | Lee | C08G 73/1067 528/93 |
| 4,668,757 A | 5/1987 | Nichols | |
| 5,212,277 A | 5/1993 | Lee et al. | |
| 5,235,005 A | 8/1993 | Shiobara et al. | |
| 2004/0010062 A1 | 1/2004 | Ahn et al. | |
| 2008/0044639 A1* | 2/2008 | Chan | C08J 5/18 528/335 |
| 2012/0095147 A1 | 4/2012 | Huang et al. | |

FOREIGN PATENT DOCUMENTS

| | | | |
|---|---|---|---|
| CN | 1837260 A * | 9/2006 | |
| CN | 102432878 A | 5/2012 | |
| CN | 102453326 A | 5/2012 | |
| CN | 104927072 A * | 9/2015 | |
| JP | H08-283436 A | 10/1996 | |
| JP | 2005-503478 A | 2/2005 | |
| JP | 2016-023285 A | 2/2016 | |
| KR | 10-1993-0005151 B1 | 6/1993 | |
| WO | 2016-013403 A1 | 1/2016 | |

OTHER PUBLICATIONS

Office Action issued for Japanese Patent Application No. 2021-509194 dated Jan. 25, 2022, with English translation, 4 pages.
Han, et al., "Synthesis and characterization of new polyimides containing ethynylene linkages", European Polymer Journal, 2007, vol. 43, No. 4, 1541-1548.
Choi, et al., "Synthesis and Properties of New Thermally Stable, Cross-linkable Poly(imide-enaminonitrile)s", Korea Polymer Journal, 1997, vol. 5, No. 1, pp. 33-38.
International Search Repose issued for International Application No. PCT/KR2020/001137 dated May 22, 2020, 4 pages.

* cited by examiner

*Primary Examiner* — Tae H Yoon
(74) *Attorney, Agent, or Firm* — ROTHWELL, FIGG, ERNST & MANBECK, P.C.

(57) ABSTRACT

Disclosed is a novel diamine compound in which an imide ring is directly bonded to a (hetero)aryl ring in a molecule, and a polyimide film prepared by polymerizing the novel diamine compound exhibits improved thermal properties and storage stability.

20 Claims, No Drawings

DIAMINE COMPOUND, AND POLYIMIDE PRECURSOR AND POLYIMIDE FILM USING SAME

This application is a 35 U.S.C. 371 National Phase Entry Application from PCT/KR2020/001137, filed on Jan. 22, 2020 and designating the United States, which claims the benefit of priorities to Korean Patent Application Nos. 10-2019-0009547, filed on Jan. 25, 2019 and 10-2020-0005487, filed on Jan. 15, 2020, the entire disclosures of which are incorporated herein by reference.

BACKGROUND OF THE INVENTION

1. Field of the Invention

The present invention relates to a novel diamine compound, a polyimide precursor and a polyimide film by using same.

In recent years, weight reduction and miniaturization of products have been emphasized in the field of display. A currently used glass substrate is heavy and brittle and is difficult to apply to a continuous process. Accordingly, researches are actively carried out for applying a plastic substrate having advantages of lightness, flexibility, and applicability to continuous process and substitutable for a glass substrate, to a cell phone, a notebook and a PDA (personal digital assistant).

In particular, a polyimide has an advantage that it is easy to be synthesized, can be formed into a thin film and does not require a crosslinking group for curing. Recently, due to weight reduction and precision of electronic products, a polyimide is widely used as a material for integration in semiconductor such as liquid crystal display (LCD), plasma display panel (PDP), etc. Many studies have progressed for polyimide to apply to a flexible plastic display board having light and flexible characteristics.

A polyimide film, which is produced by film-forming the polyimide, is generally prepared by solution polymerization of aromatic dianhydride and aromatic diamine or aromatic diisocyanate to prepare a solution of polyamic acid derivative, coating the solution on a silicon wafer or a glass, and curing by heat treatment.

A flexible device involving a high temperature process requires heat resistance at high temperatures. In particular, an organic light emitting diode (OLED) device manufactured using a low temperature polysilicon (LTPS) process may have a process temperature close to 500° C. However, at this temperature, thermal decomposition by hydrolysis tends to occur even with the polyimide having excellent heat resistance. Therefore, in order to manufacture a flexible device, it is necessary to secure excellent chemical resistance and storage stability so that thermal decomposition by hydrolysis during the high temperature process does not occur.

BRIEF SUMMARY OF THE INVENTION

The present invention provides a novel diamine compound for producing a polyimide with improved heat resistance, storage stability, etc.

The present invention also provides a polyimide precursor prepared by using the novel diamine compound.

The present invention further provides a polyimide film prepared by using the polyimide precursor and a flexible device including the polyimide film.

The present invention provides a diamine compound represented by the following formula 1:

[Formula 1]

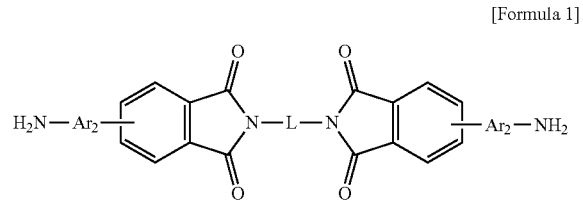

In the formula 1,
L is a linker selected from

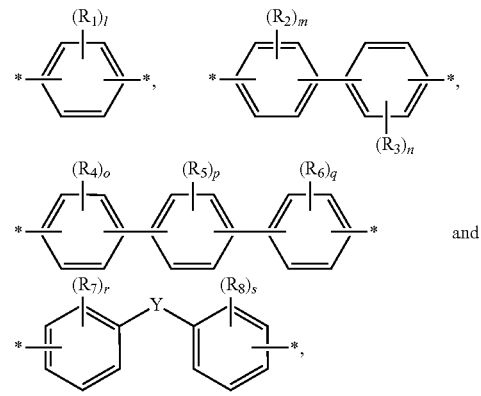

$Ar_1$ and $Ar_2$ are each independently a divalent organic group selected from

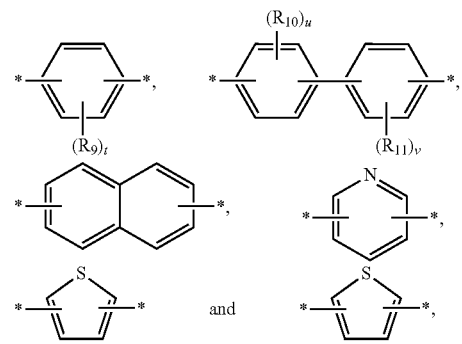

$R_1$ to $R_{11}$ are each independently hydrogen, deuterium, a halogen atom, a cyano group, a hydroxy group, a substituted or unsubstituted alkyl group having 1 to 30 carbon atoms, a substituted or unsubstituted haloalkyl group having 1 to 30 carbon atoms, a substituted or unsubstituted alkysilyl group having 1 to 30 carbon atoms, a substituted or unsubstituted arylsilyl group having 6 to 30 carbon atoms, a substituted or unsubstituted alkylamino group having 1 to 30 carbon atoms, a substituted or unsubstituted arylamino group having 6 to 30 carbon atoms, a substituted or unsubstituted alkoxy group having 1 to 30 carbon atoms, a substituted or unsubstituted alkylthio group having 1 to 30 carbon atoms, a substituted or unsubstituted arylthiol group having 6 to 30 carbon atoms, a substituted or unsubstituted aryl group having 6 to 30 carbon atoms, a substituted or unsubstituted aralkyl group having 6 to 30 carbon atoms, a substituted or unsubstituted aryloxy group having 6 to 30 carbon atoms, a —COOH group, a substituted or unsubstituted cycloalkyl group having 3 to 30 carbon atoms, an amide group, a substituted or unsubstituted cycloalkyloxy group having 3 to 30 carbon atoms, a substituted or unsubstituted cycloalkylthio group having 1 to 30 carbon atoms, an ester group, —CD$_3$, an azide group, a nitro group, or a substituted or unsubstituted (3-30 membered) heteroaryl group comprising at least one selected from B, N, O, S, P (=O), Si and P, Y is selected from

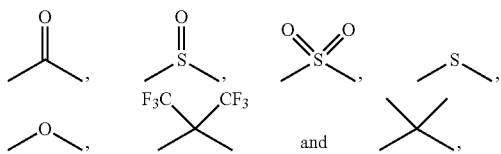

l, m, n, o, p, q, r, s, t, u and v are each an integer of 0 to 4, and when l, m, n, o, p, q, r, s, t, u and v are integers of 2 to 4, each of $R_1$ to $R_{11}$ may be the same or different.

The diamine compound of the present invention is a novel compound comprising a moiety having an imide ring directly bonded to a (hetero) aryl ring in a molecule, and the polyimide precursor containing it as a polymerization component can provide a polyimide film having improved thermal and mechanical properties after curing.

DETAILED DESCRIPTION OF THE INVENTION

Since various modifications and variations can be made in the present invention, particular embodiments will be described in detail in the detailed description. It should be understood, however, that the invention is not intended to be limited to the particular embodiments, but includes all modifications, equivalents, and alternatives falling within the spirit and scope of the invention. In the following description of the present invention, detailed description of known functions will be omitted if it is determined that it may obscure the gist of the present invention.

Aromatic polyimides are widely used in high-tech industries such as microelectronics, aerospace, insulating materials and refractory materials due to their excellent overall properties such as thermal oxidation stability, and high mechanical strength. However, aromatic polyimides having high absorbance in ultraviolet-visible region exhibit strong coloration from pale yellow to dark brown. It limits their wide application in the optoelectronics area, where transparency and colorless properties are basic requirements. The reason for the coloration in the aromatic polyimide is that intramolecular charge transfer complexes (CT-complexes) are formed between an alternating electron donor (dianhydride) and an electron acceptor (diamine) in the polymer main chain and between internal molecules.

To solve this problem, methods for introducing specific functional groups, bulky pendant groups, fluorinated functional groups, etc. into the polymer main chain, or introducing —S—, —O—, —CH$_2$—, etc. have been attempted to develop an optically transparent polyimide film having a high glass transition temperature (Tg).

The inventors of the present invention have made extensive studies to solve the problems of the prior art based on the prior art, and found that a novel diamine compound having a specific structure provides excellent thermal and mechanical properties, and completed the present invention.

Accordingly, the present invention provides a diamine compound of the following formula 1.

[Formula 1]

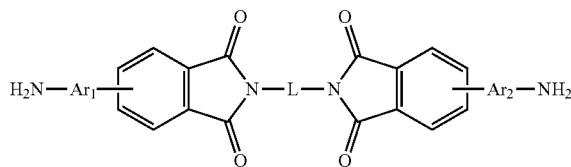

In the formula 1,
L is a linker selected from

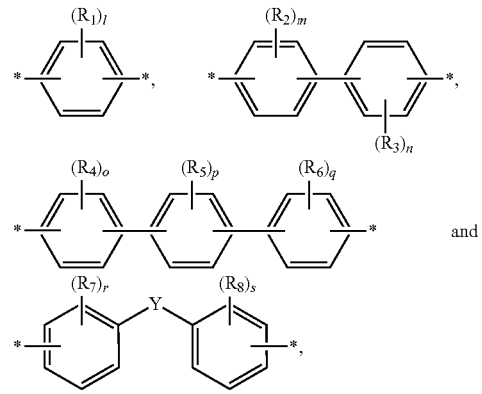

$Ar_1$ and $Ar_2$ are each independently a divalent organic group selected from

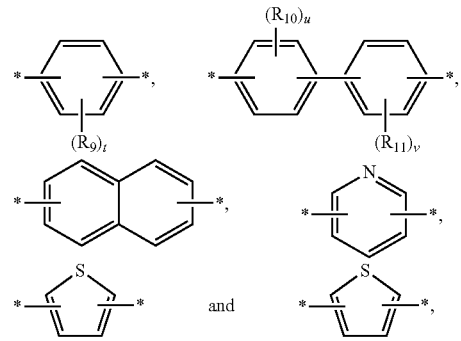

$R_1$ to $R_{11}$ are each independently hydrogen, deuterium, a halogen atom, a cyano group, a hydroxy group, a substituted or unsubstituted alkyl group having 1 to 30 carbon atoms, a substituted or unsubstituted haloalkyl group having 1 to 30 carbon atoms, a substituted or unsubstituted alkysilyl group having 1 to 30 carbon atoms, a substituted or unsubstituted arylsilyl group having 6 to 30 carbon atoms, a substituted or unsubstituted alkylamino group having 1 to 30 carbon atoms, a substituted or unsubstituted arylamino group having 6 to 30 carbon atoms, a substituted or unsubstituted alkoxy group having 1 to 30 carbon atoms, a substituted or unsubstituted alkylthio group having 1 to 30 carbon atoms, a substituted or unsubstituted arylthiol group having 6 to 30 carbon atoms, a substituted or unsubstituted aryl group having 6 to 30 carbon atoms, a substituted or unsubstituted aralkyl group having 6 to 30 carbon atoms, a substituted or unsubstituted aryloxy group having 6 to 30 carbon atoms, a —COOH group, a substituted or unsubstituted cycloalkyl group having 3 to 30 carbon atoms, an amide group, a substituted or unsubstituted cycloalkyloxy group having 3 to 30 carbon atoms, a substituted or unsubstituted cycloalkylthio group having 1 to 30 carbon atoms, an ester group, —CD$_3$, an azide group, a nitro group, or a substituted or unsubstituted (3-30 membered) heteroaryl group comprising at least one selected from B, N, O, S, P (=O), Si and P, Y is selected from

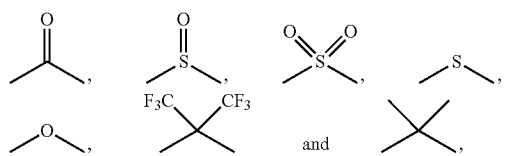

l, m, n, o, p, q, r, s, t, u and v are each an integer of 0 to 4, and when l, m, n, o, p, q, r, s, t, u and v are integers of 2 to 4, each of $R_1$ to $R_{11}$ may be the same or different.

The term "substituted" in the description of "substituted or unsubstituted" as described herein means that a hydrogen atom in any functional group is replaced by another atom or another functional group, i.e., another substituent.

In the formula 1, substituents of the substituted alkyl group, the substituted haloalkyl group, the substituted alkylsilyl group, the substituted arylsilyl group, the substituted alkylamino group, the substituted arylamino group, the substituted alkoxy group, the substituted alkylthio group, the substituted arylthio group, the substituted aryl group, the substituted aralkyl group, the substituted aryloxy group, the substituted cycloalkyl group, the substituted cycloalkyloxy group, the substituted cycloalkylthio group and the substituted heteroaryl group are each independently at least one selected from the group consisting of deuterium, a halogen atom, a cyano group, an amino group, a carboxyl group, a nitro group, a hydroxy group, an alkyl group having 1 to 30 carbon atoms, an alkenyl group having 2 to 30 carbon atoms, an alkynyl group having 2 to 30 carbon atoms, an alkoxy group having 1 to 30 carbon atoms, an alkylthio group having 1 to 30 carbon atoms, an arylthio group having 6 to 30 carbon atoms, an aryl group having 6 to 30 carbon atoms, a cycloalkyl groups having 3 to 30 carbon atoms, a cycloalkenyl group having 3 to 30 carbon atoms, an aryloxy group having 6 to 30 carbon atoms, an alkylsilyl group having 1 to 30 carbon atoms, an arylsilyl group having 6 to 30 carbon atoms, an alkylamino group having 1 to 30 carbon atoms, an arylamino group having 6 to 30 carbon atoms, an alkylcarbonyl group having 1 to 30 carbon atoms, an alkoxycarbonyl group having 1 to 30 carbon atoms, an arylcarbonyl group having 6 to 30 carbon atoms, an alkylboronyl group having 1 to 30 carbon atoms, an arylboronyl group having 6 to 30 carbon atoms.

As used herein, "alkyl having 1 to 30 carbon atoms" means straight-chain or branched alkyl having 1 to 30 carbon atoms, preferably 1 to 20 carbon atoms, and more preferably 1 to 10 carbon atoms. Specific examples of the alkyl include methyl, ethyl, n-propyl, isopropyl, n-butyl, isobutyl, tert-butyl, and the like.

As used herein, "alkenyl having 2 to 30 carbon atoms" means straight-chain or branched alkenyl having 2 to 30 carbon atoms, preferably 2 to 20 carbon atoms, and more preferably 2 to 10 carbon atoms. Specific examples of the alkenyl include vinyl, 1-propenyl, 2-propenyl, 1-butenyl, 2-butenyl, 3-butenyl, 2-methylbut-2-enyl, and the like.

As used herein, "alkynyl having 2 to 30 carbon atoms" means straight-chain or branched alkynyl having 2 to 30 carbon atoms, preferably 2 to 20 carbon atoms, and more preferably 2 to 10 carbon atoms. Examples of the alkynyl include ethynyl, 1-propynyl, 2-propynyl, 1-butynyl, 2-butynyl, 3-butynyl, 1-methylpent-2-ynyl, and the like.

As used herein, "alkoxy having 1 to 30 carbon atoms" means straight-chain or branched alkoxy having 1 to 30 carbon atoms, preferably 1 to 20 carbon atoms, and more preferably 1 to 10 carbon atoms. Examples of the alkoxy include methoxy, ethoxy, propoxy, isopropoxy, 1-ethylpropoxy, and the like.

As used herein, "cycloalkyl having 3 to 30 carbon atoms" means a monocyclic or polycyclic hydrocarbon having 3 to 30 carbon atoms, preferably 3 to 20 carbon atoms, and more preferably 3 to 7 carbon atoms. Examples of the cycloalkyl include cyclopropyl, cyclobutyl, cyclopentyl, cyclohexyl, and the like.

As used herein, "aryl(en) having 6 to 30 carbon atoms" means a monocyclic or fused cyclic radical derived from an aromatic hydrocarbon having 6 to 30 carbon atoms, preferably having 6 to 20 ring skeleton carbon atoms, and more preferably 6 to 15 ring skeleton carbon atoms. Examples of the aryl include phenyl, biphenyl, terphenyl, naphthyl, fluorenyl, phenanthrenyl, anthracenyl, indenyl, triphenylenyl, pyrenyl, tetracenyl, perylenyl, chrysenyl, naphthacenyl, fluoranthenyl, and the like.

As used herein, "(3-30 membered) heteroaryl(en)" means that an aryl group having 3 to 30 ring skeleton atoms and containing one or more heteroatom selected from the group consisting of B, N, O, S, P(=O), Si and P. The aryl group preferably has 3 to 20 ring skeleton carbon atoms, and more preferably 3 to 15 ring skeleton carbon atoms and preferably contains 1 to 4 heteroatoms. The heteroaryl group may be a monocyclic group or fused ring condensed with one or more benzene rings and may be partially saturated. In addition, the heteroaryl as used herein includes one or more heteroaryl groups or aryl groups connected to a heteroaryl group by a single bond. Examples of the heteroaryl include monocyclic heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl and pyridazinyl, and fused cyclic heteroaryl such as benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindoly, indolyl, indazolyl, benzothiadiazolyl, quinolyl, isoquinolyl, cynolinyl, quinazolinyl, quinoxalinyl, carbazolyl, phenoxazinyl, phenanthridinyl and benzodioxolyl.

As used herein "halogen" includes F, Cl, Br and I atoms.

According to an embodiment, in the compound of formula 1,

L is a linker selected from

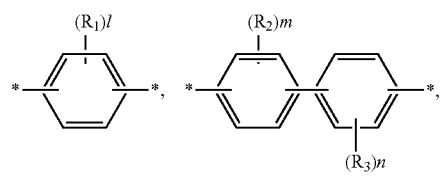

-continued

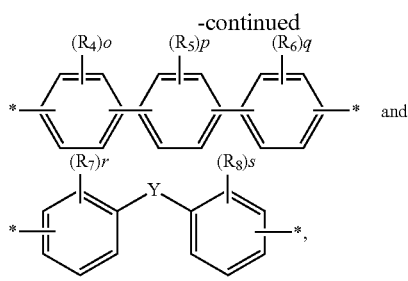

Ar₁ and Ar₂ are each independently

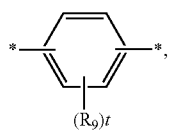

R₁ to R₈ are each independently a halogen atom, or an alkyl group having 1 to 6 carbon atoms or an alkoxy group having 1 to 6 carbon atoms, which are unsubstituted or substituted with a halogen atom, R₉ is a halogen atom, or a (C1-C₆) alkyl group which is unsubstituted or substituted with a halogen atom, Y is selected from

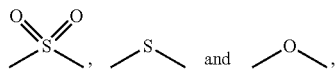

and l, m, n, o, p, q, r, s and t are each an integer of 0 to 2.

According to an embodiment, in the compound of formula 1, L is phenyl which is unsubstituted or substituted with one or more substituents selected from the group consisting of trifluoromethyl, methyl, chlorine (Cl) and methoxy; biphenyl which is unsubstituted or substituted with one or more substituents selected from the group consisting of methyl, trifluoromethyl and chlorine; terphenyl which is unsubstituted or substituted with trifluoromethyl; bis(trifluoromethylphenyl)sulfone, bis(methylphenyl) sulfone, {(trifluoromethylphenyl)sulfonyl}phenyl, diphenylsulfide, bis(methylphenyl)sulfide, bis(trifluoromethylphenyl)sulfide or diphenyl ether, Ar₁ and Ar₂ are each independently phenyl which is unsubstituted or substituted with one or more substituents selected from the group consisting of methyl, trifluoromethyl and chlorine, l is an integer of 0 to 2, m, n, o, p, q, r, s and t are each an integer of 0 or 1.

According to an embodiment, the diamine compound of formula 1 may be selected from compounds of the following structural formulas, but is not limited thereto:

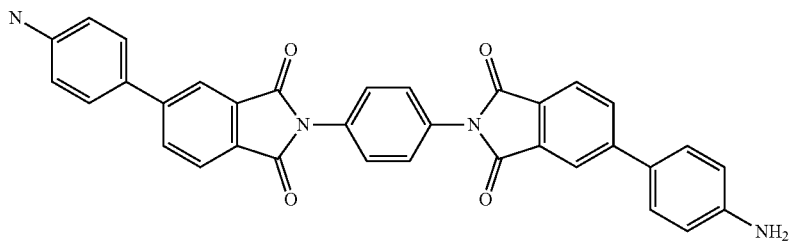

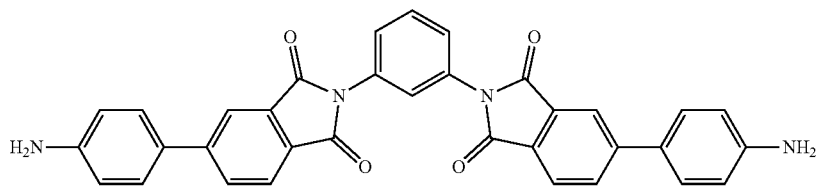

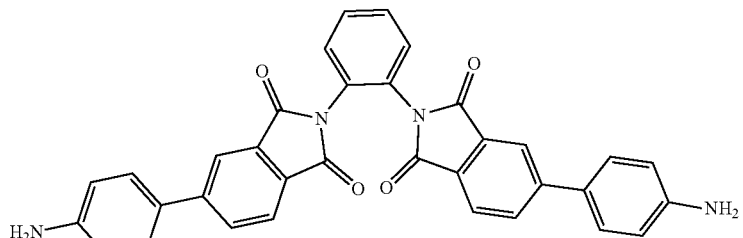

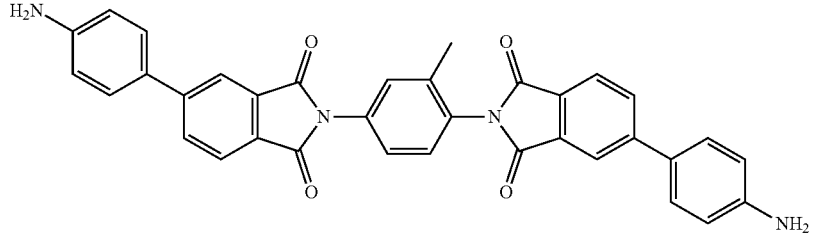

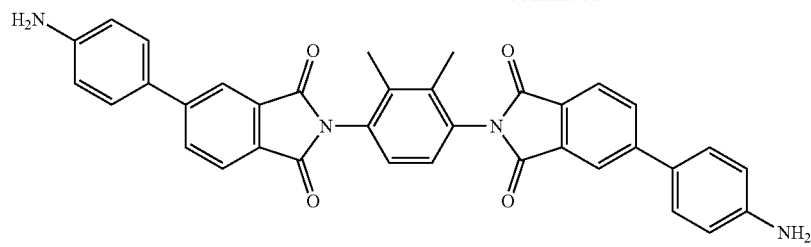
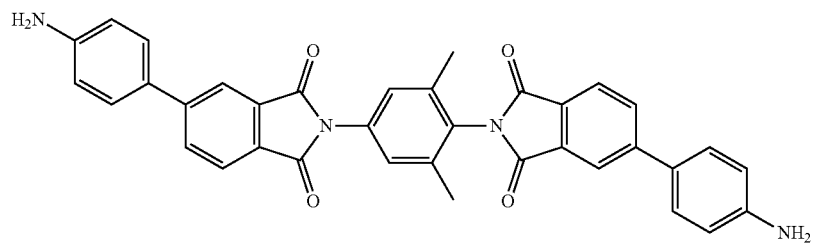
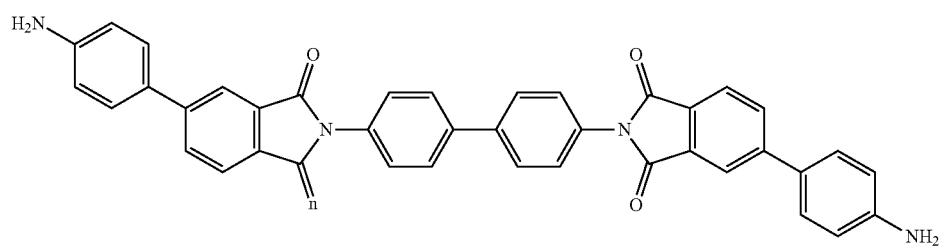
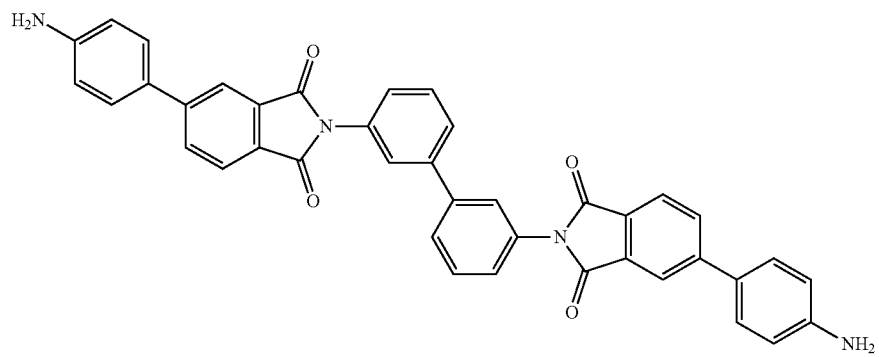
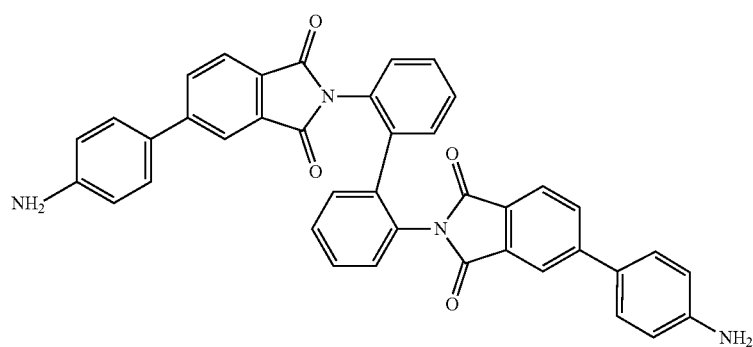
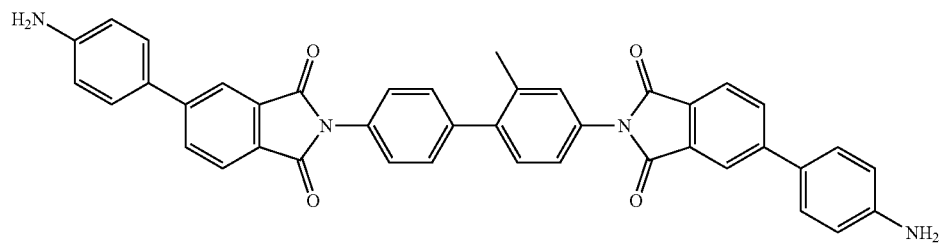

-continued
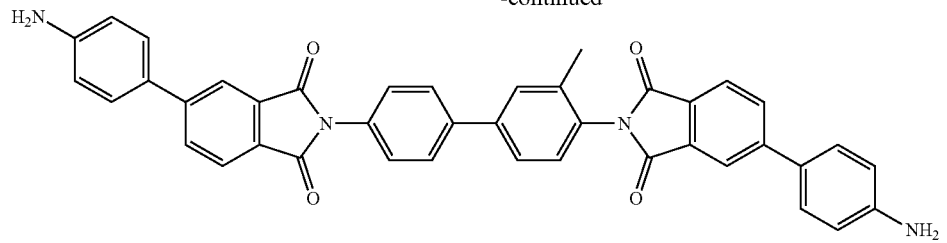
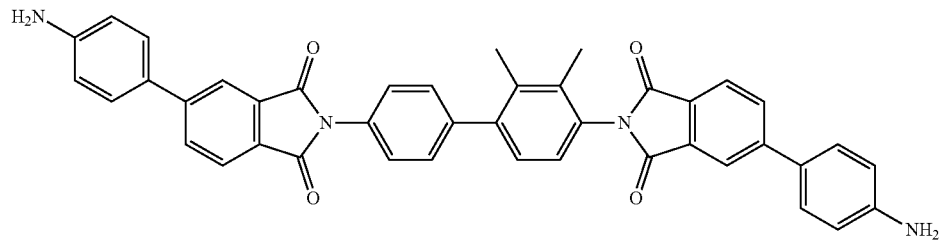
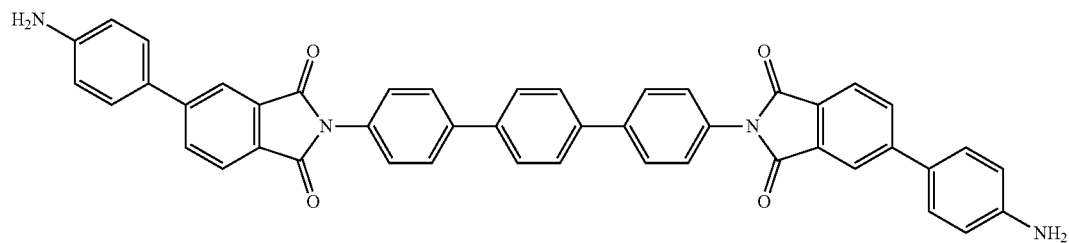
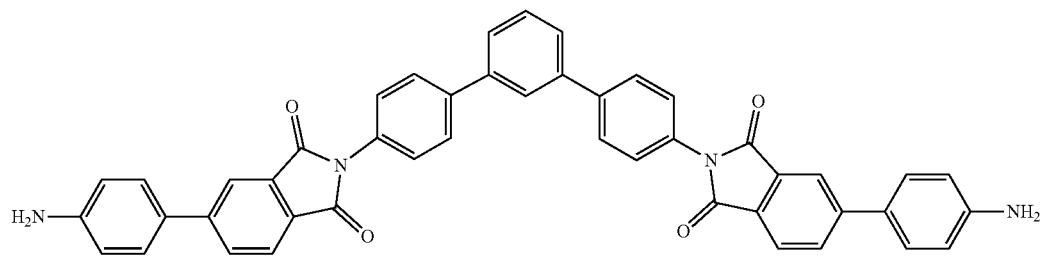
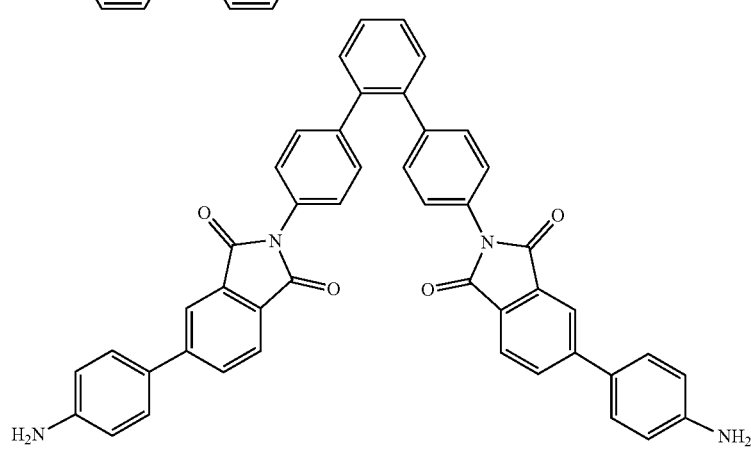
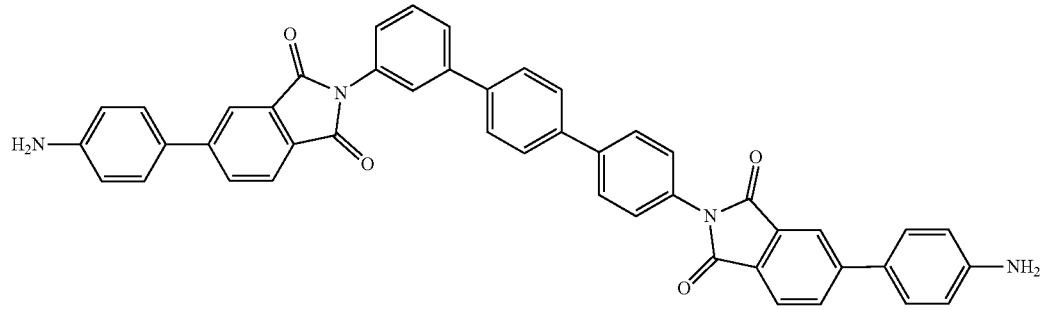

-continued
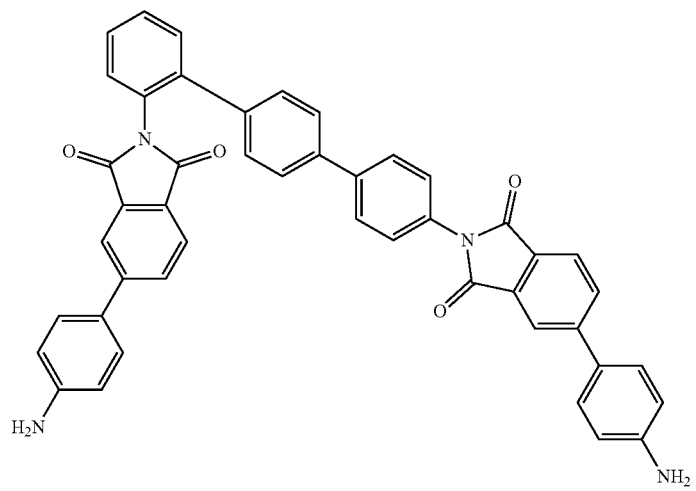
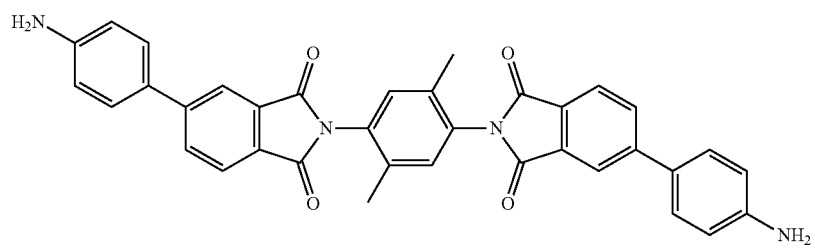
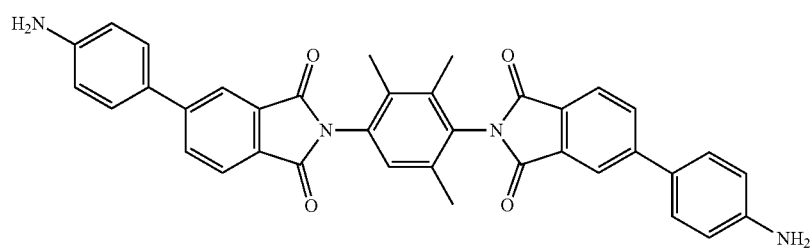
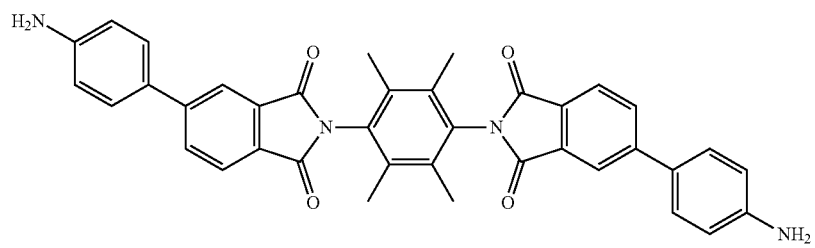
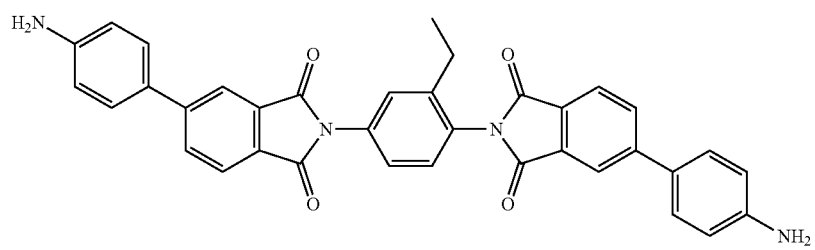

-continued
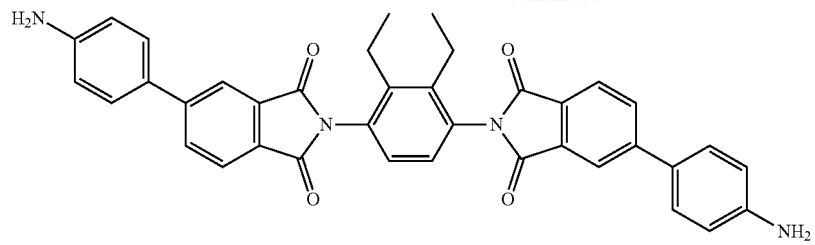
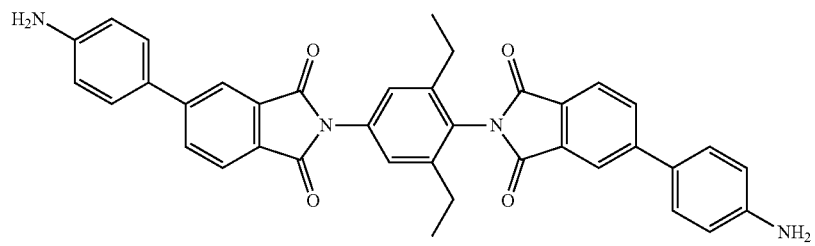
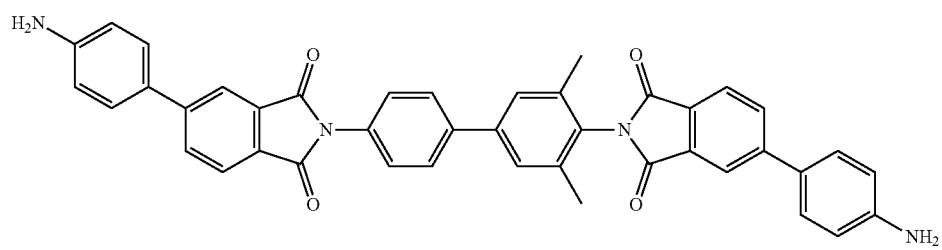
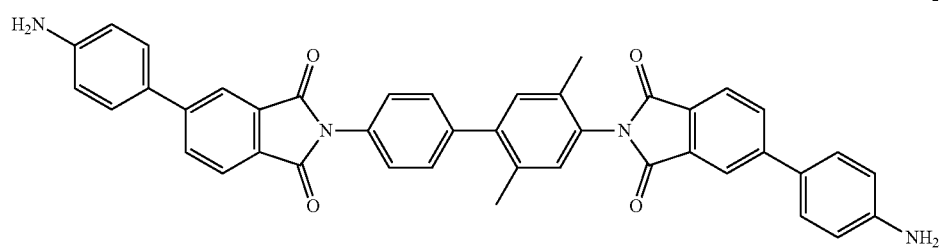
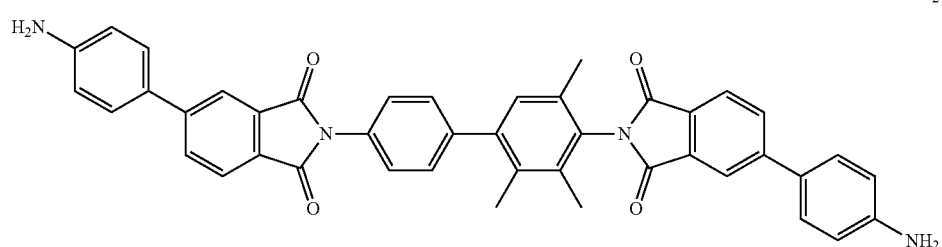
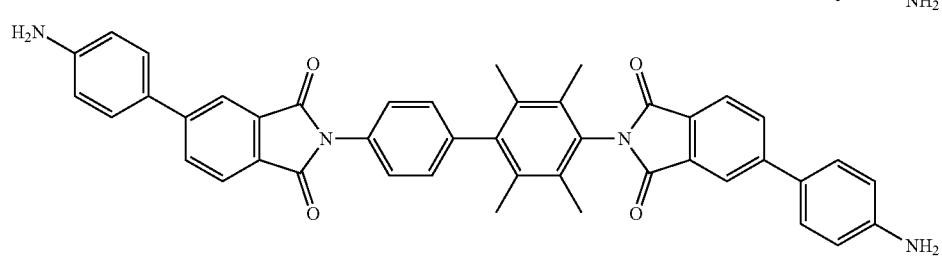
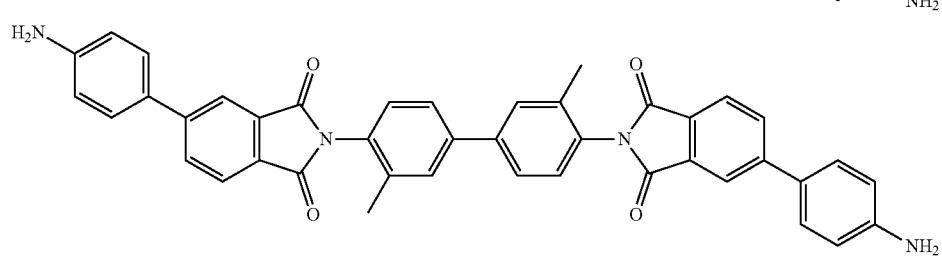

-continued
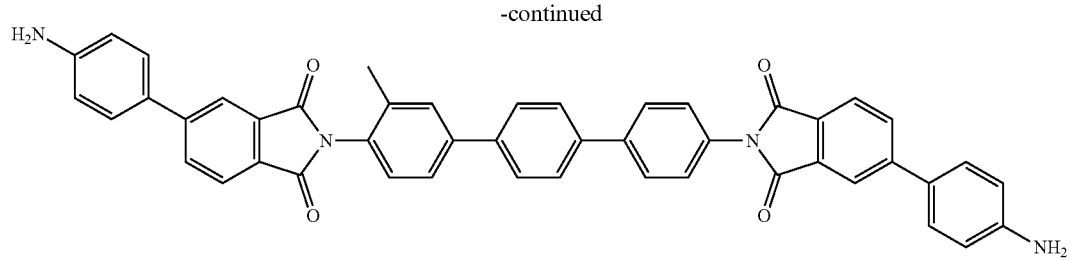
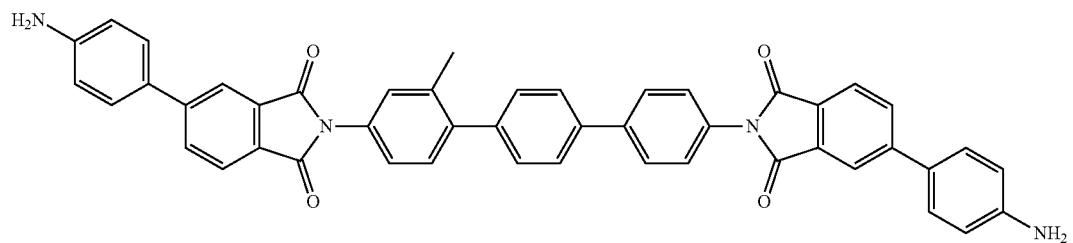
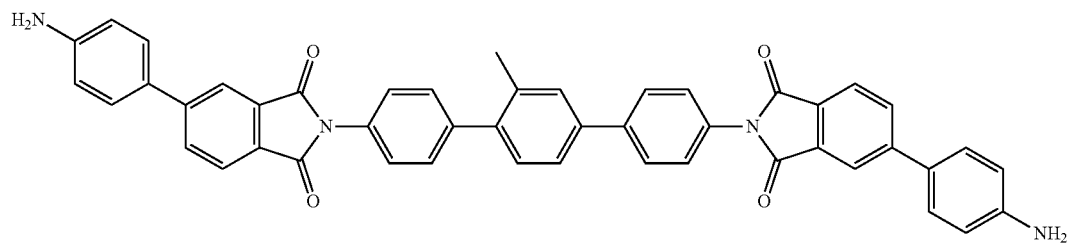
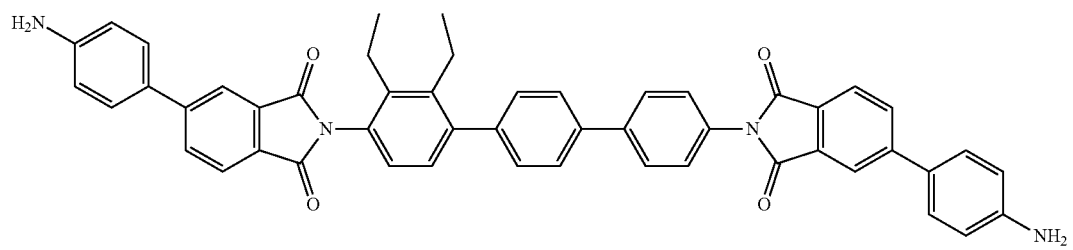
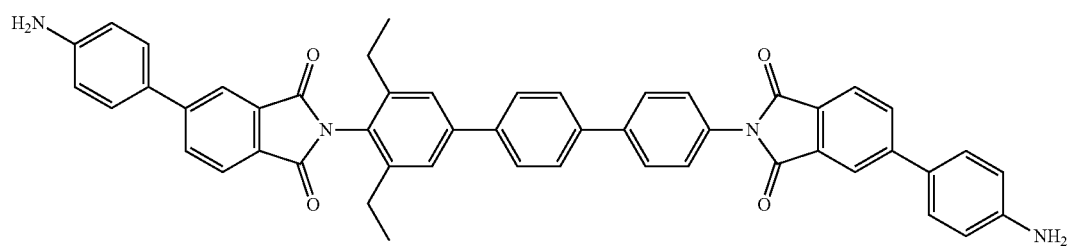
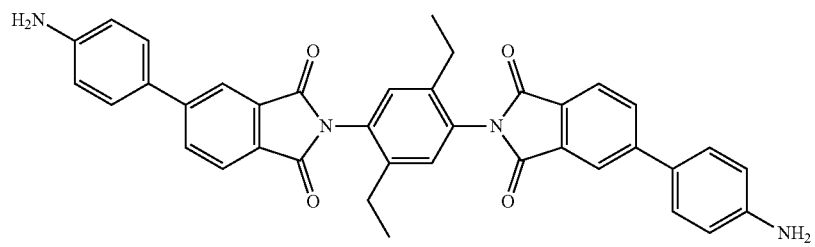

-continued
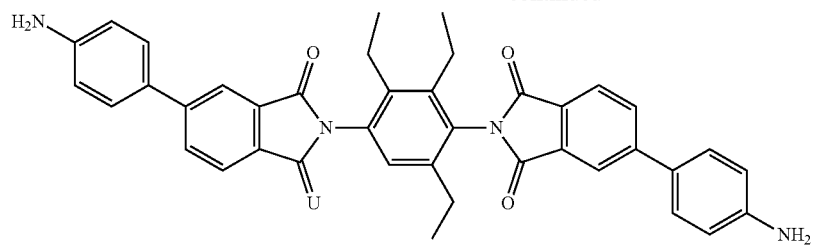
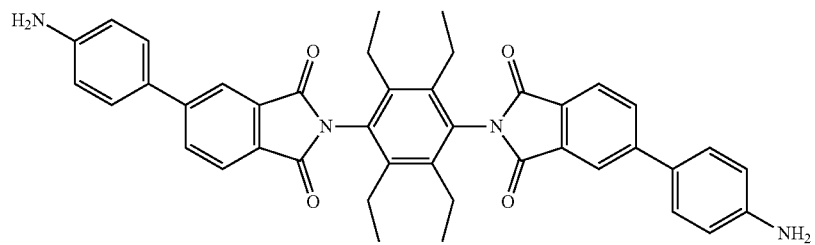
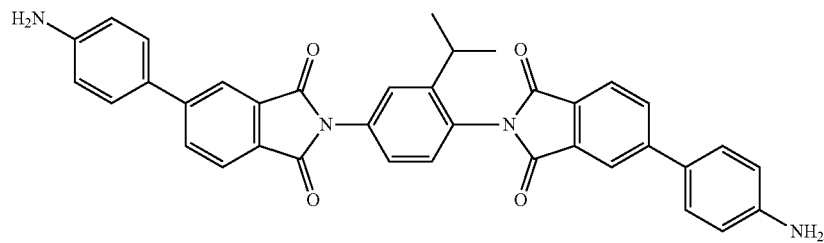
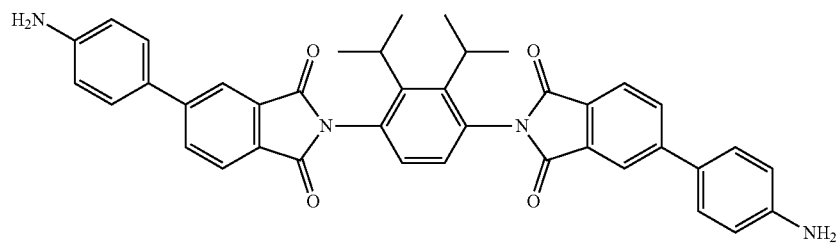
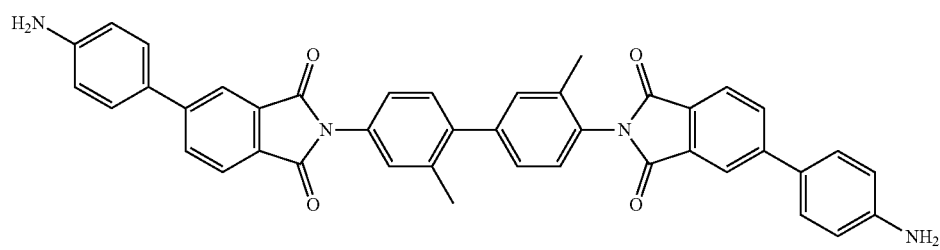
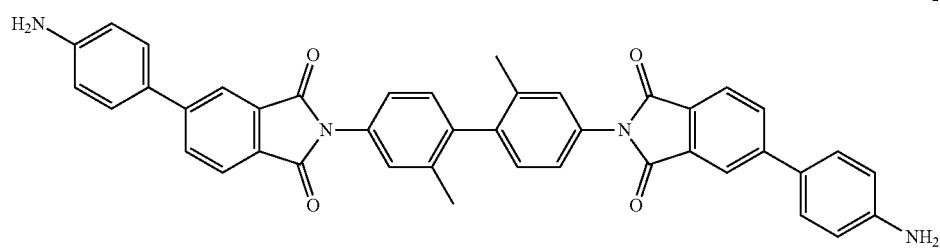
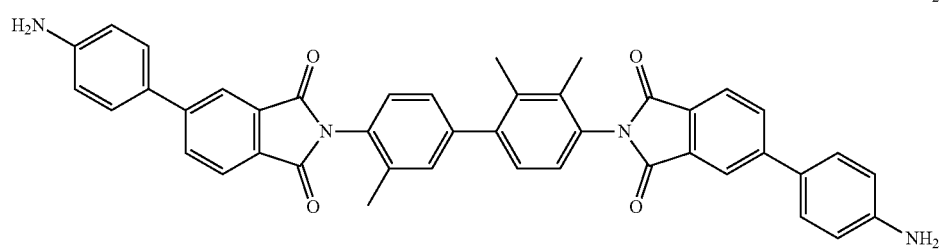

-continued
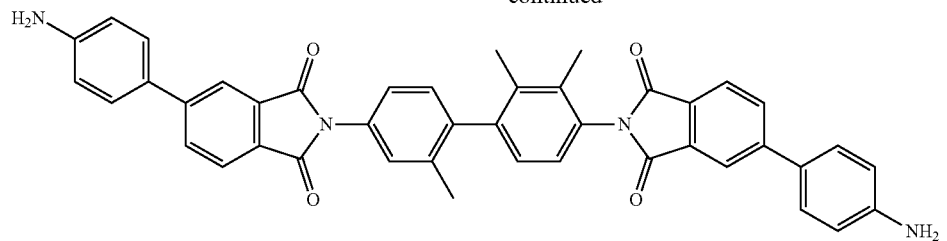
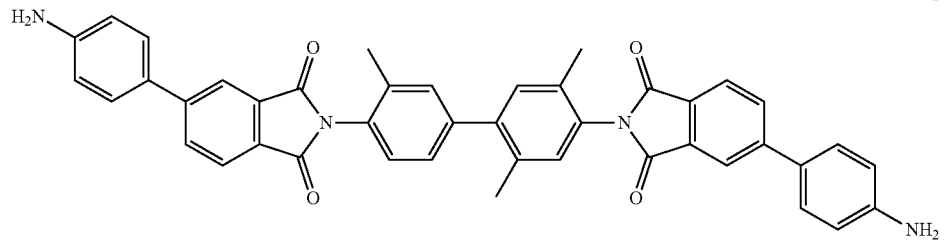
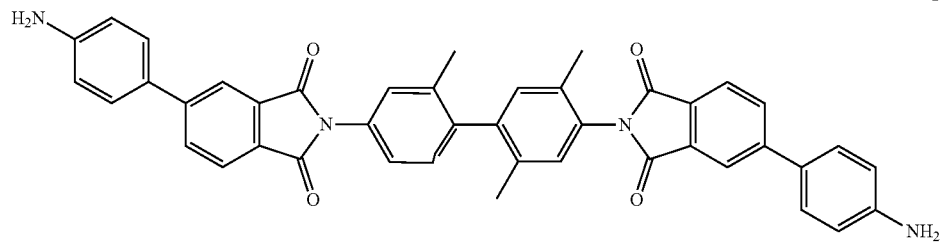
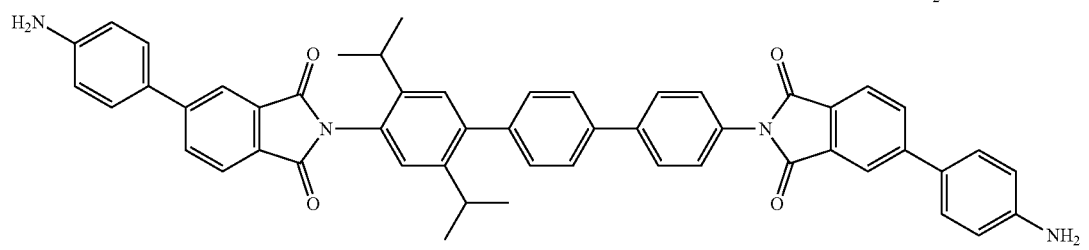
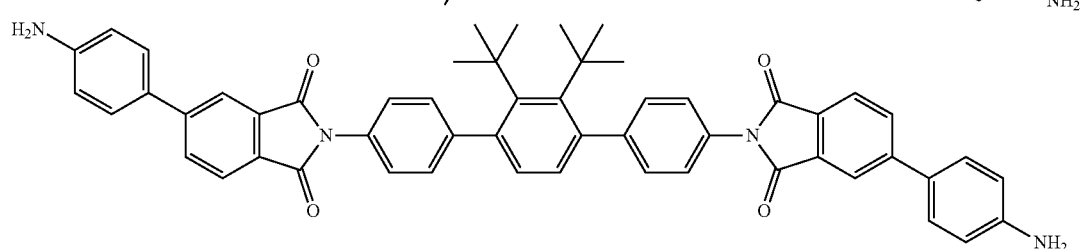
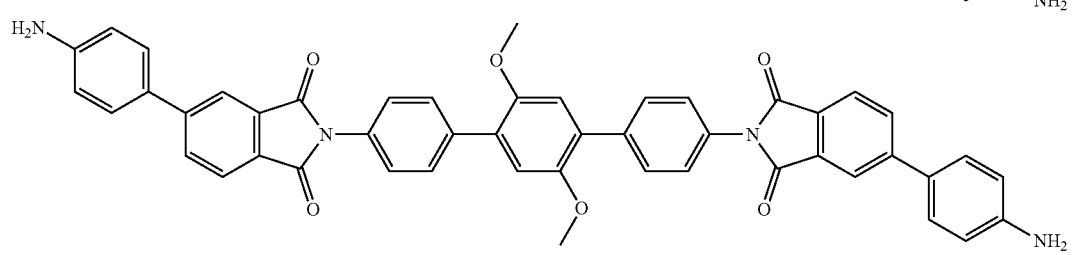
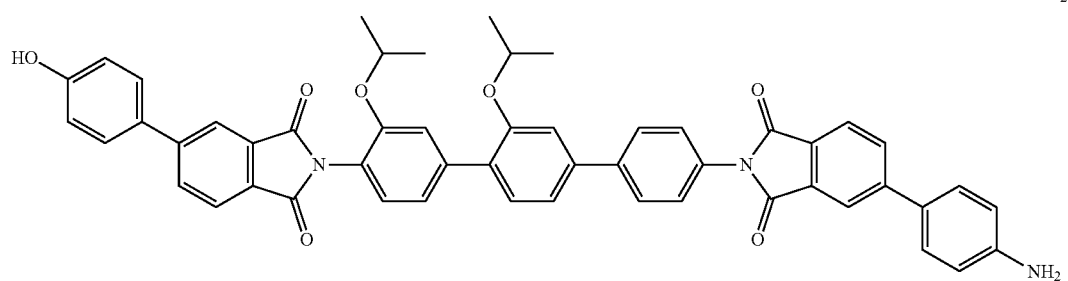

-continued
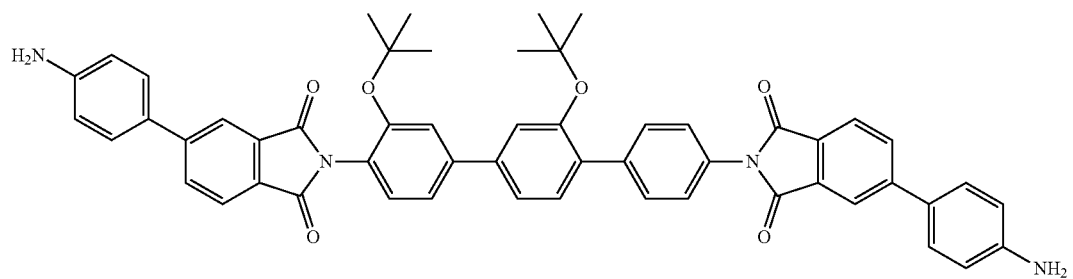
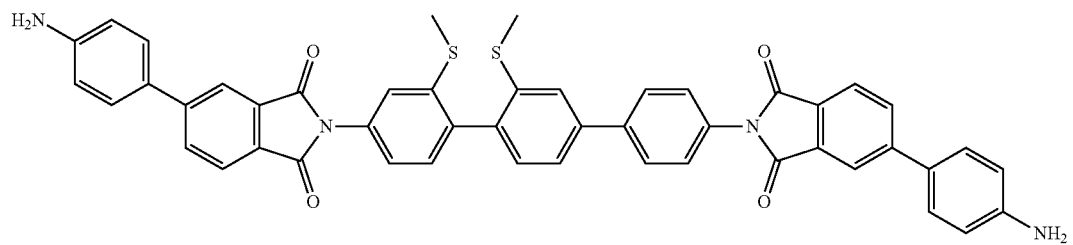
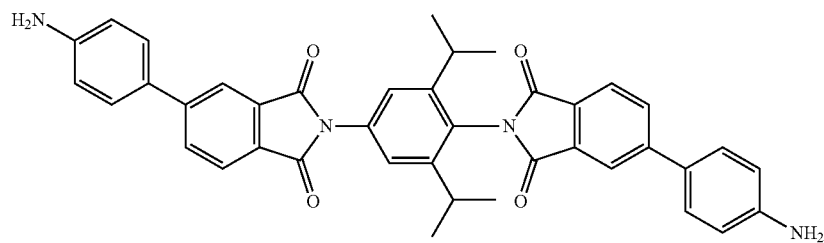
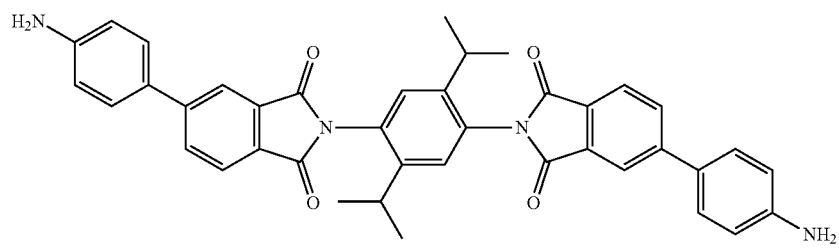
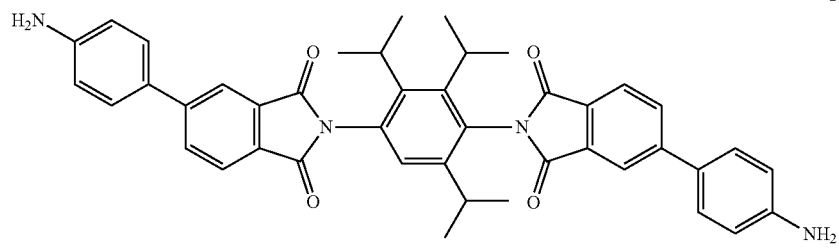
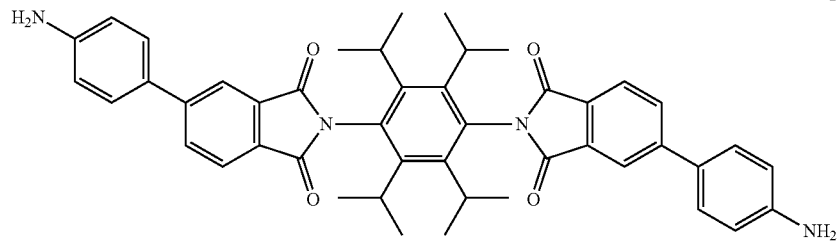

-continued
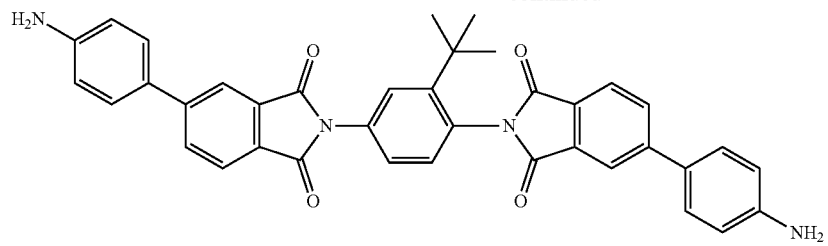
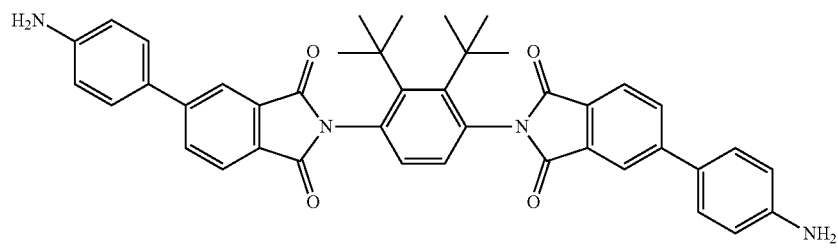
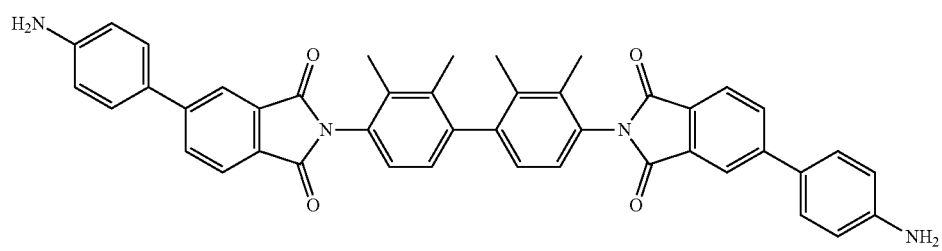
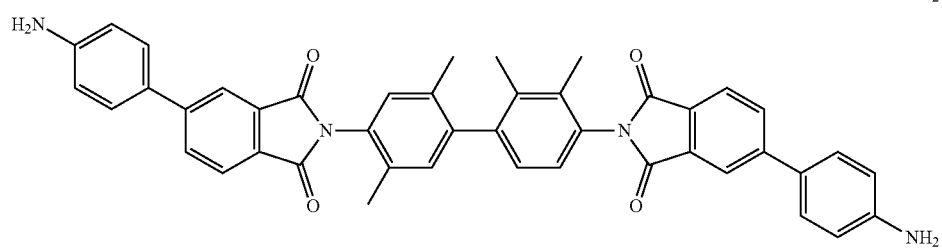
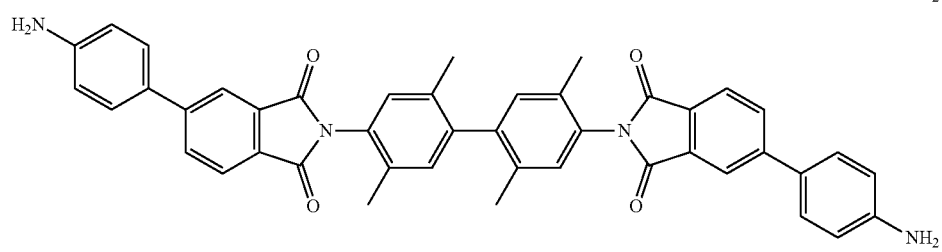
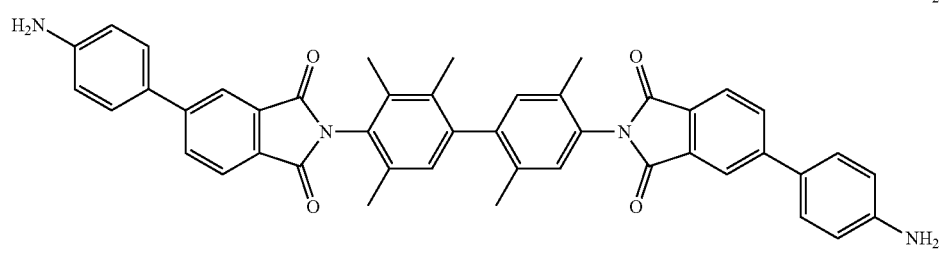
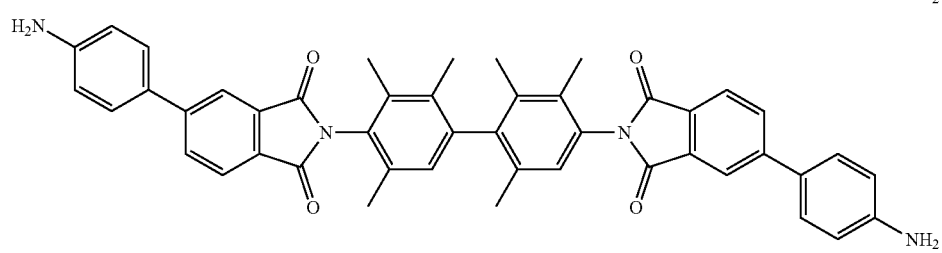

-continued
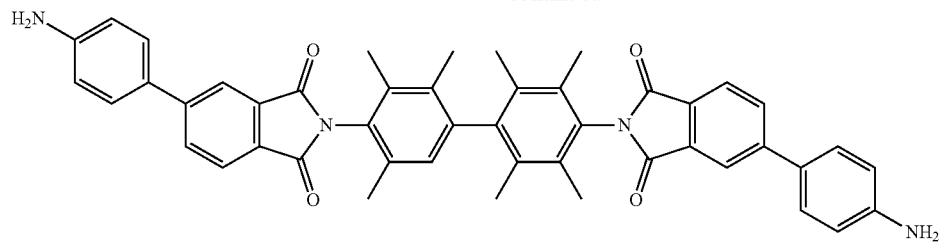
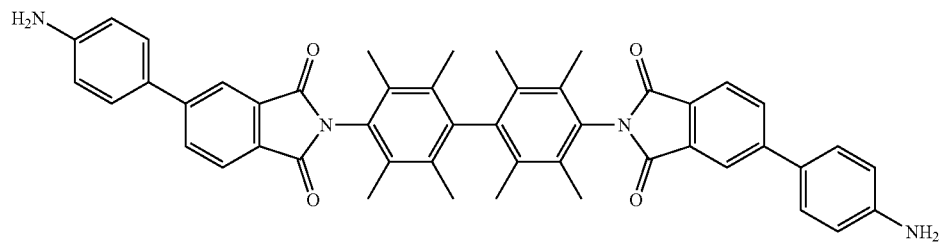
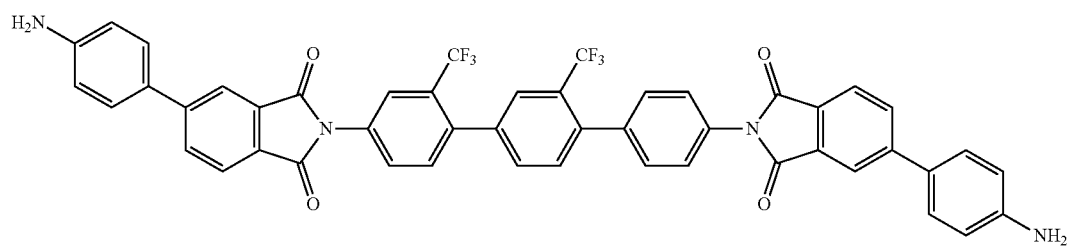
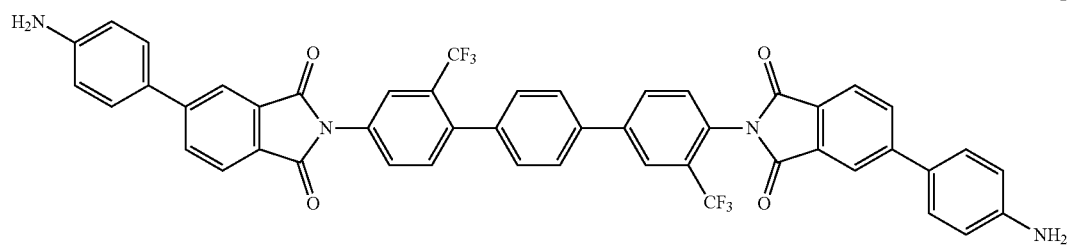
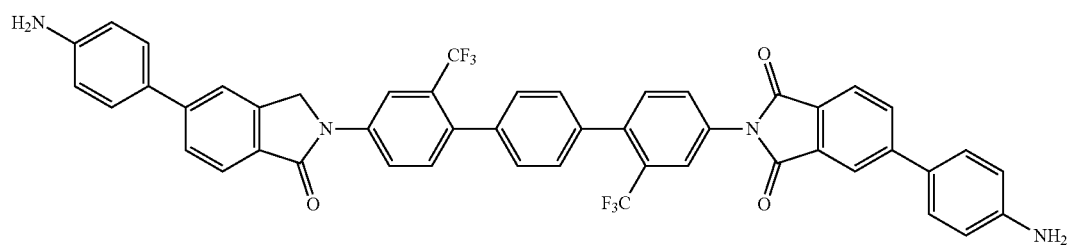
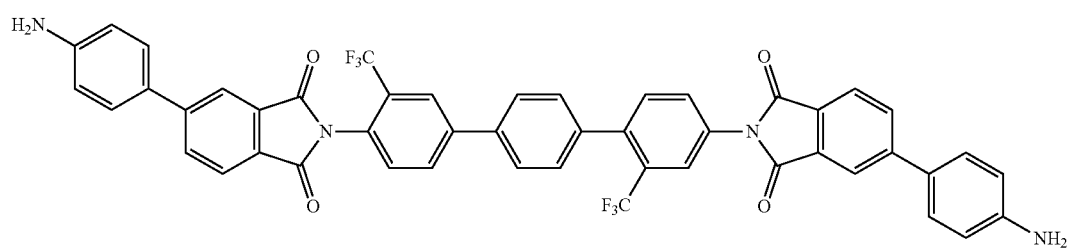
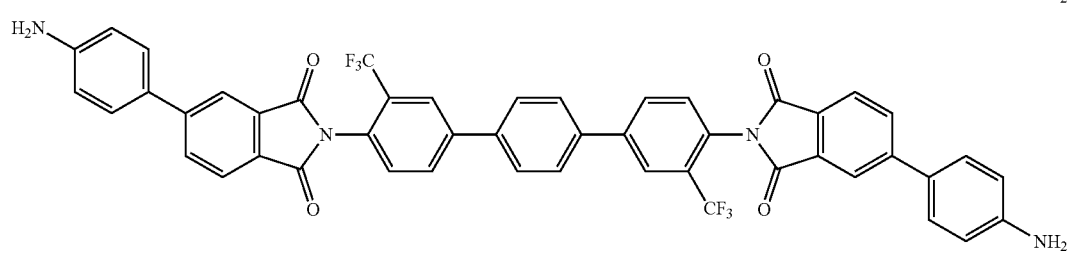

-continued
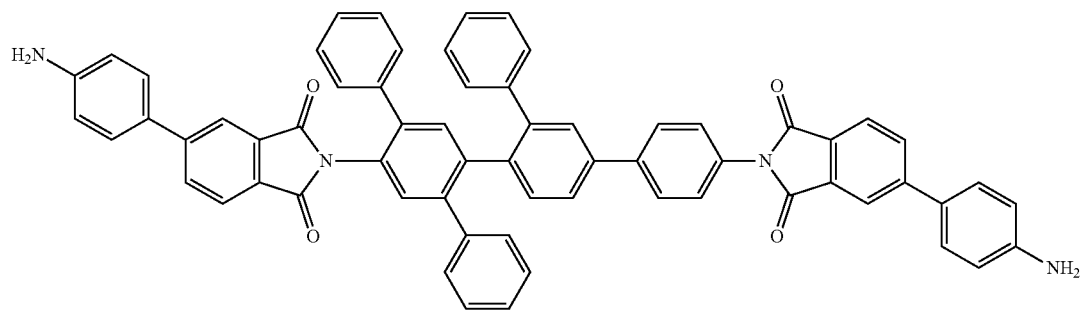
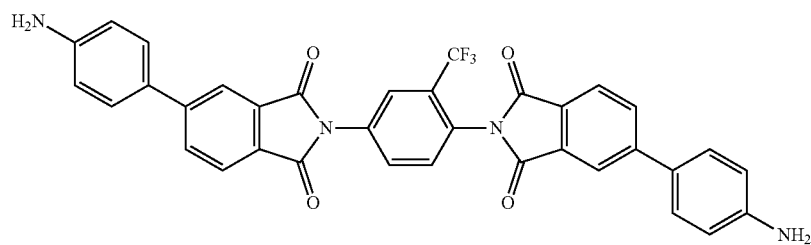
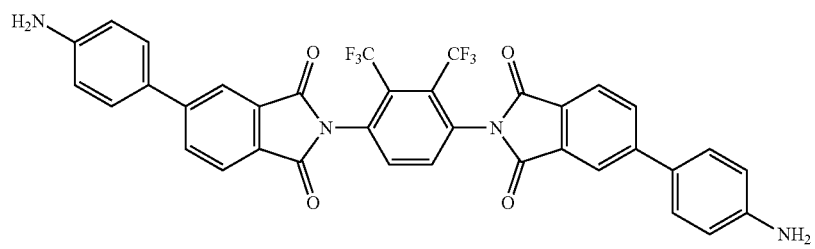
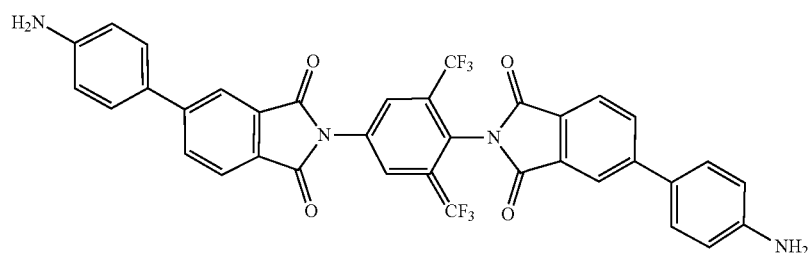
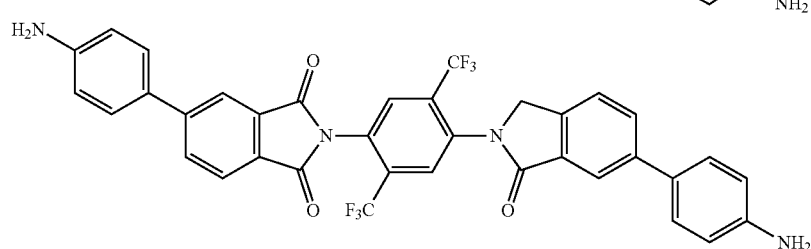
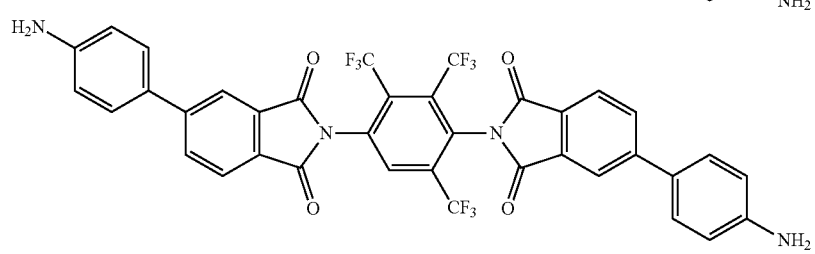

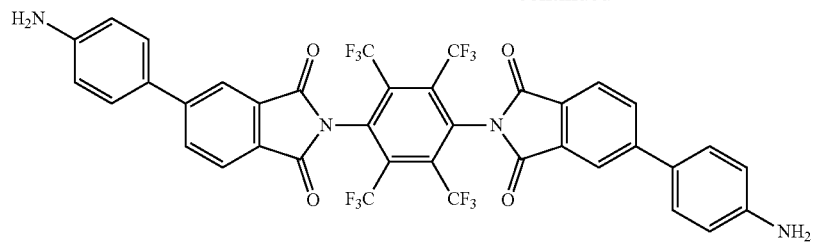
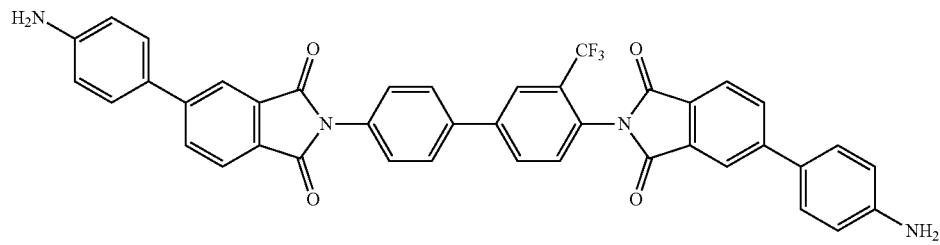
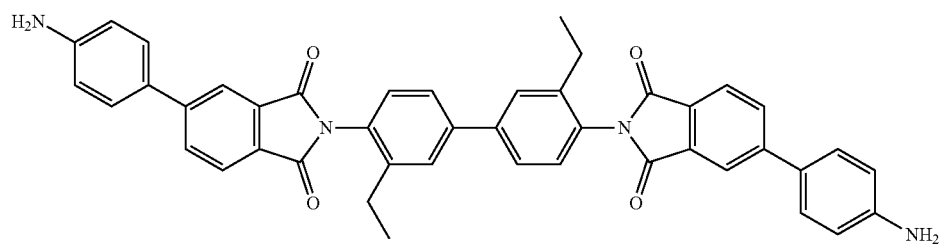
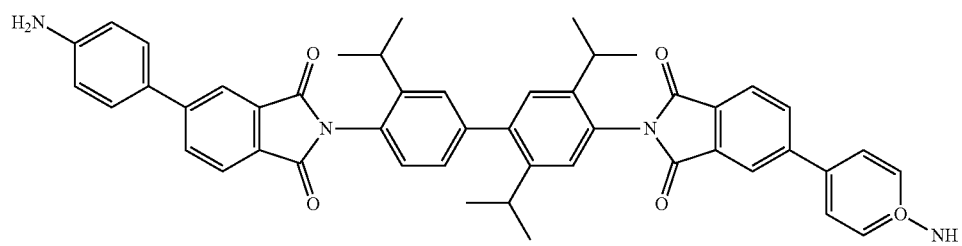
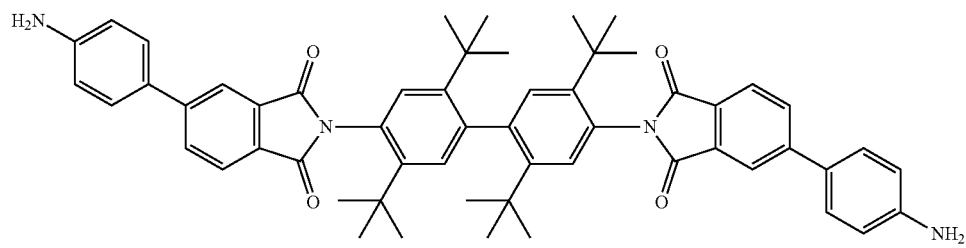
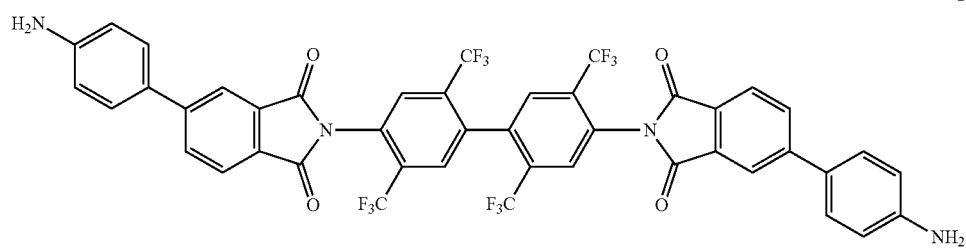
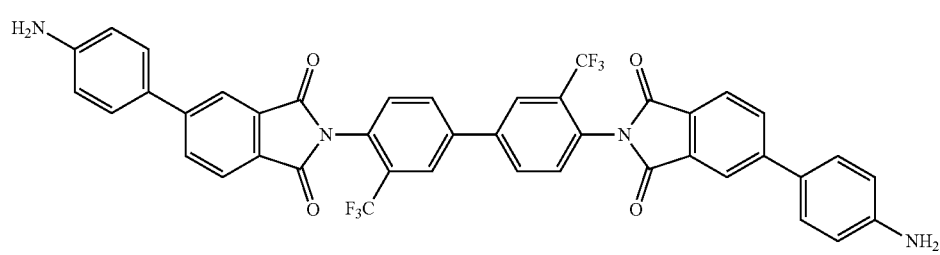

-continued
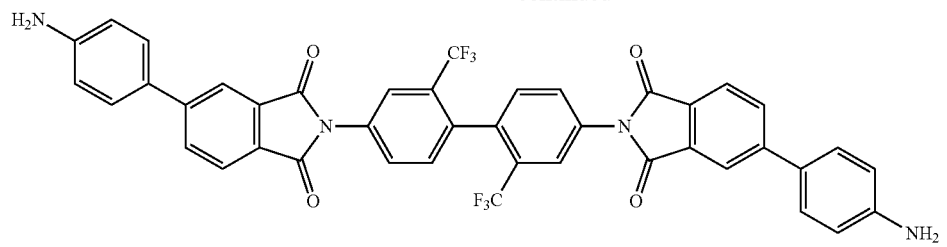
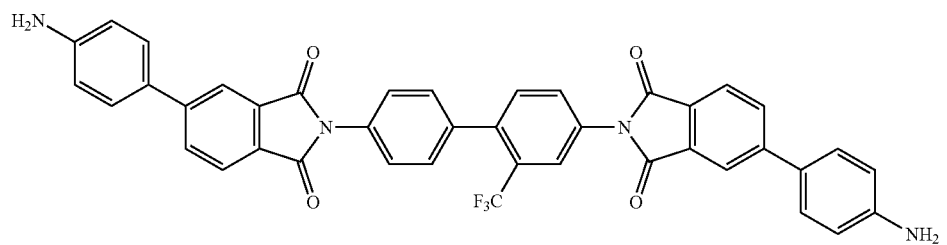
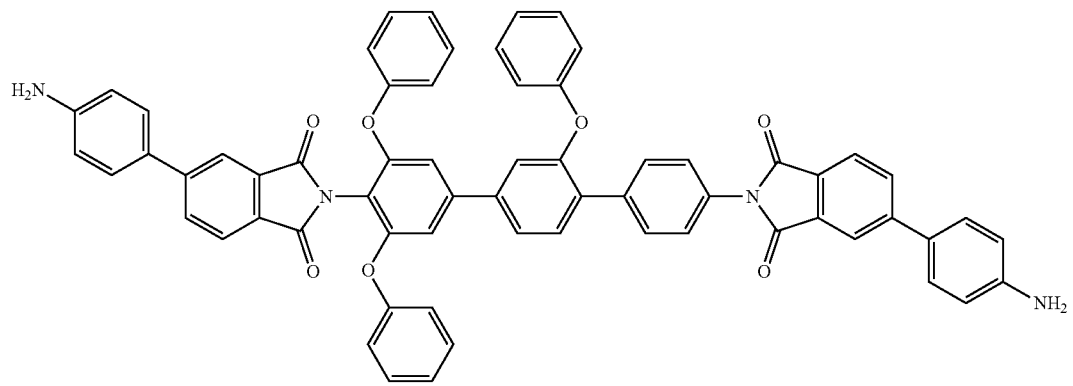
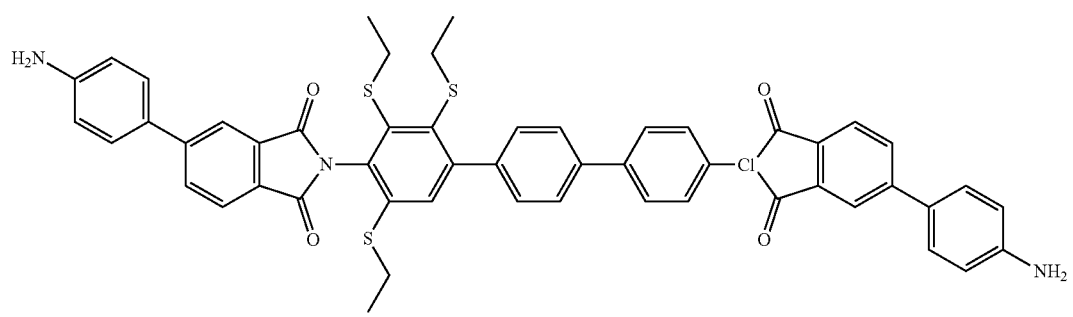
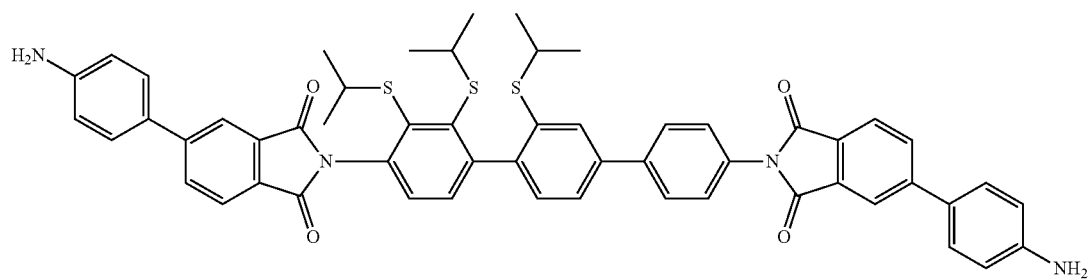

-continued
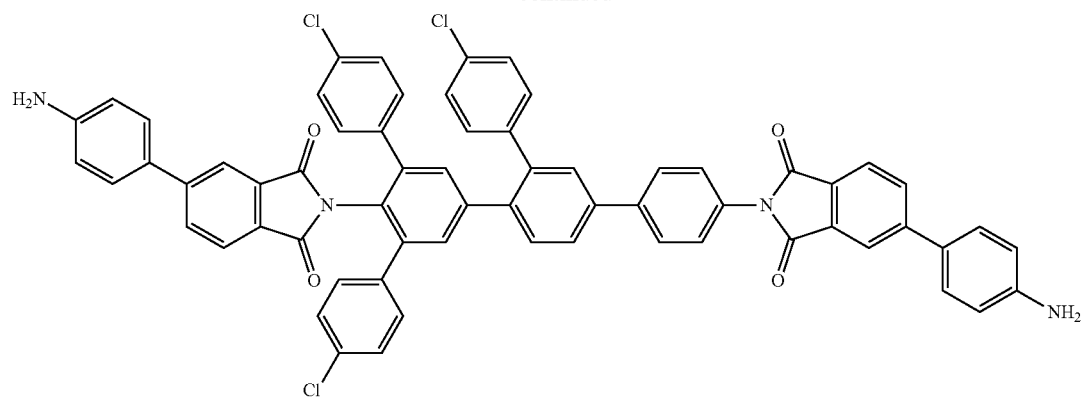
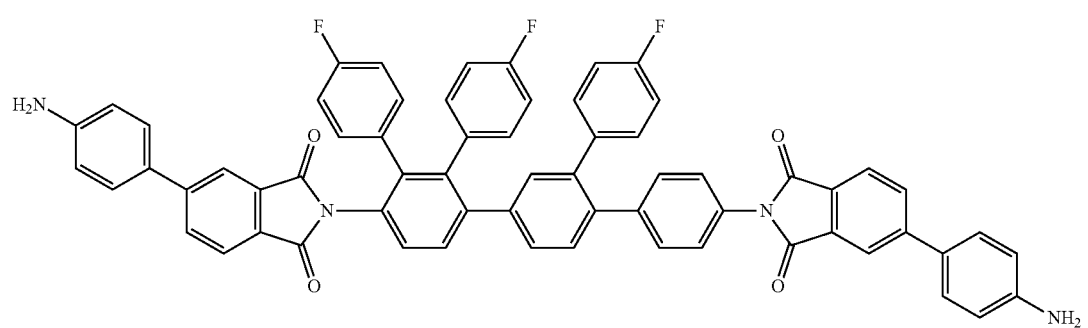
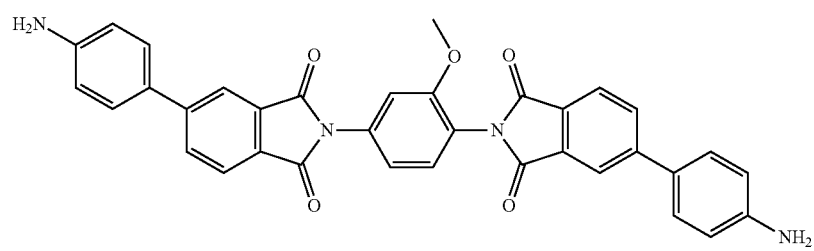
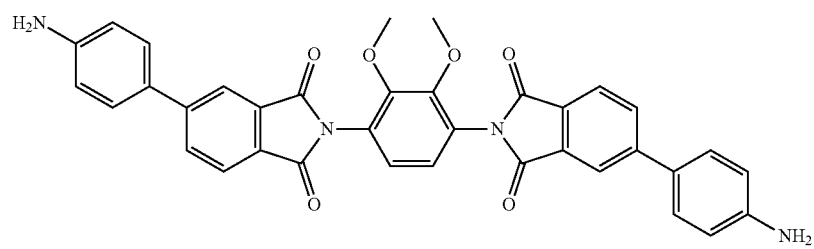
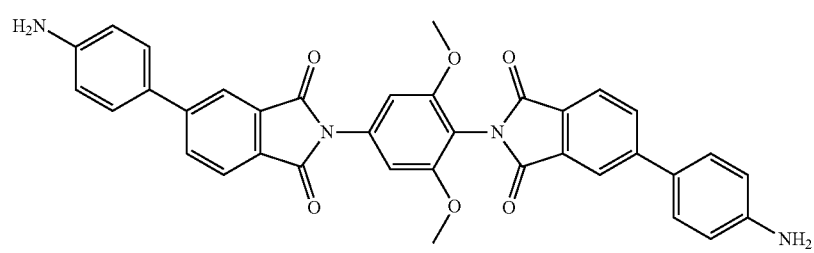

-continued
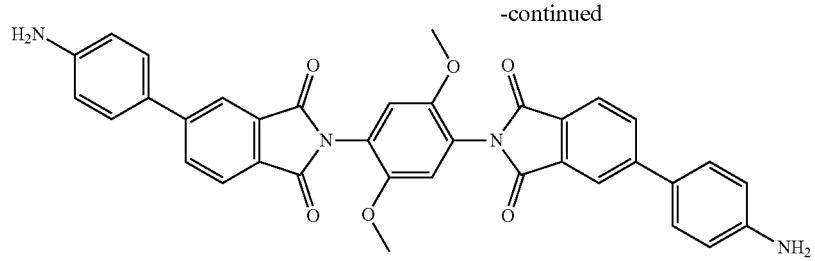
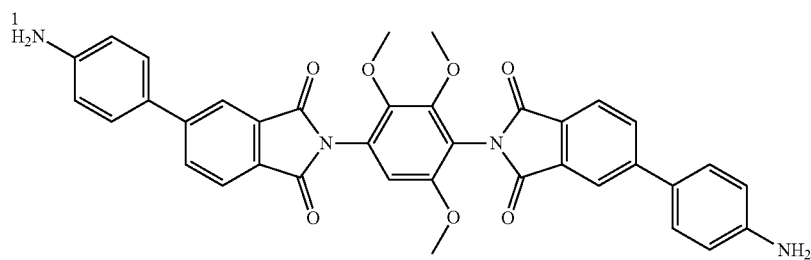
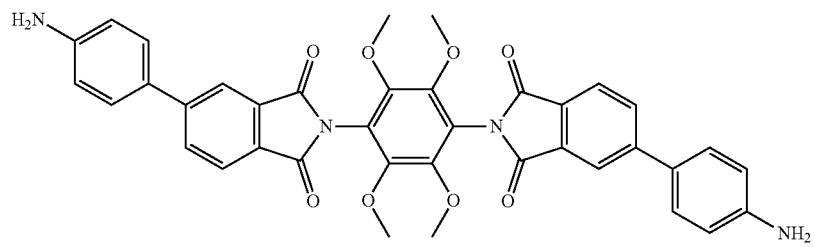
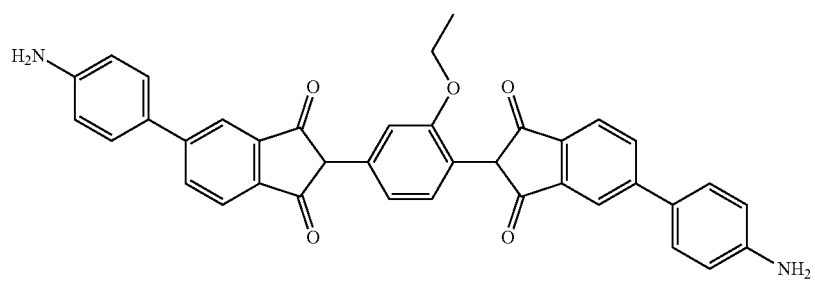
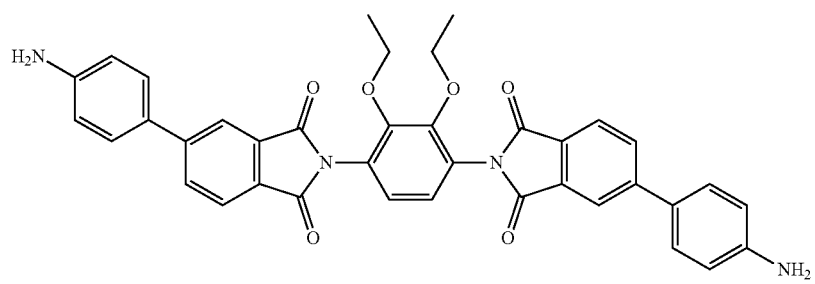
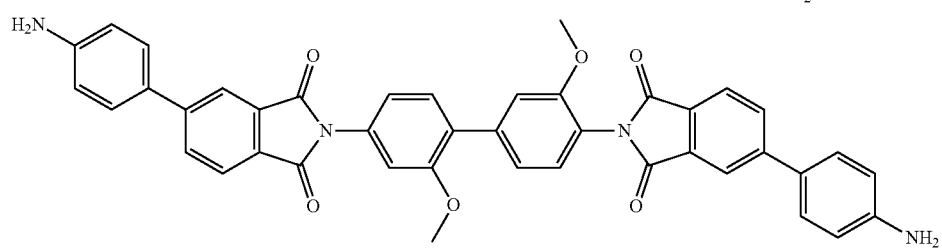

-continued
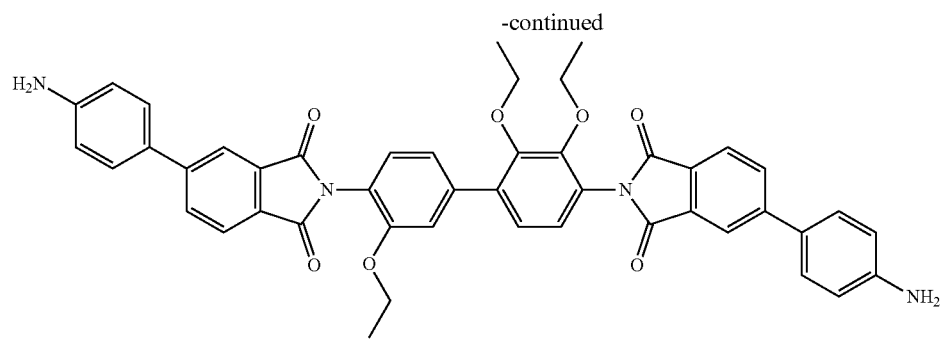
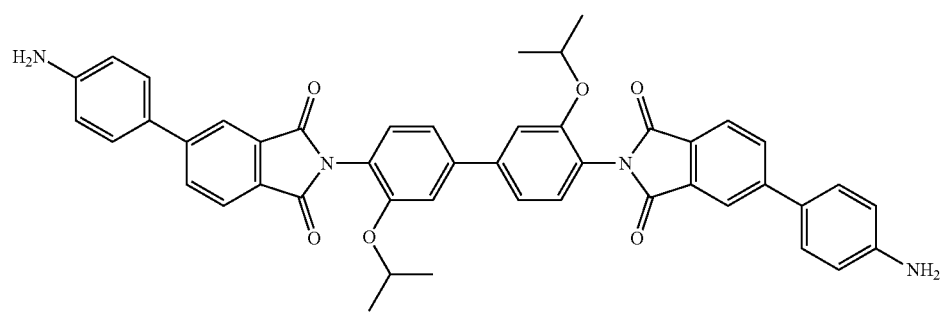
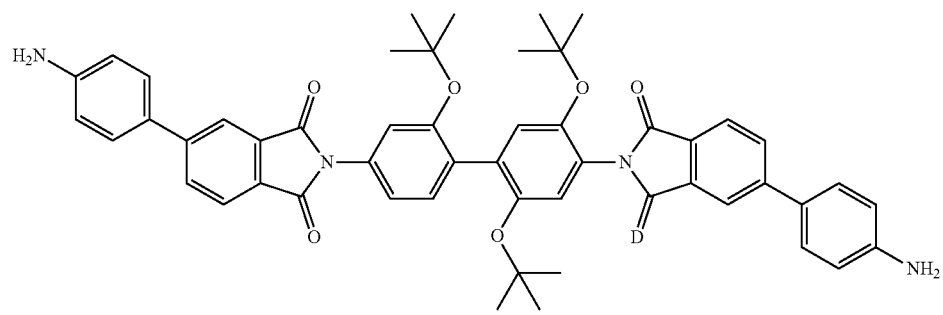
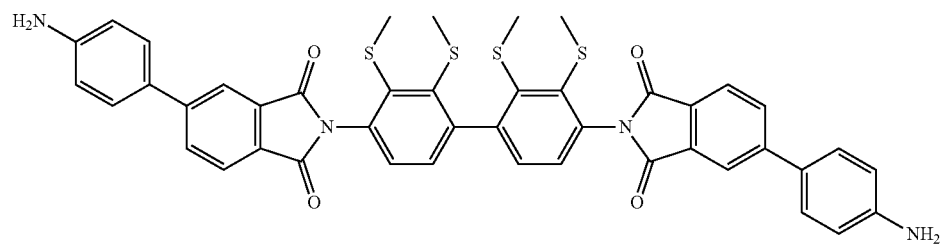
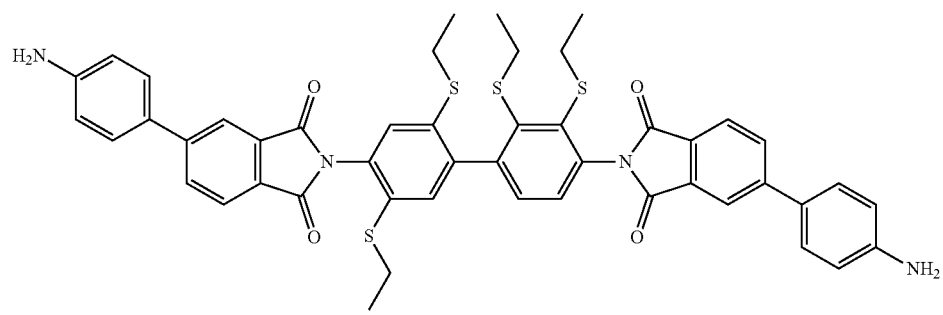

-continued
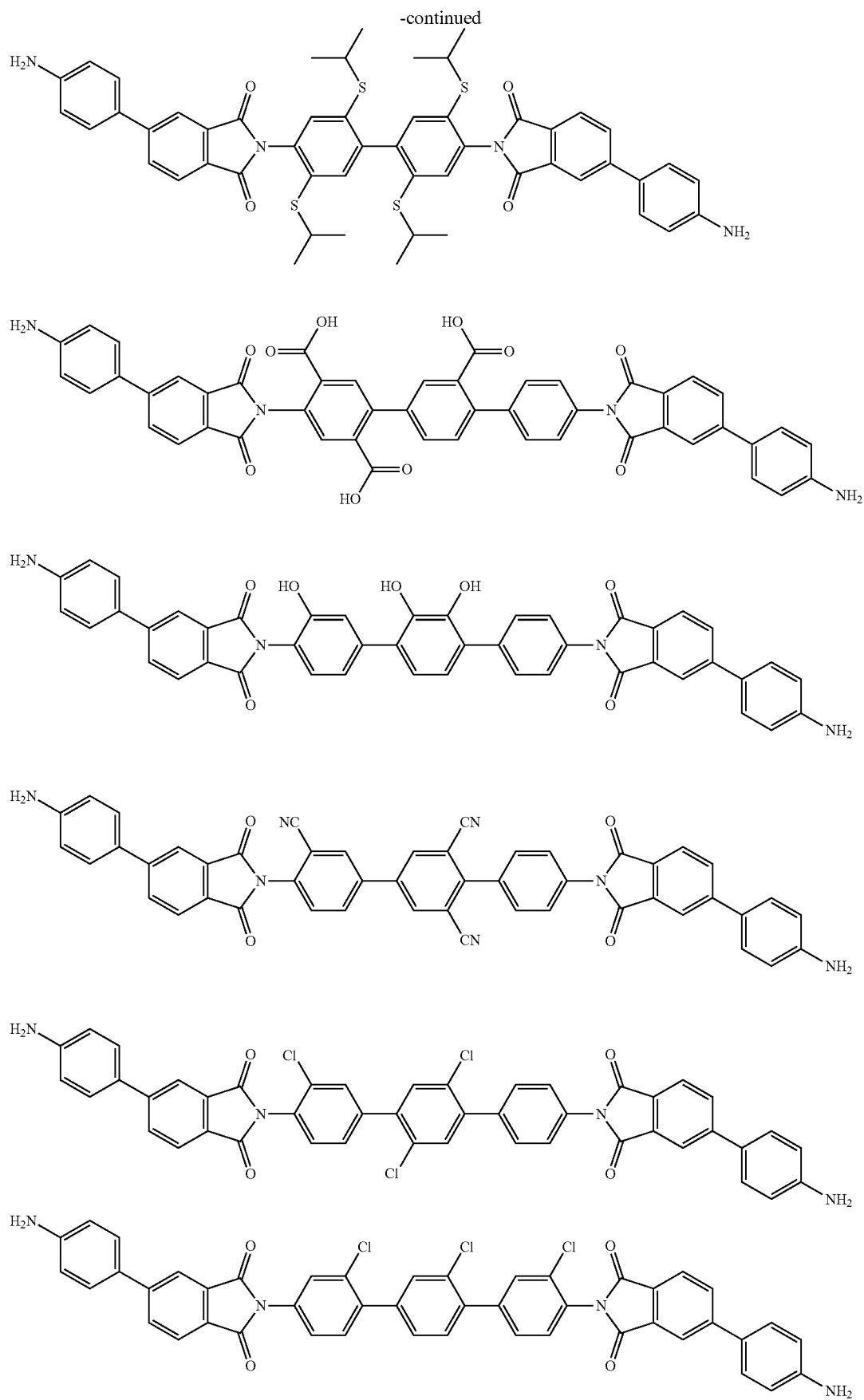

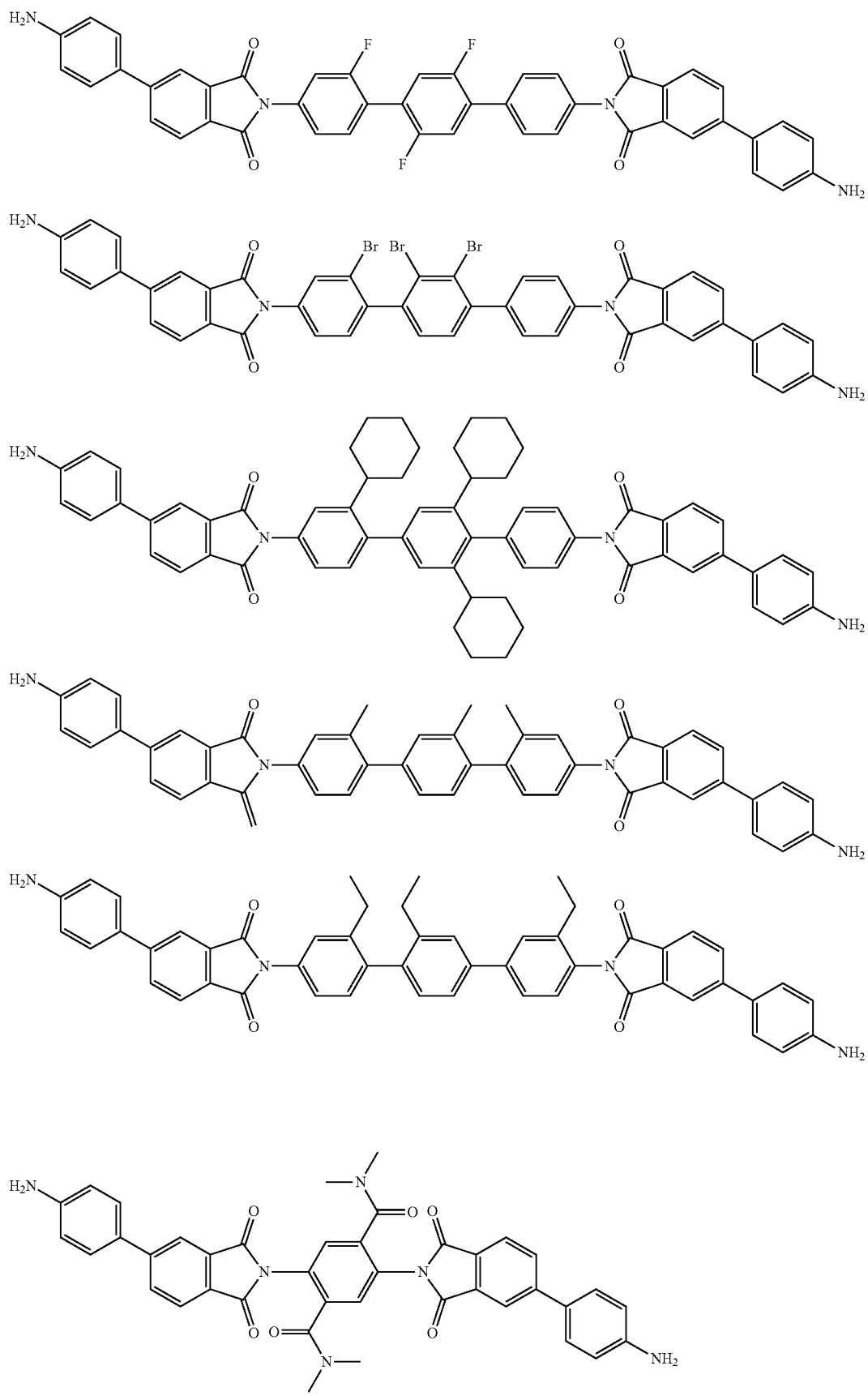

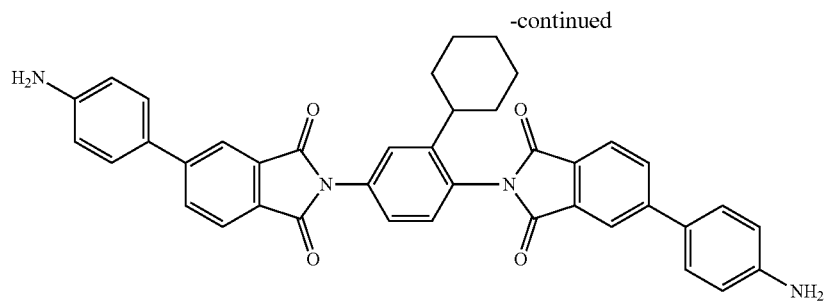
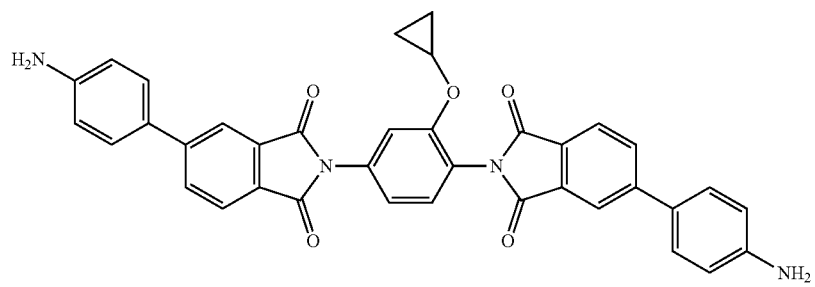
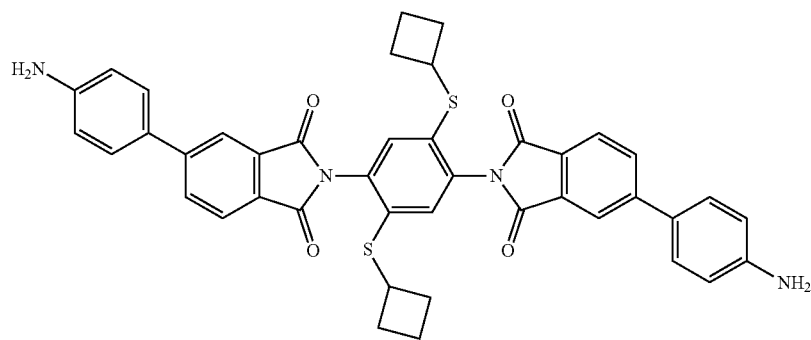
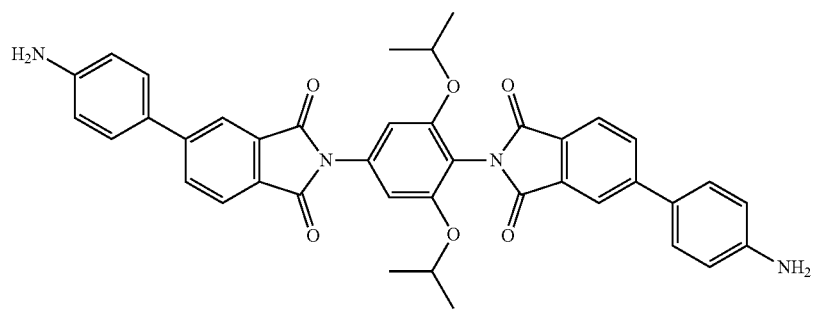
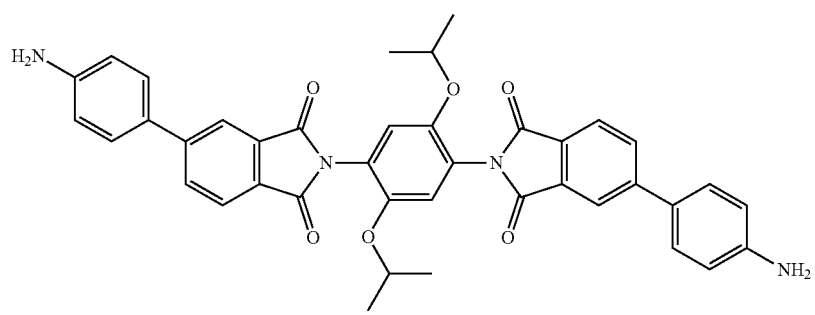

-continued
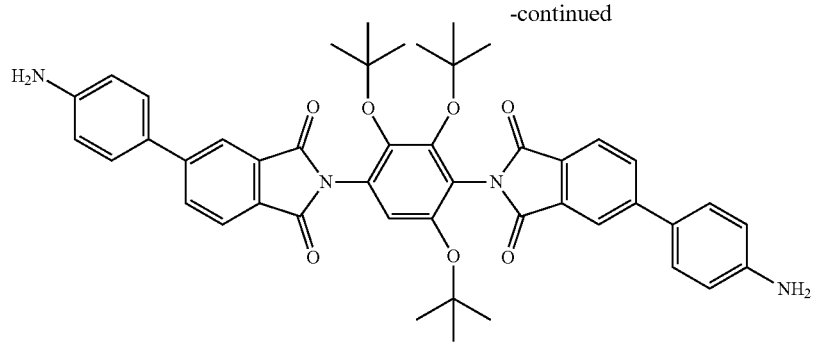
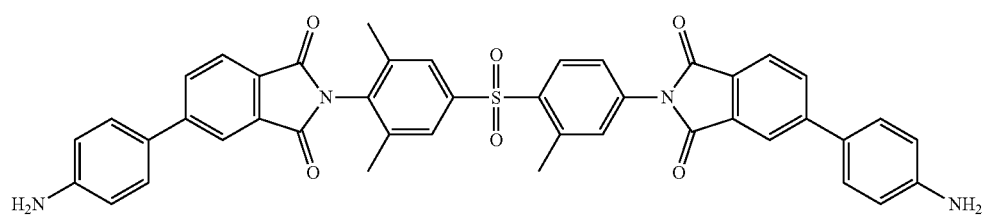
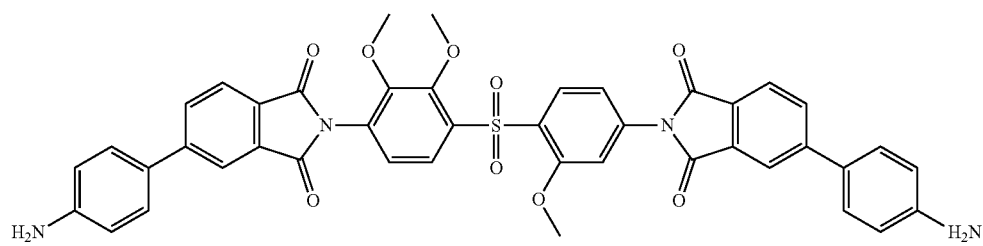
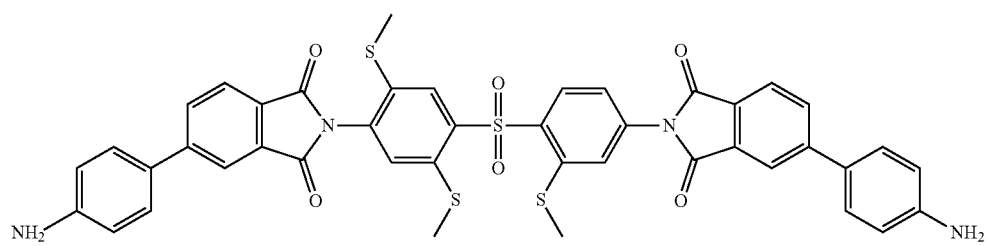
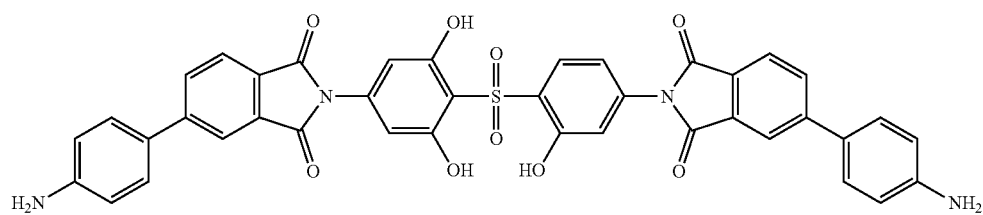
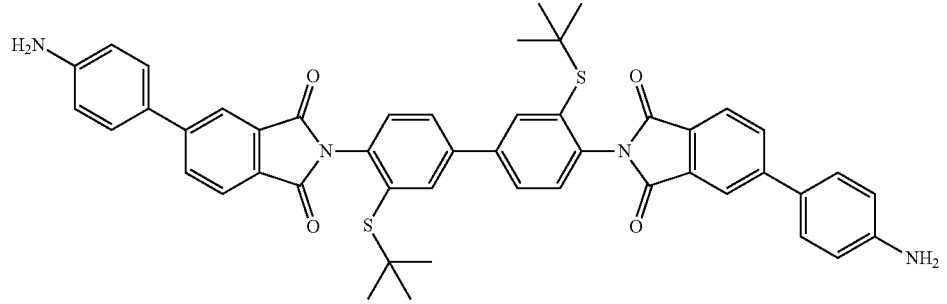

-continued
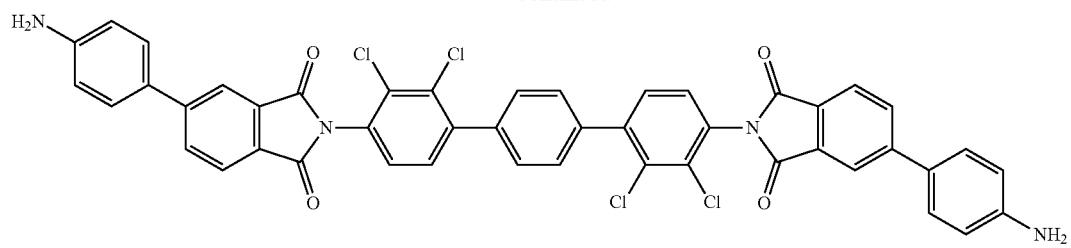
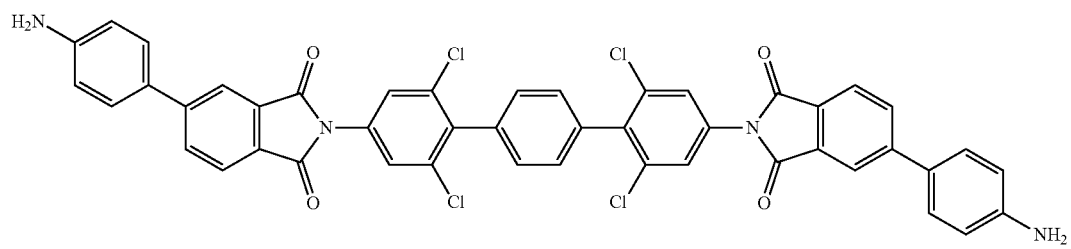
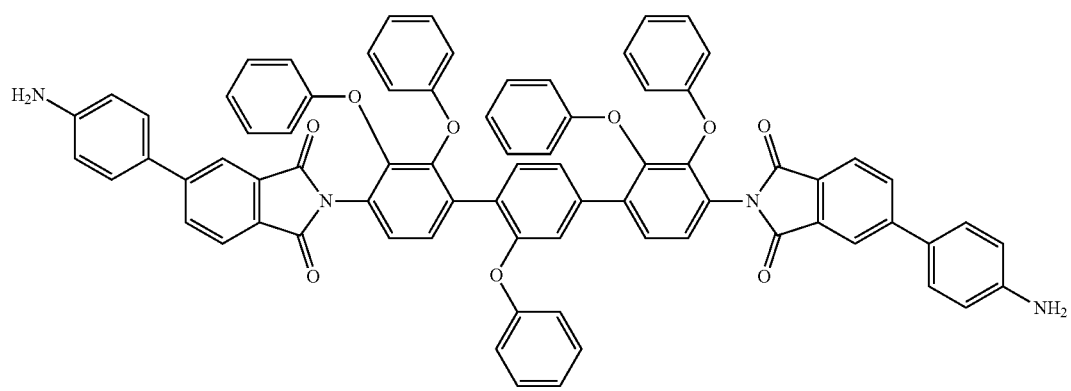 [SMILES: Nc1ccc(-c2ccc3c(c2)C(=O)N(c2ccc(-c4ccc(-c5ccc(N6C(=O)c7ccc(-c8ccc(N)cc8)cc7C6=O)c(Oc6ccccc6)c5Oc5ccccc5)c(Oc5ccccc5)c4)c(Oc4ccccc4)c2Oc2ccccc2)C3=O)cc1]
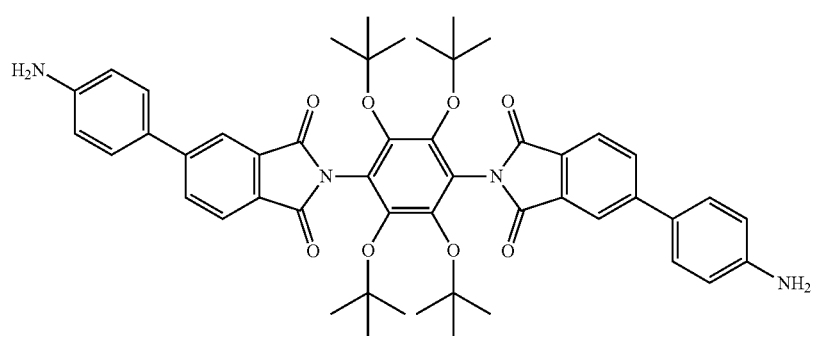
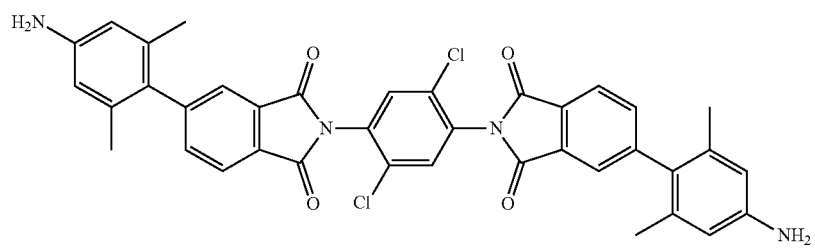
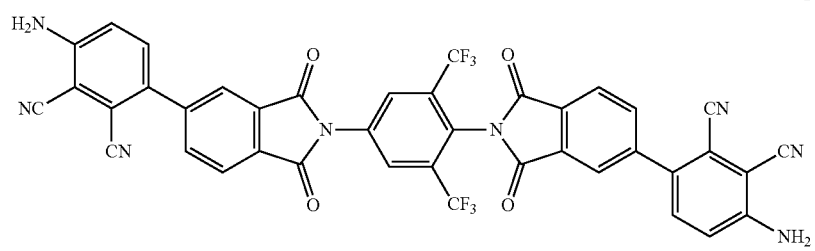

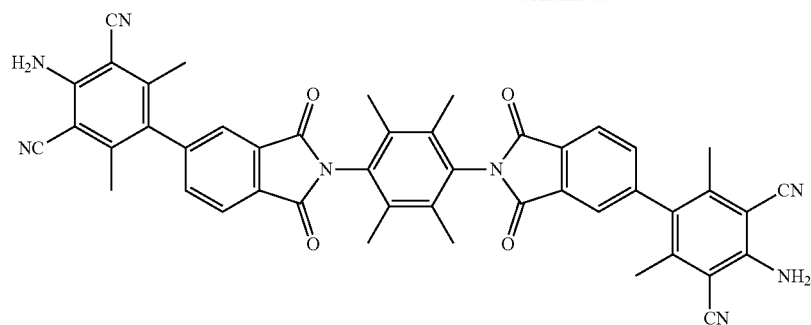
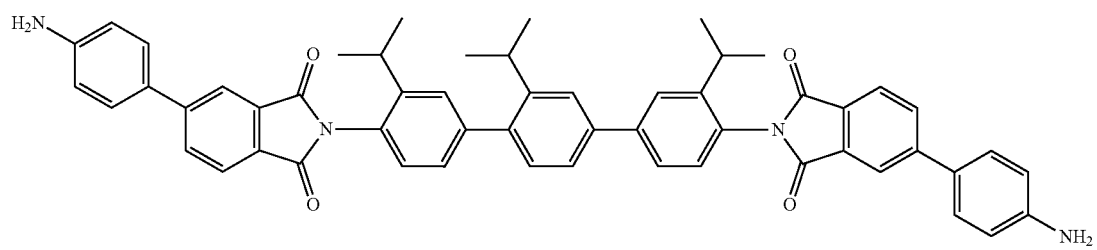
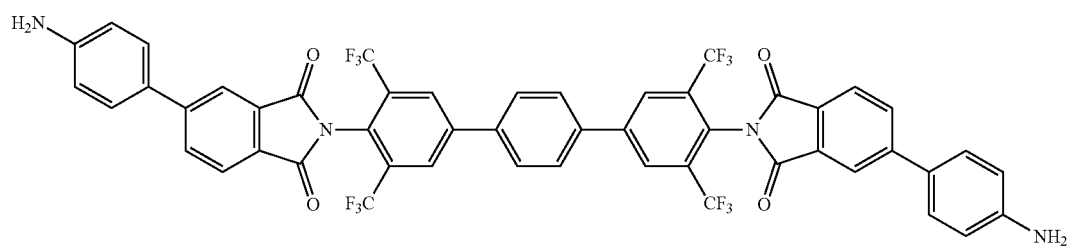
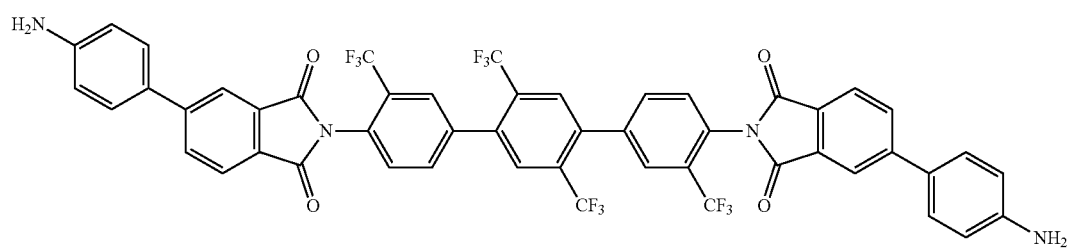
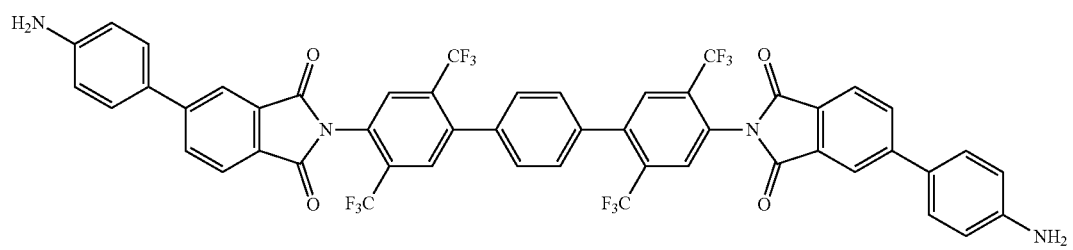
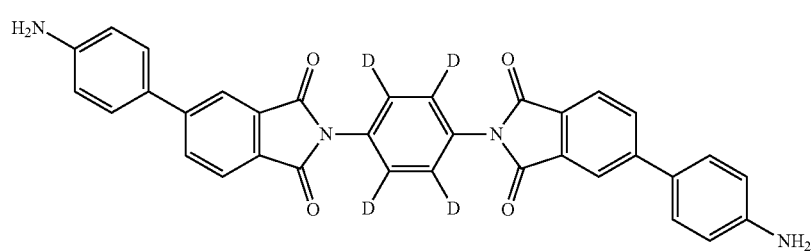

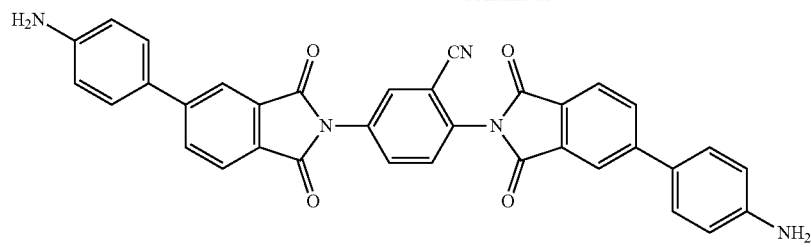
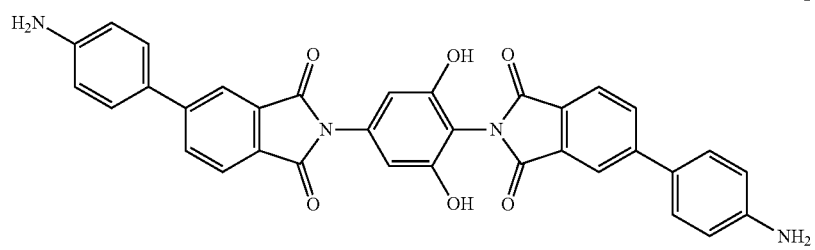
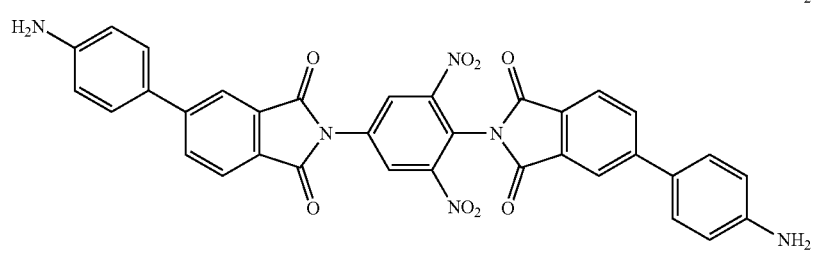
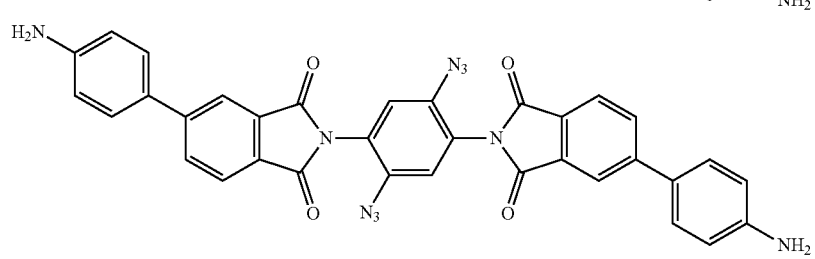
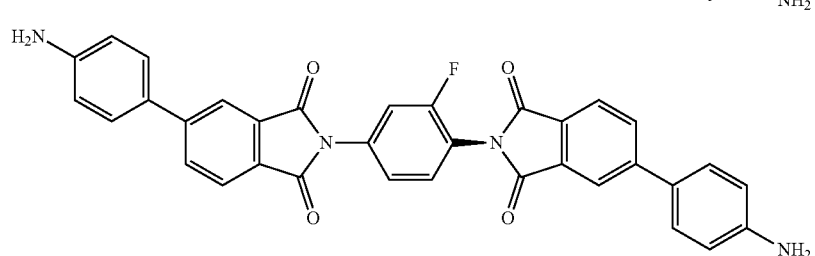
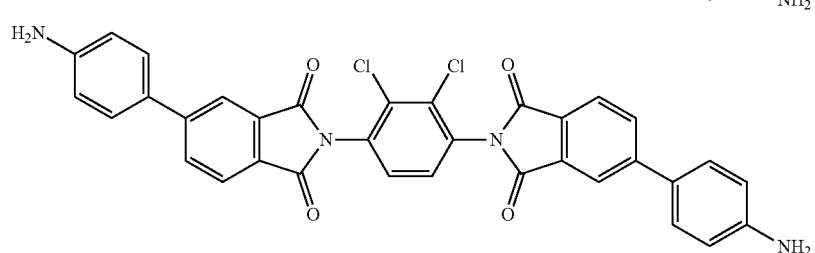
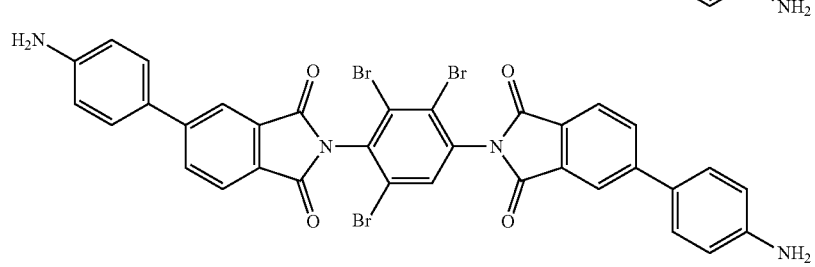

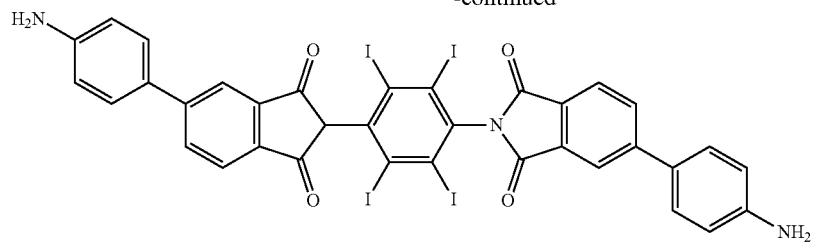
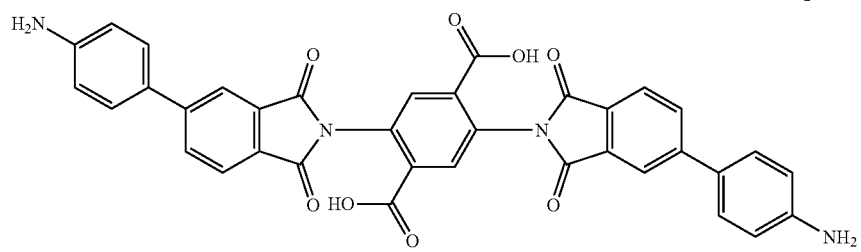
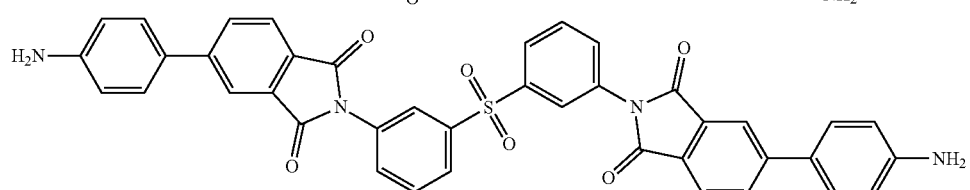
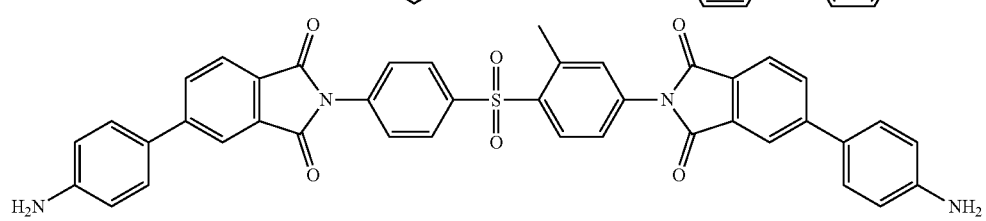
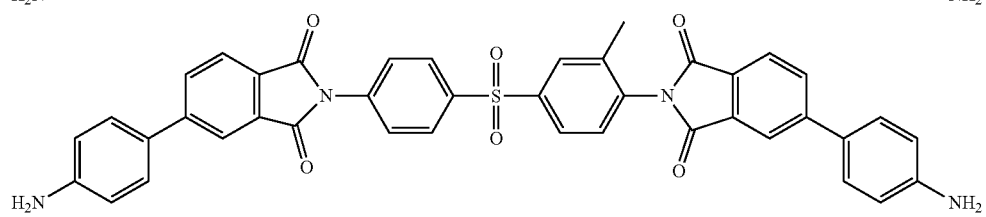
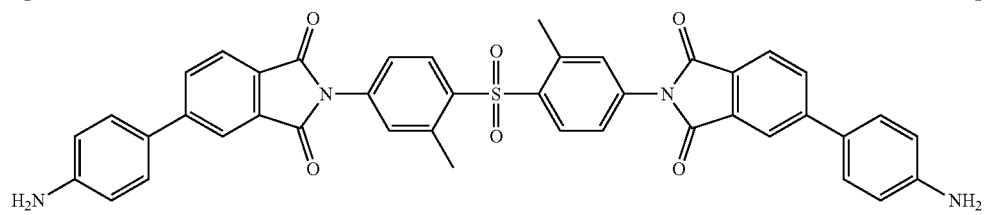
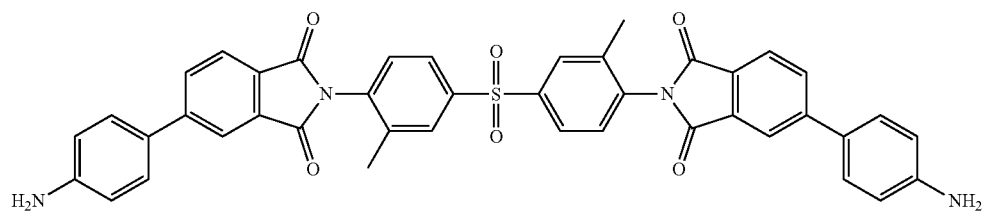
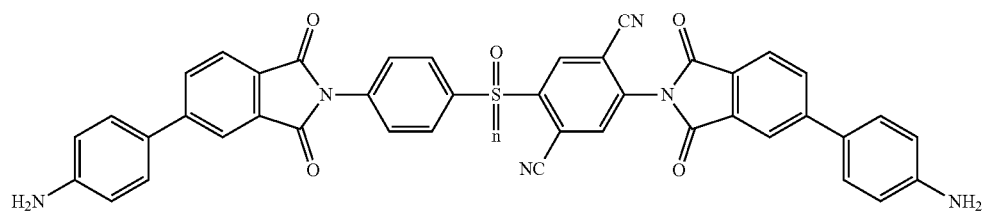

-continued
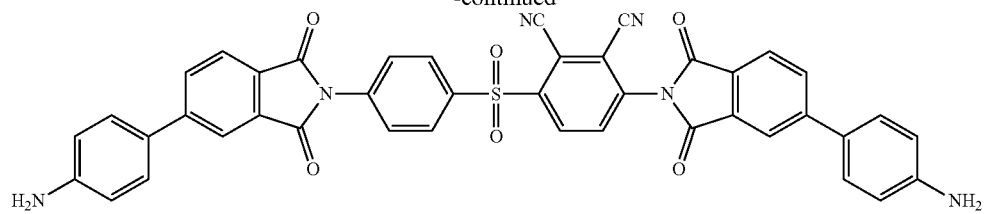
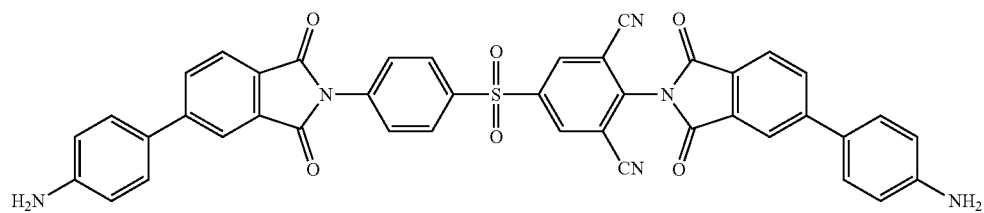
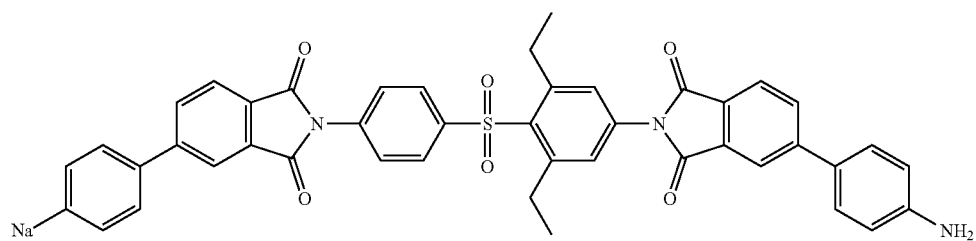
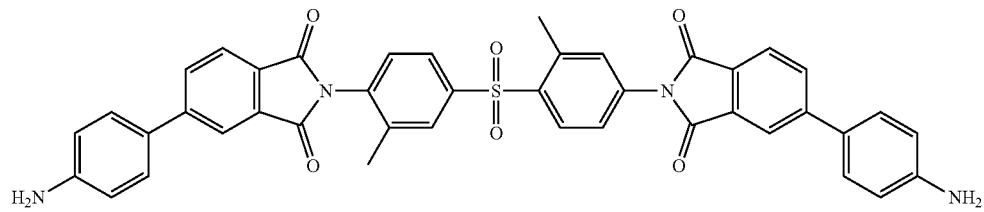
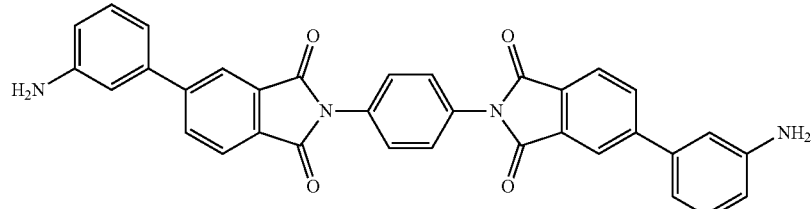
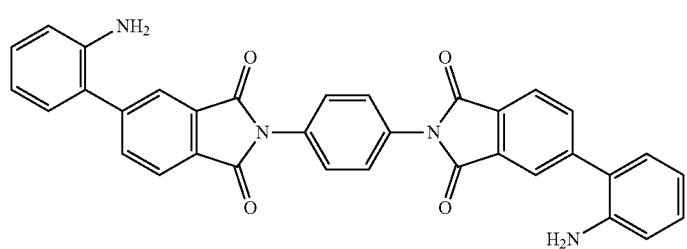
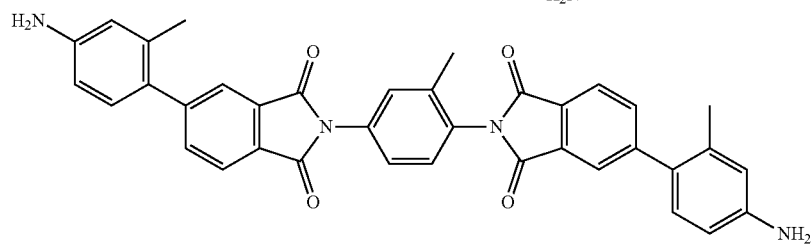

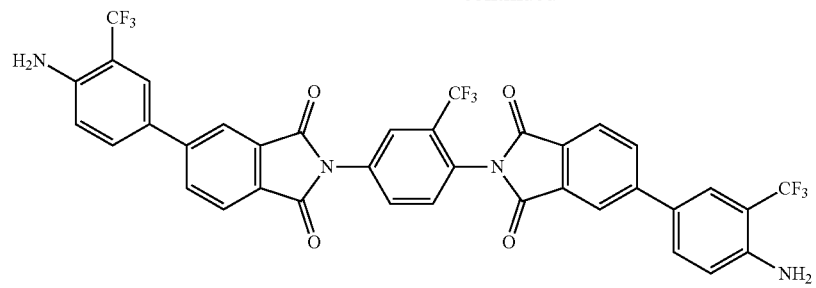
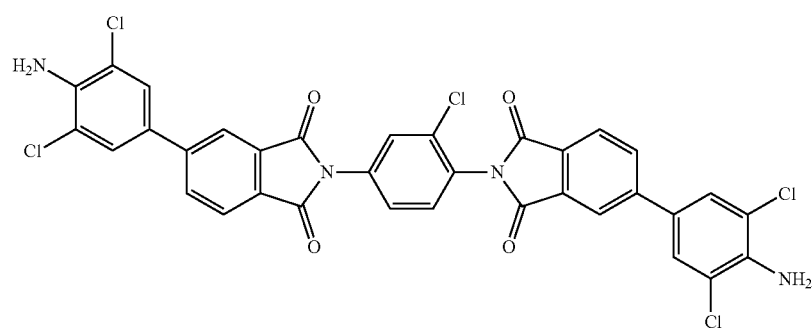
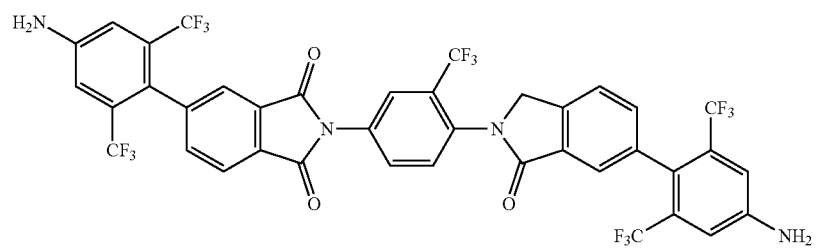
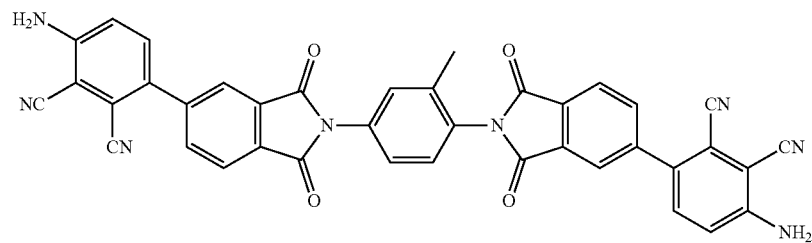
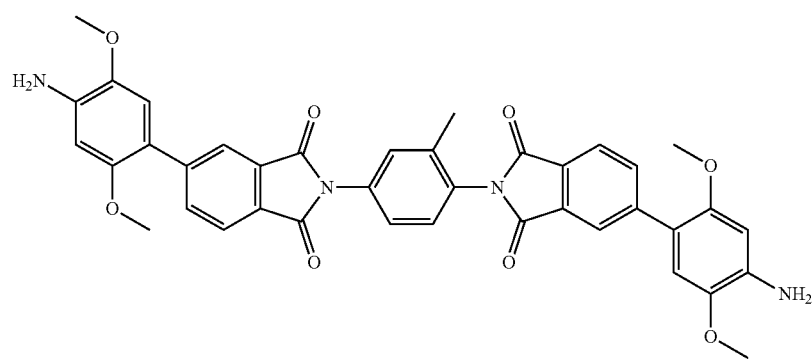

-continued
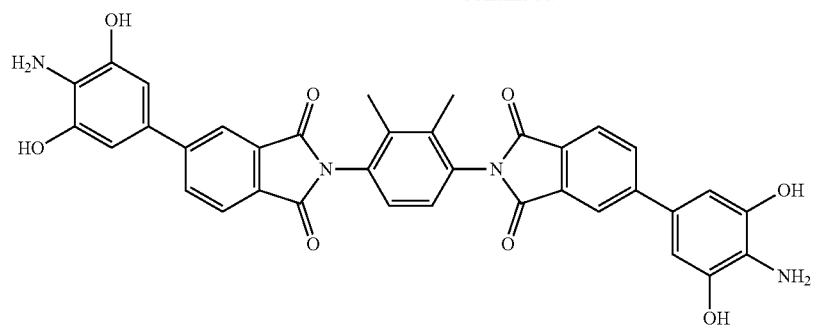
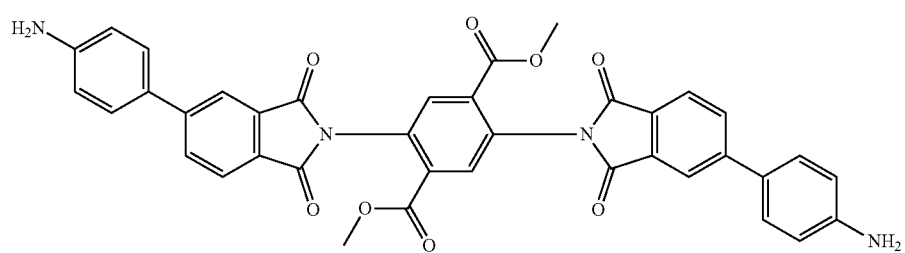
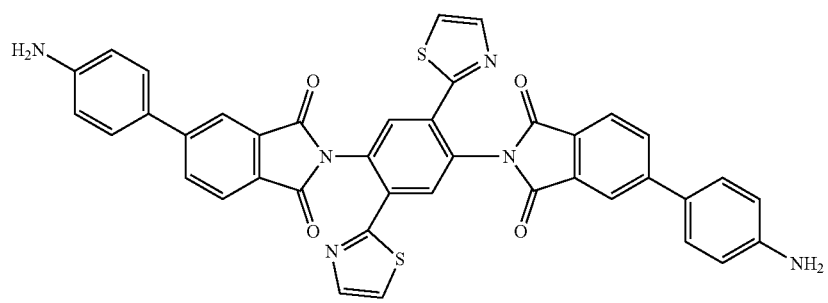 [SMILES: Nc1ccc(-c2ccc3c(c2)C(=O)N(c2cc(-c4nccs4)c(N4C(=O)c5ccc(-c6ccc(N)cc6)cc5C4=O)cc2-c2nccs2)C3=O)cc1]
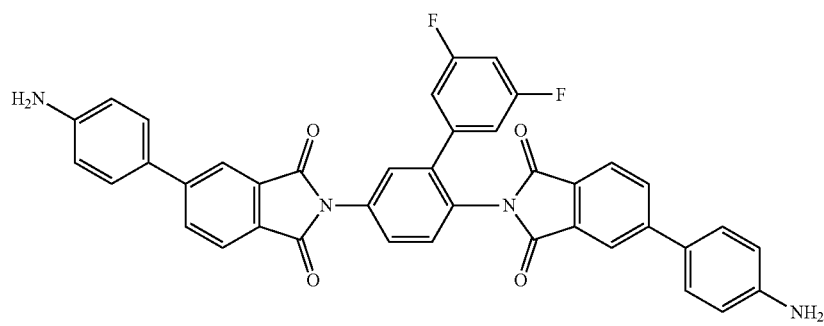
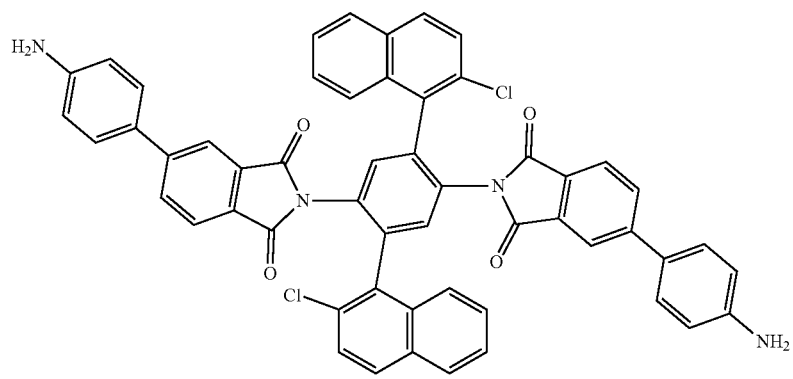

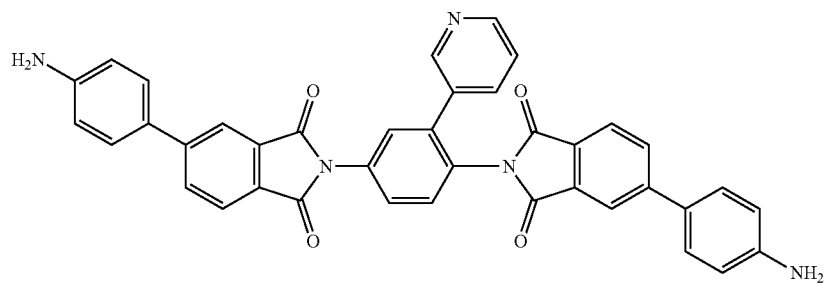
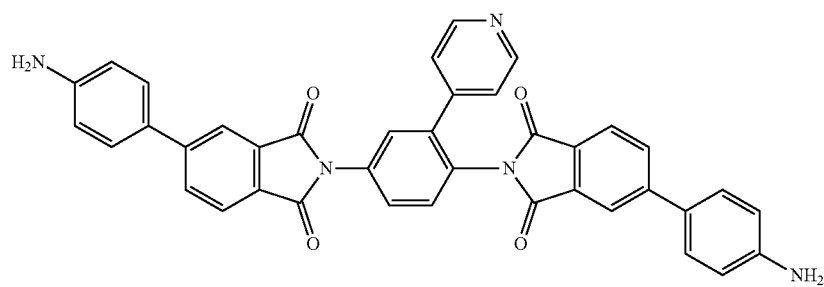
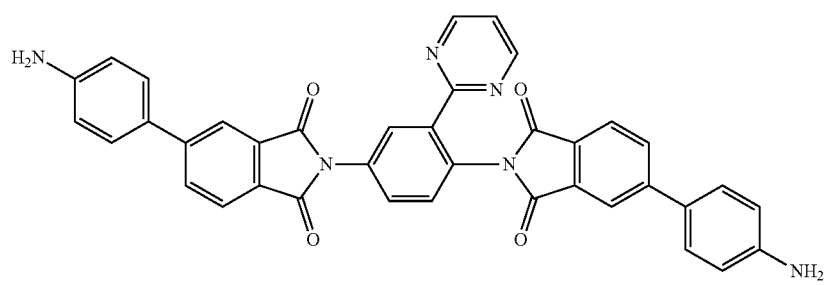
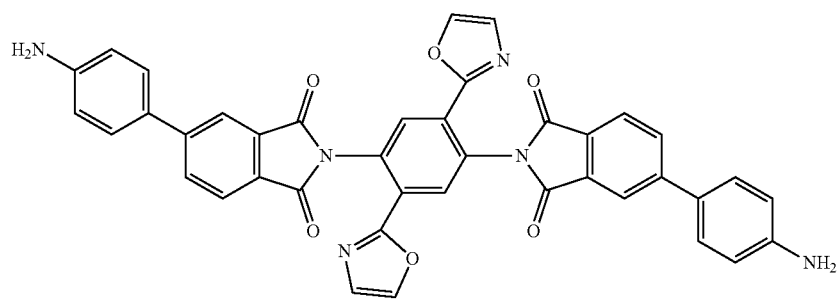
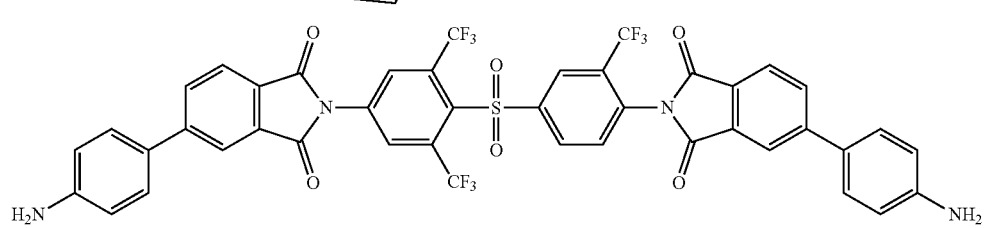
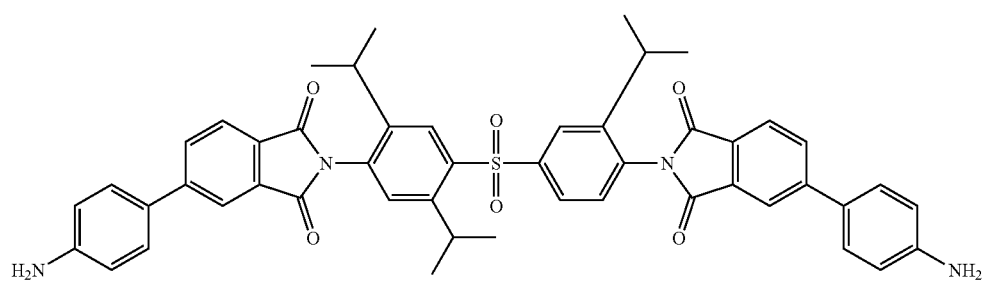

-continued
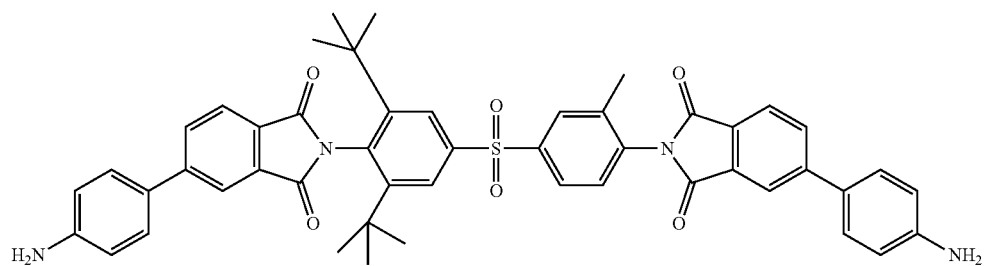
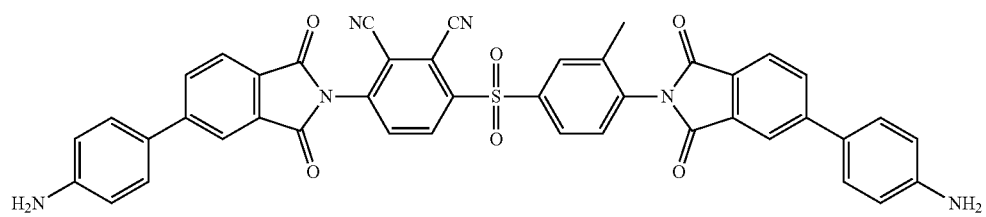
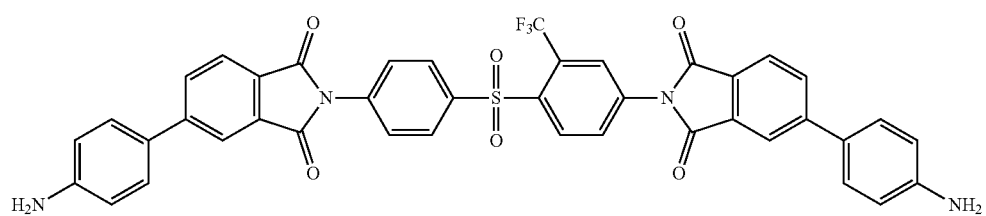
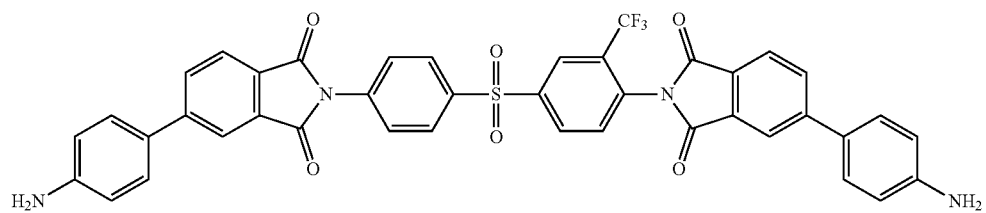
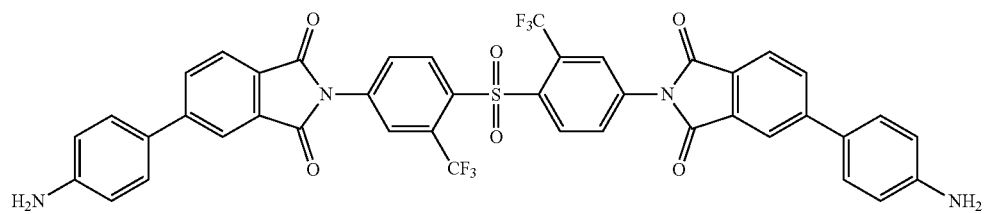
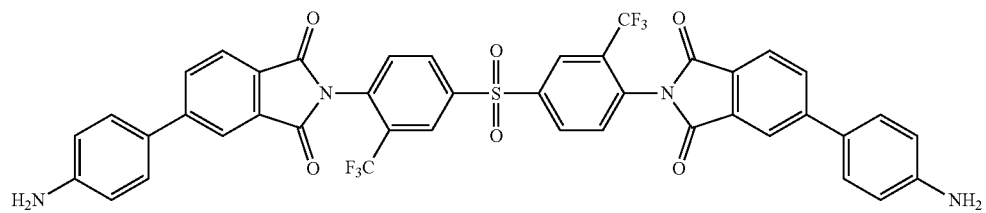
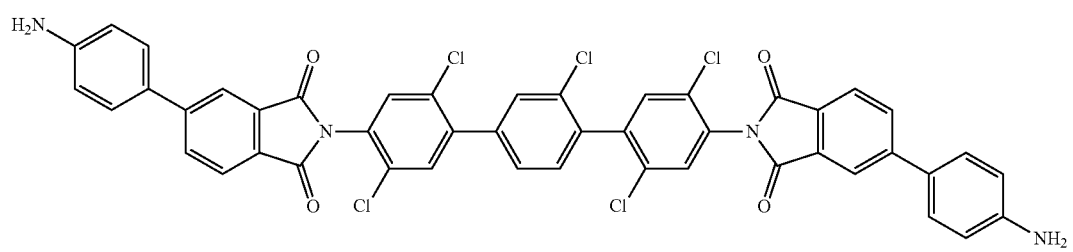

-continued
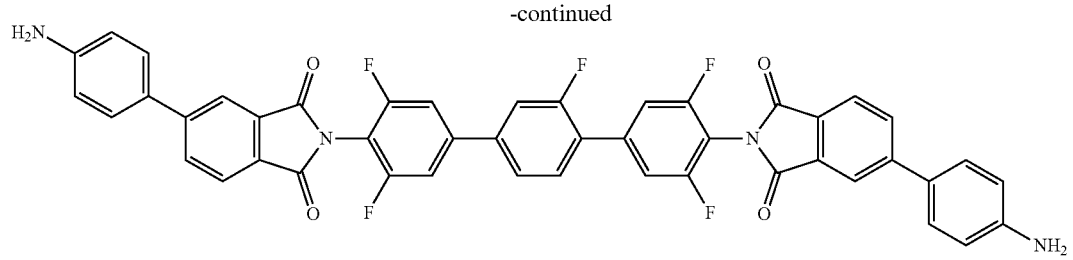
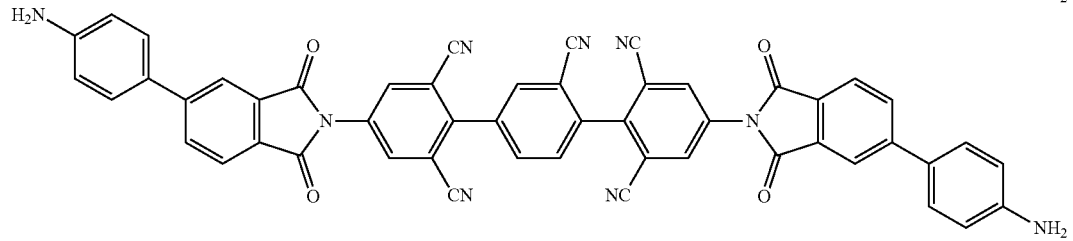
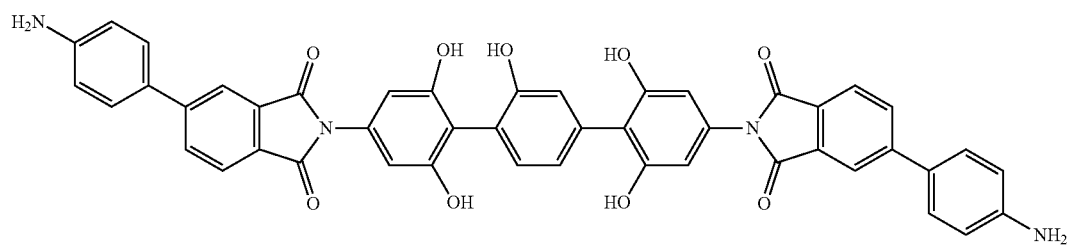
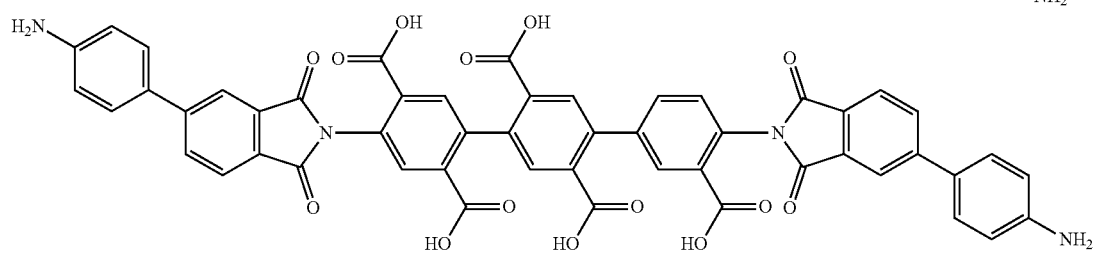
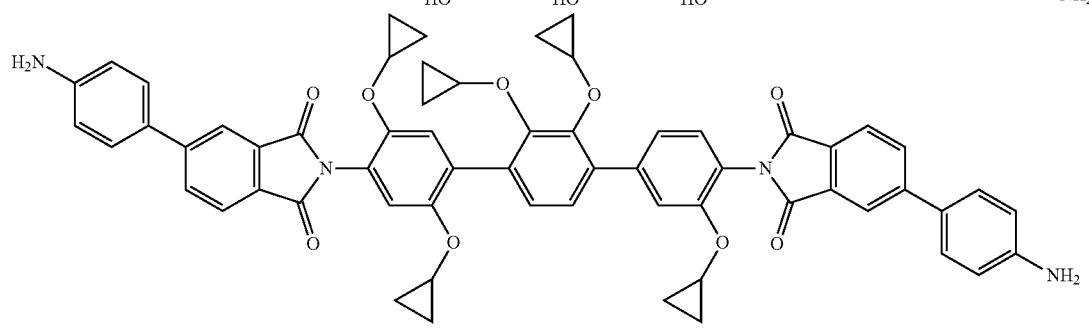
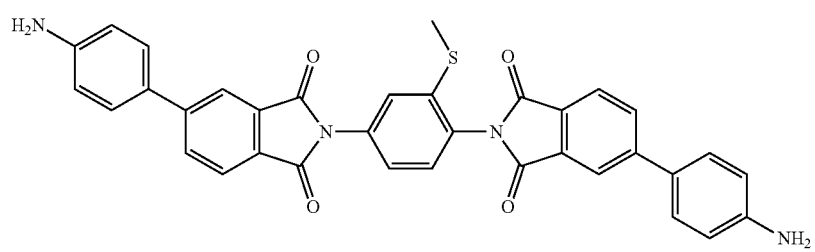

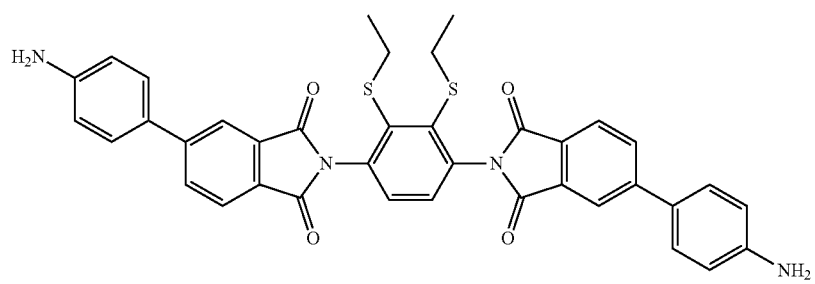
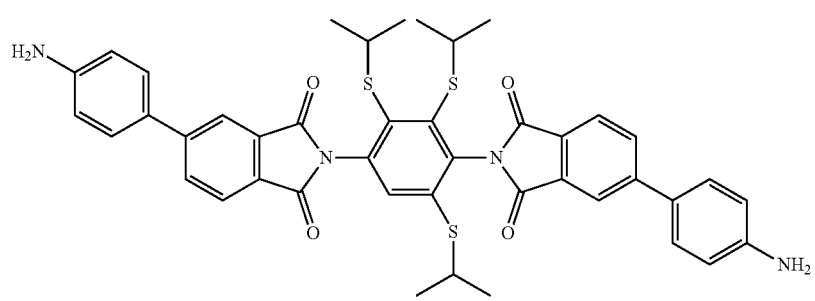
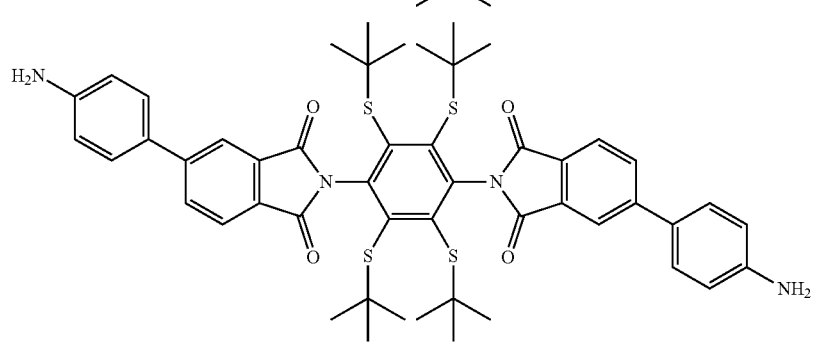
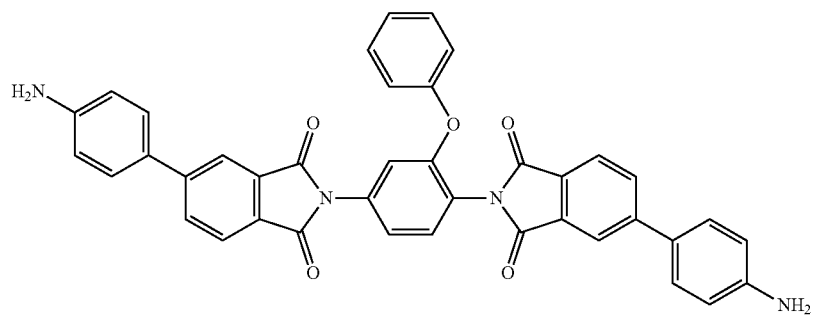
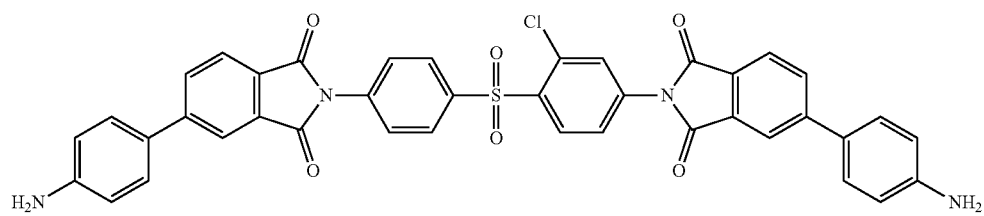
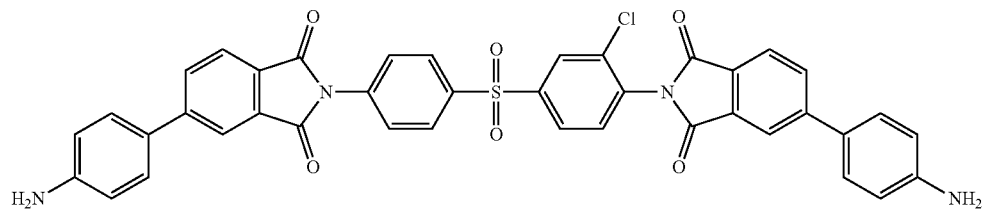

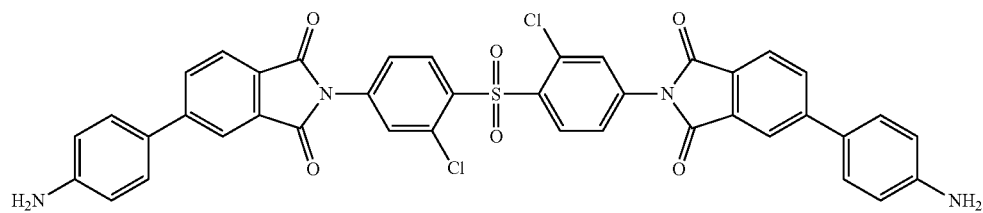
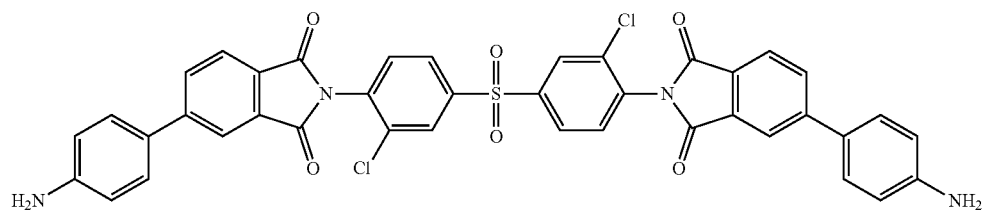
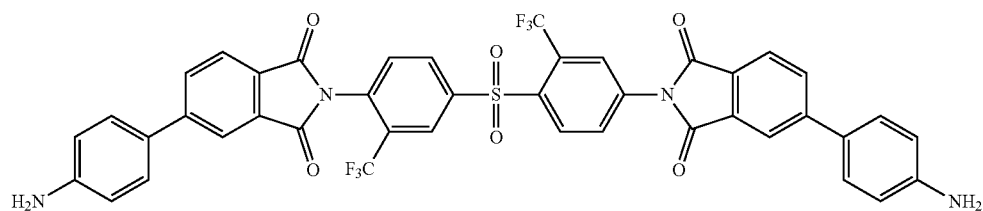
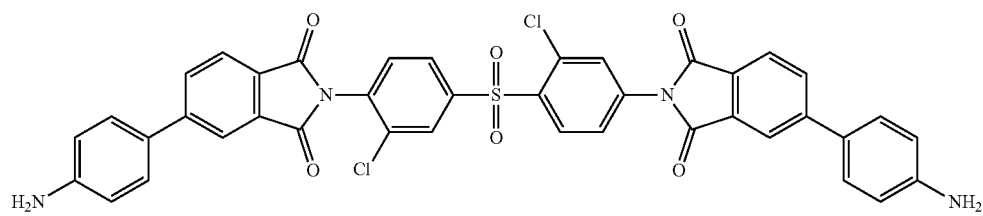
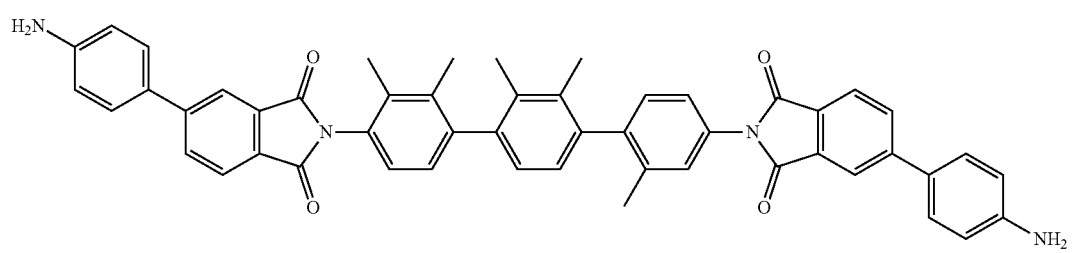
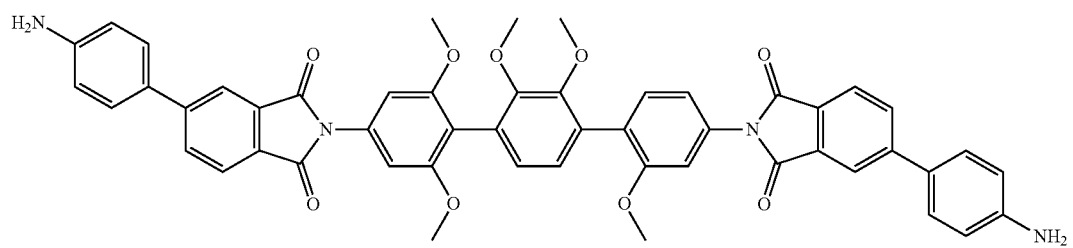
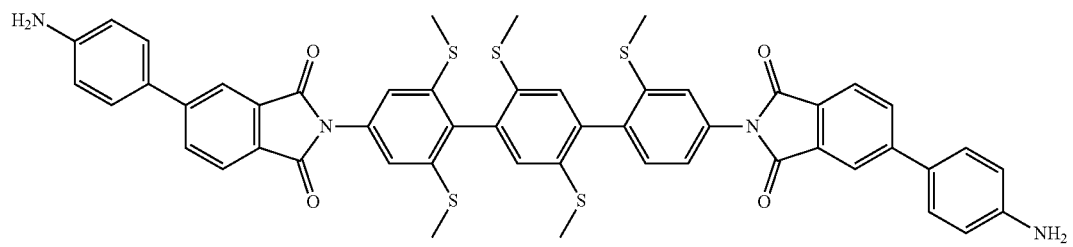

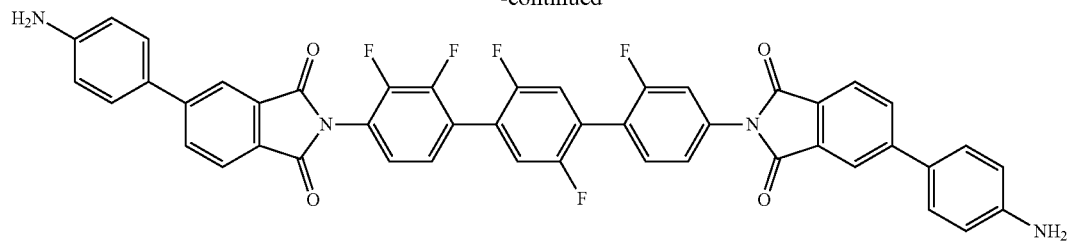
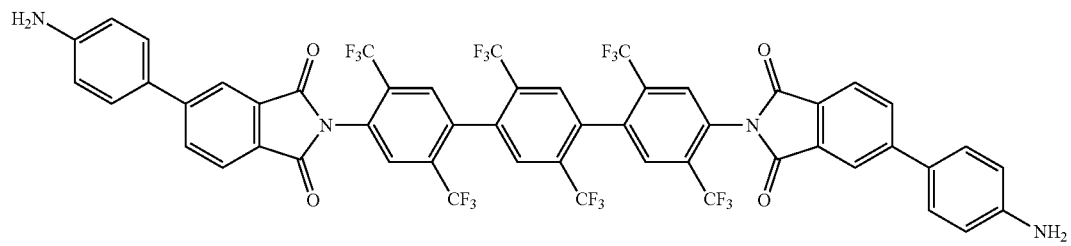
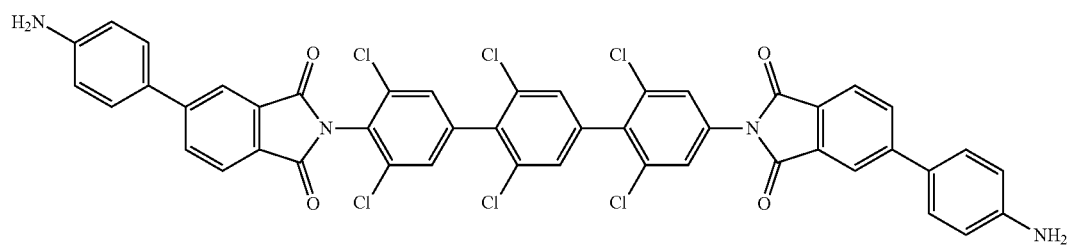
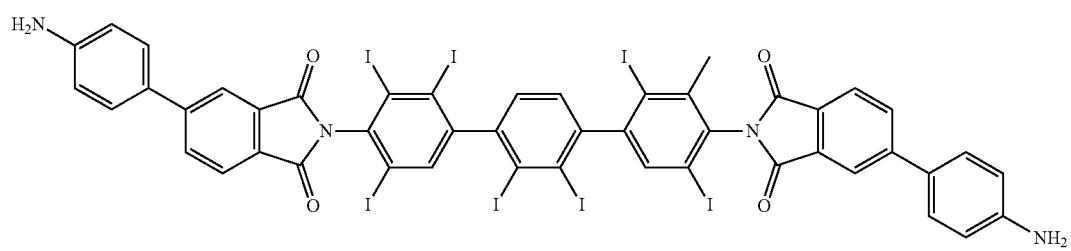
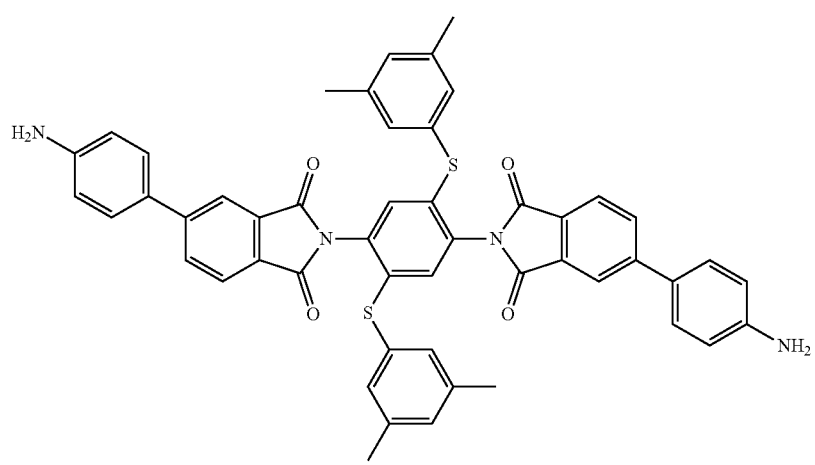

-continued
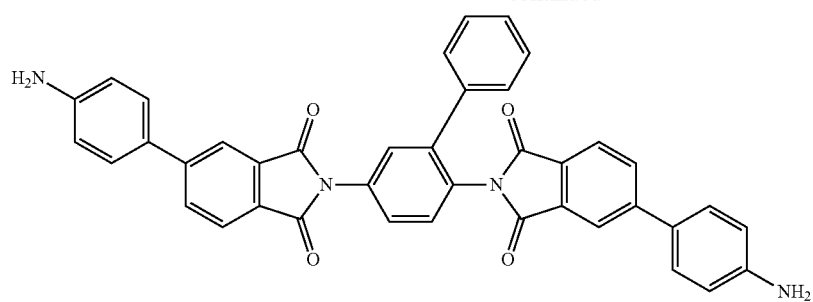
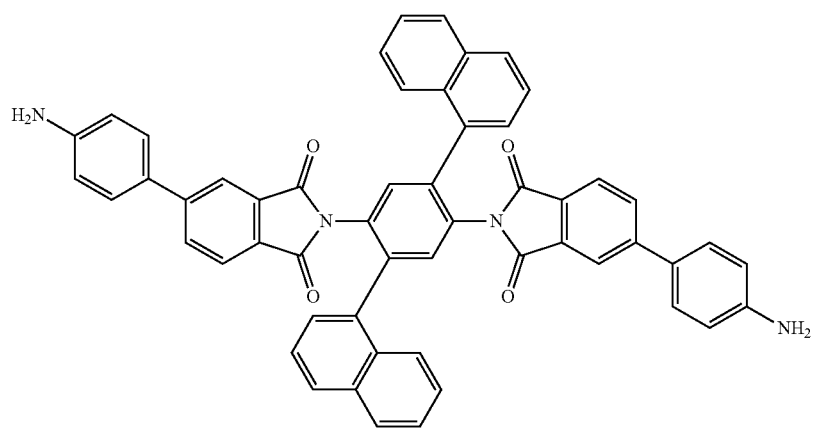
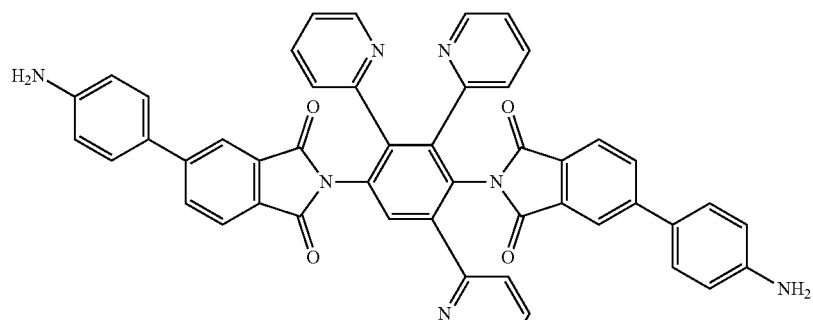
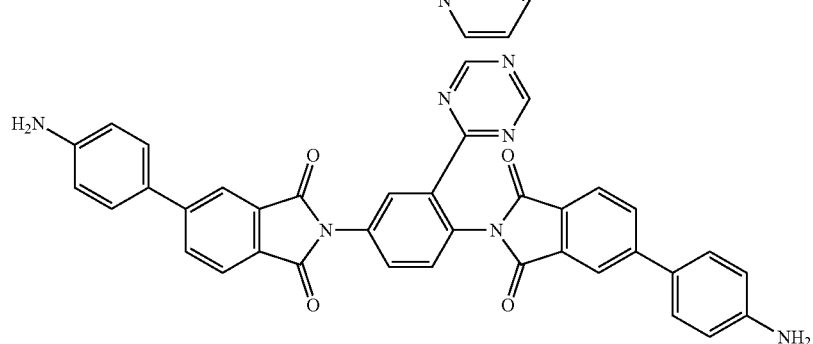
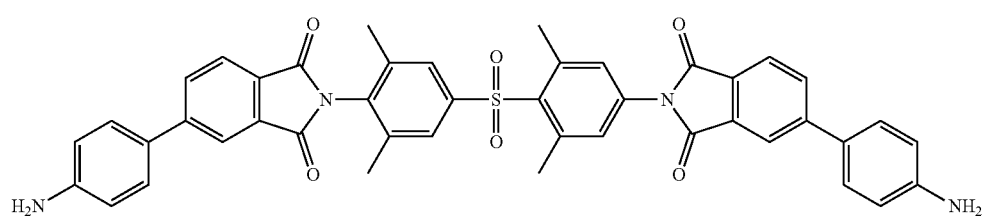

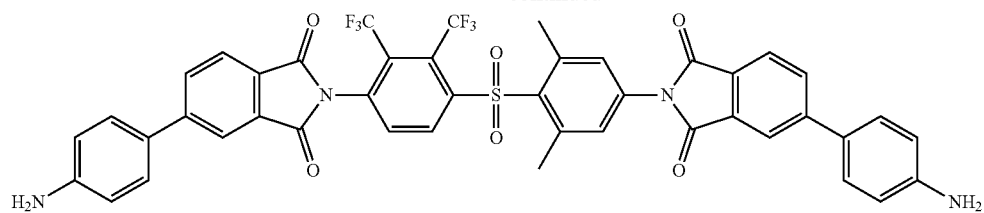
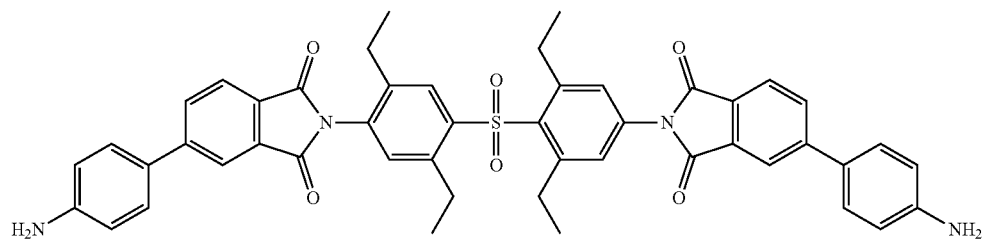
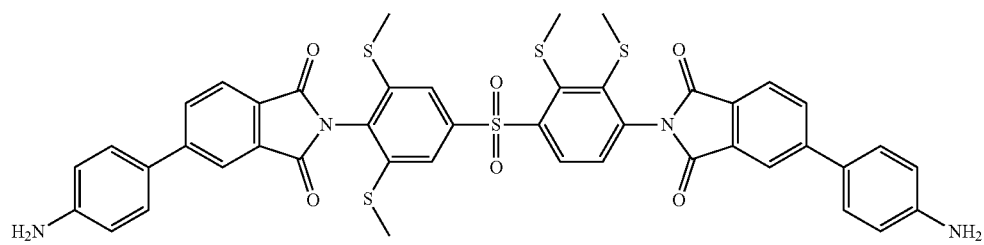
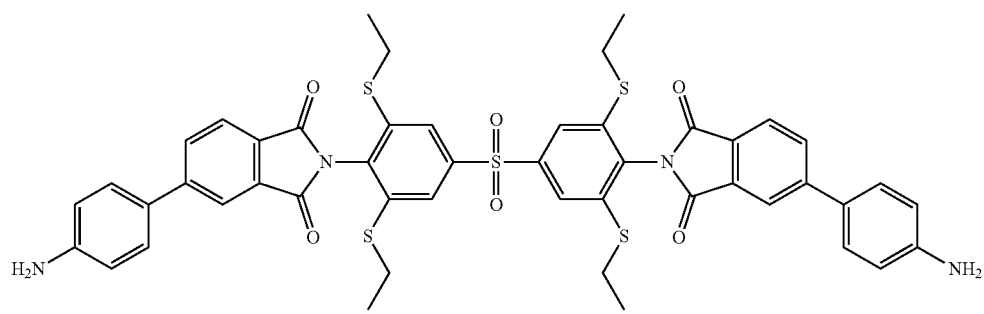
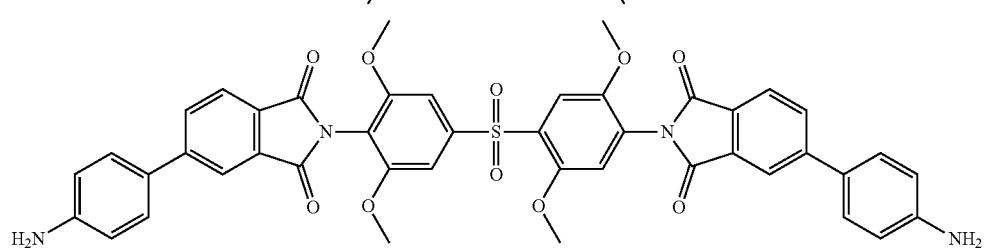
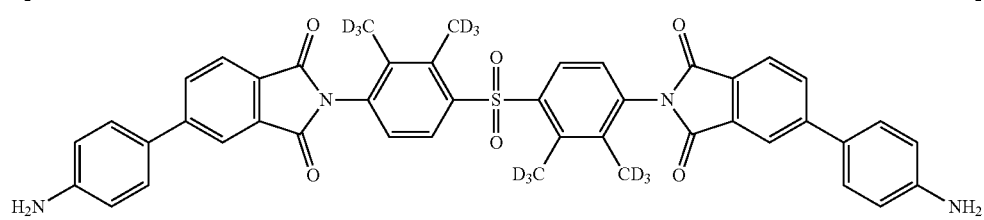
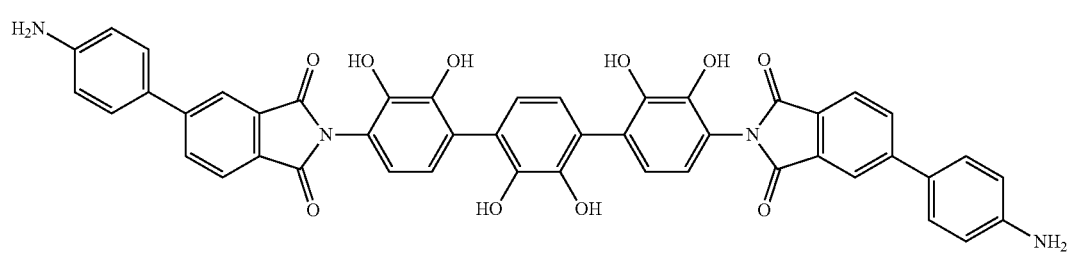

-continued
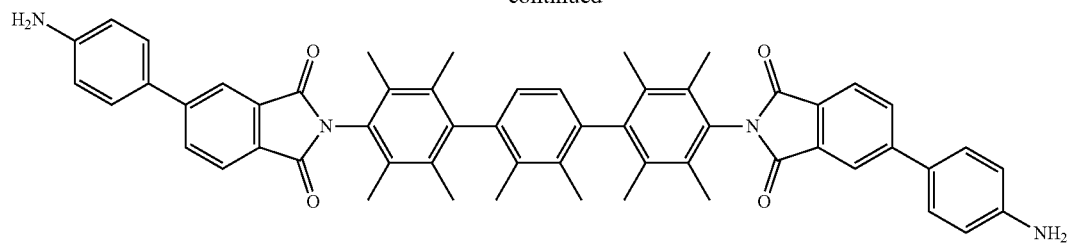
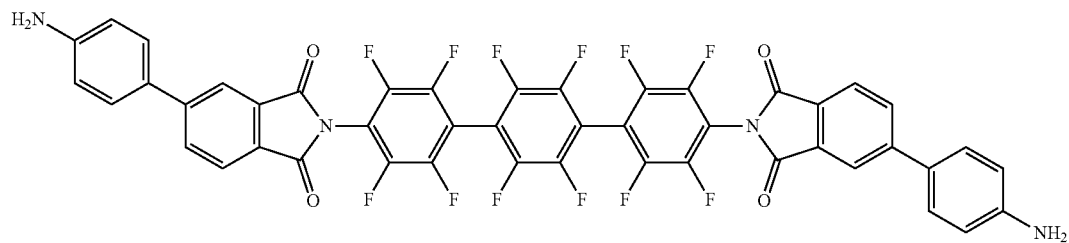
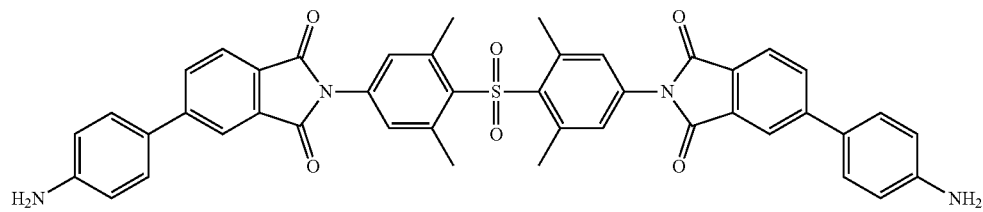
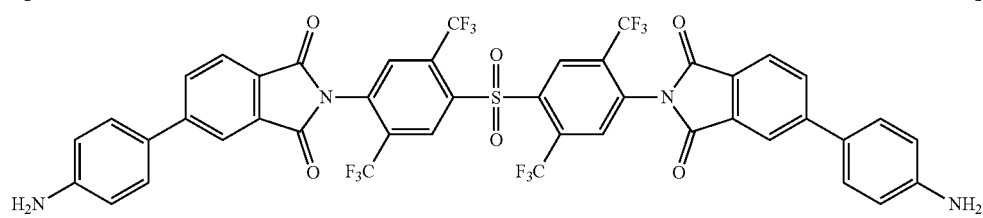
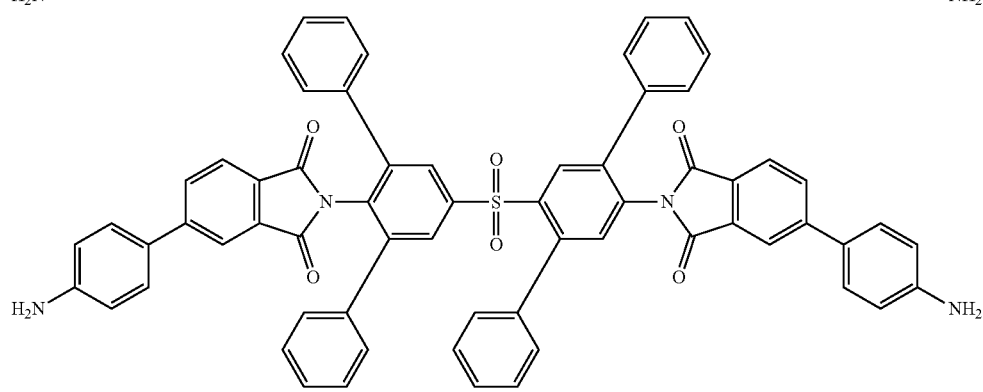
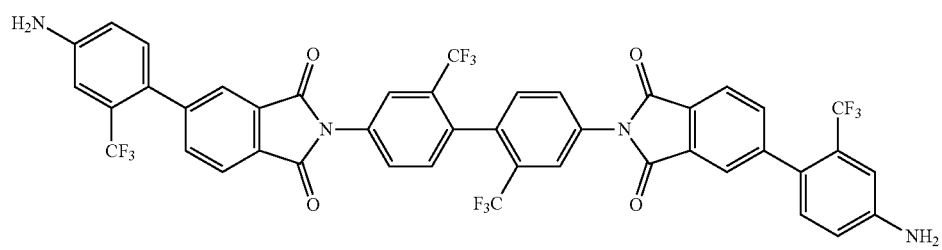

-continued
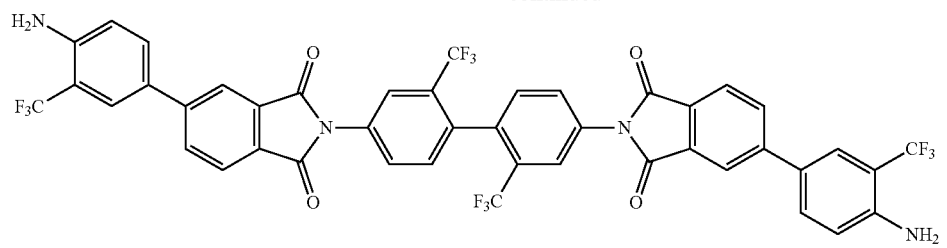
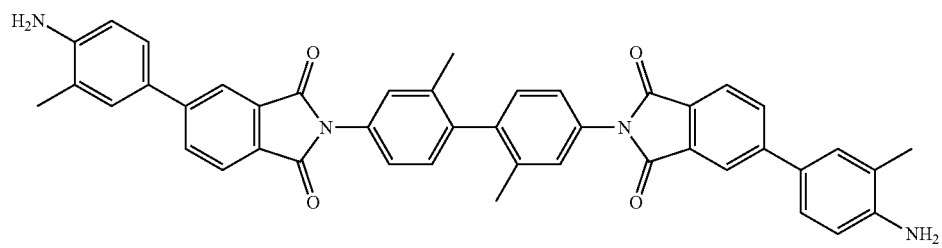
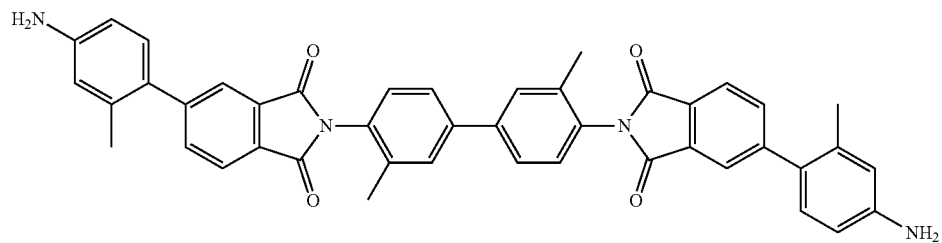
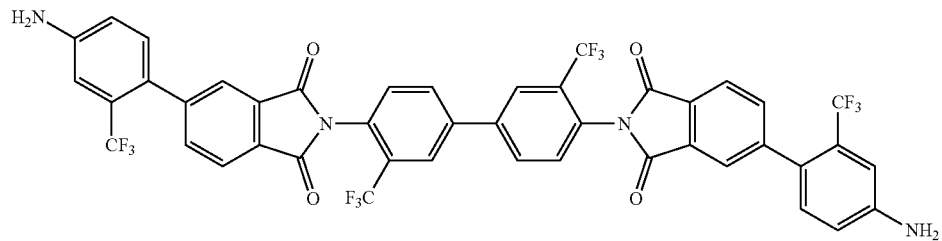
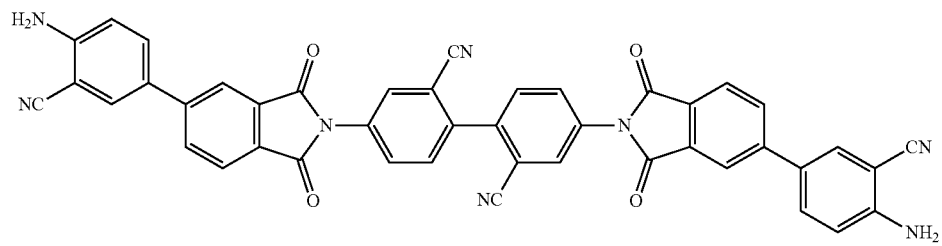
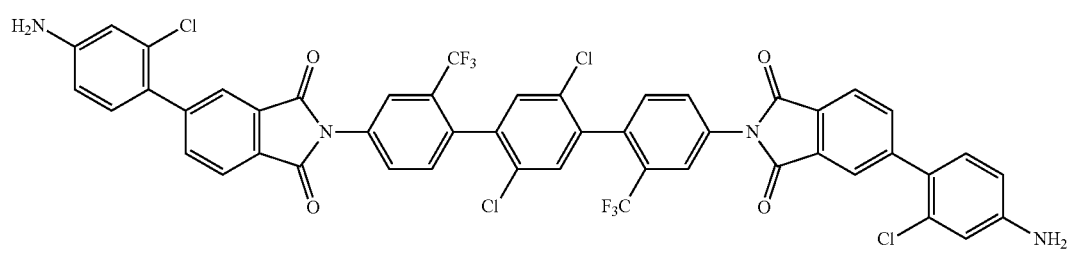
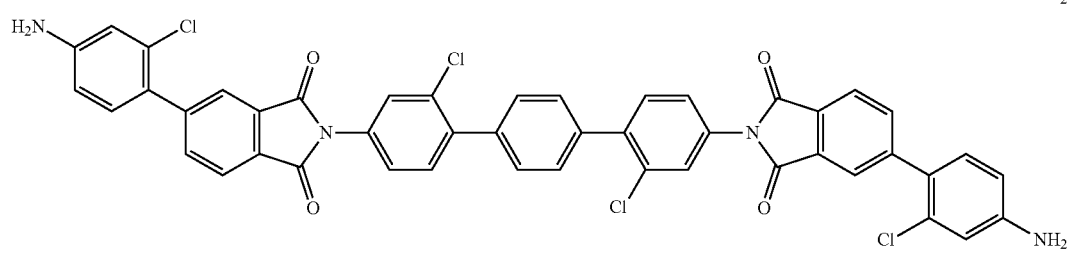

-continued
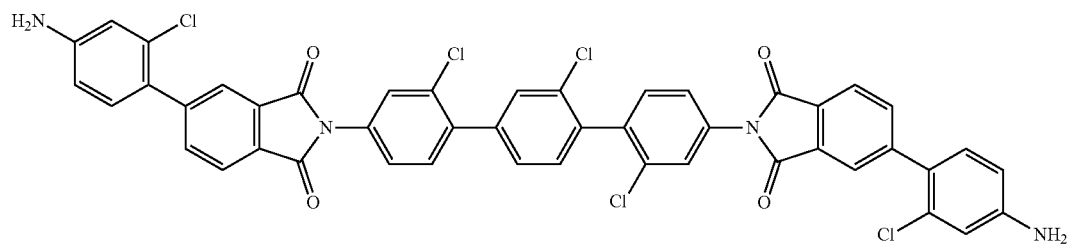
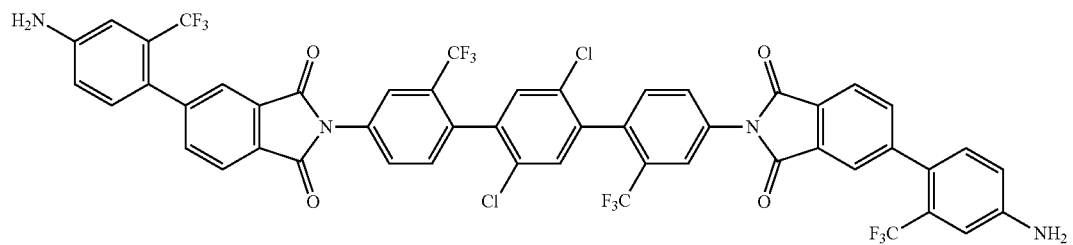
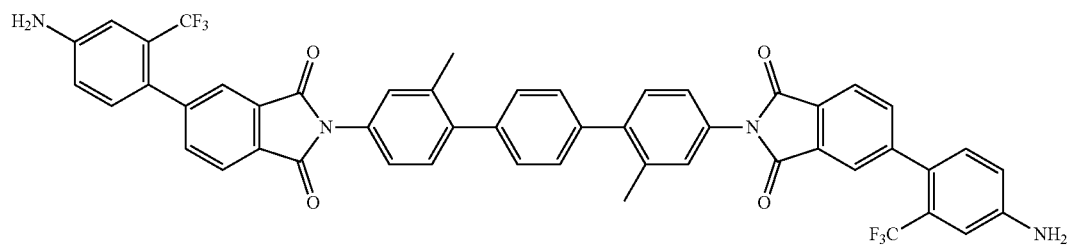
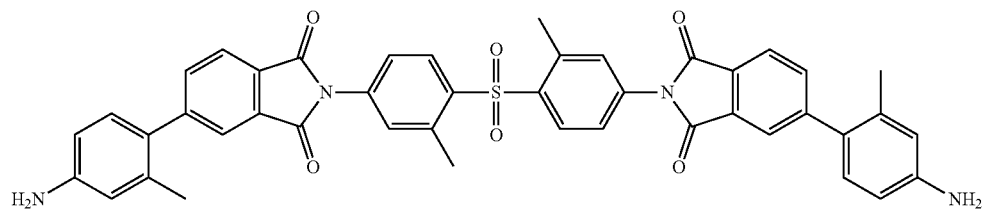
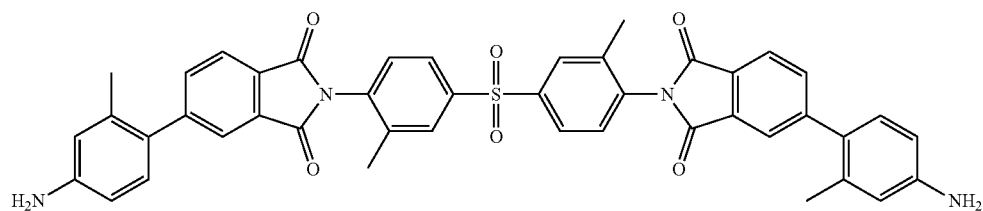
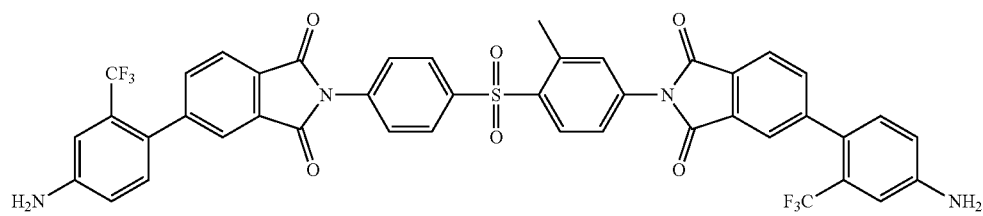
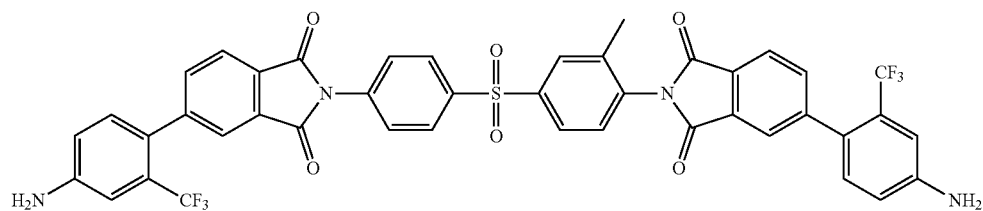

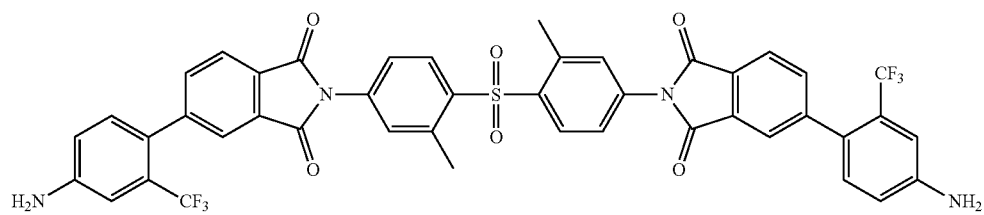
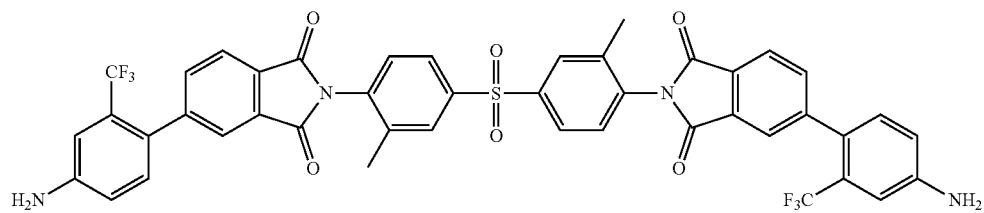
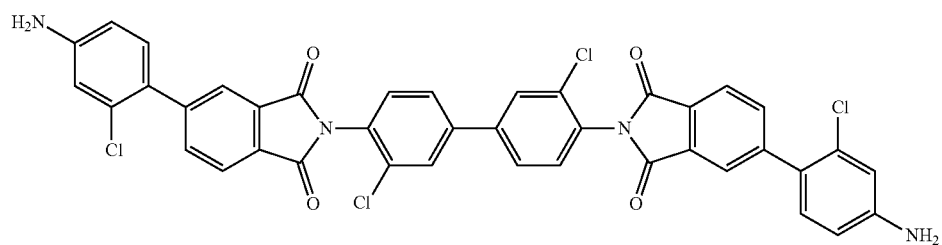
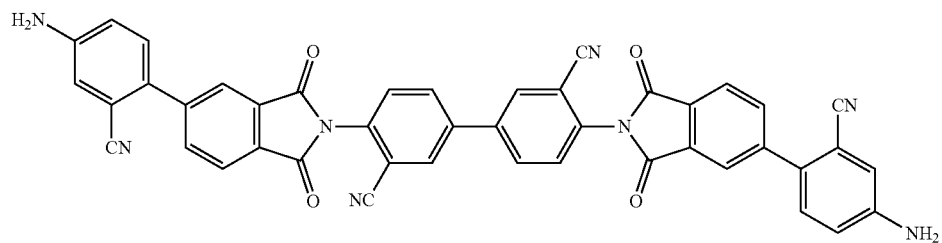
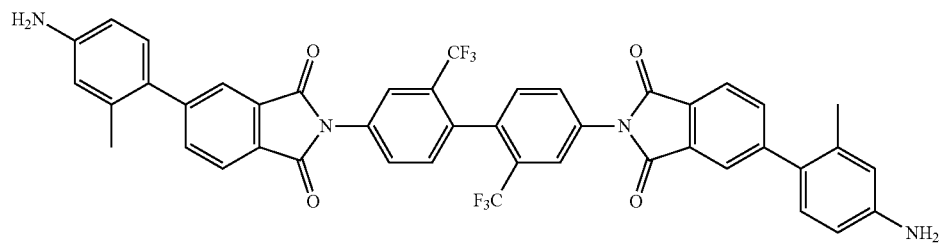
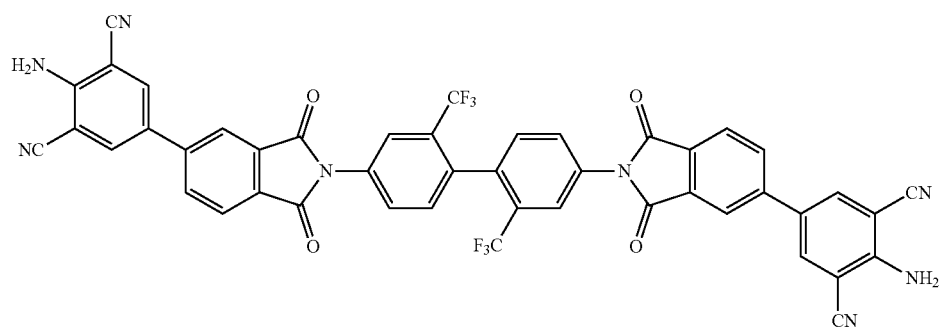

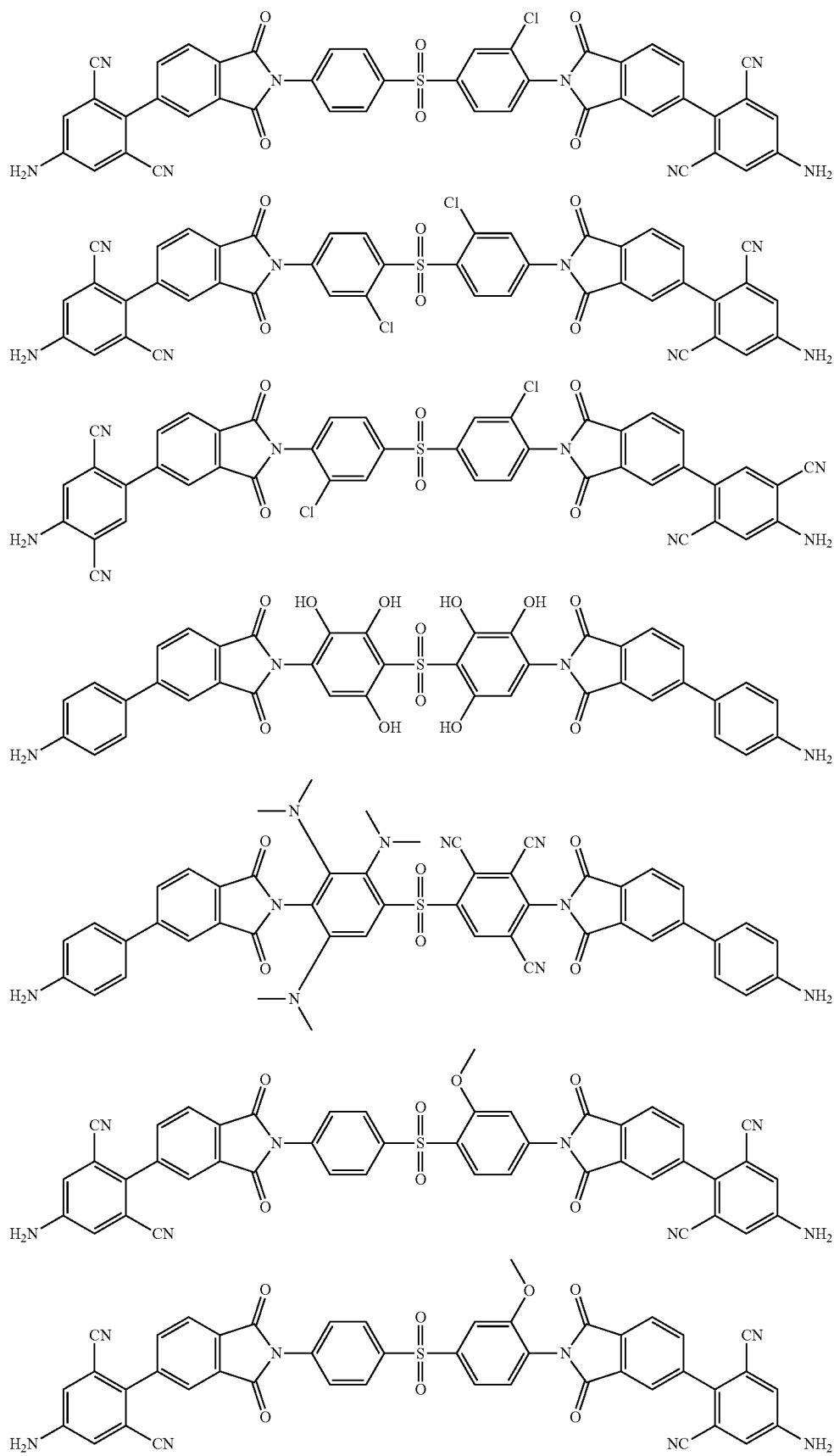

-continued
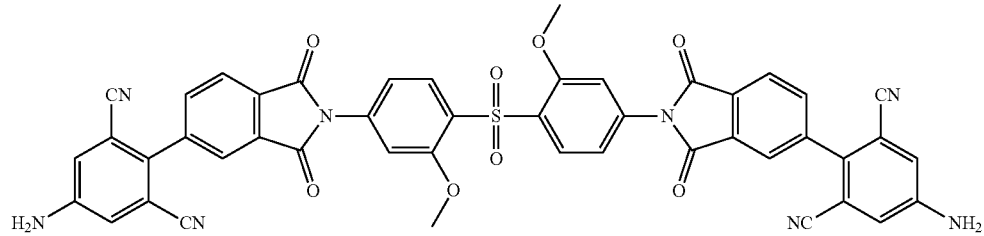
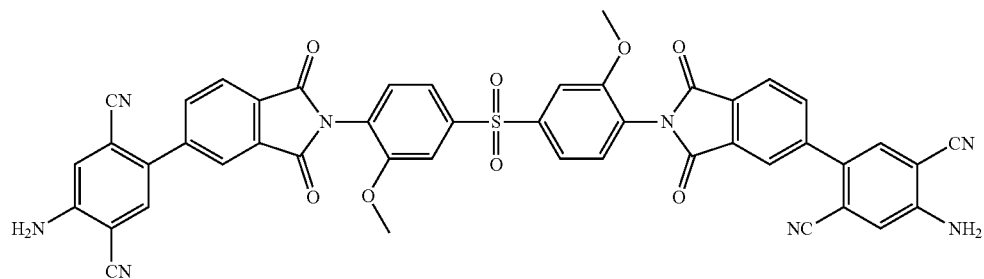
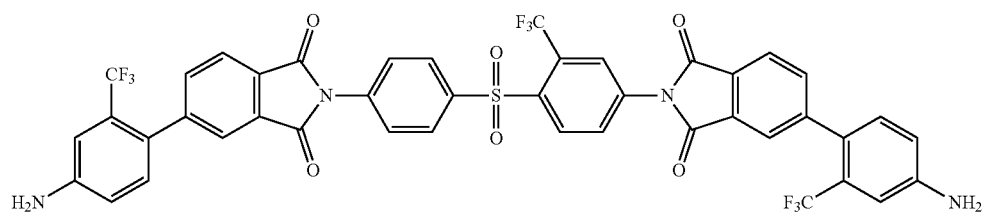
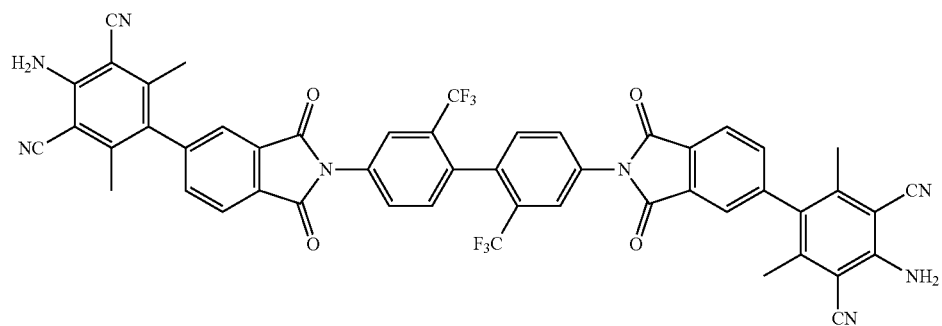
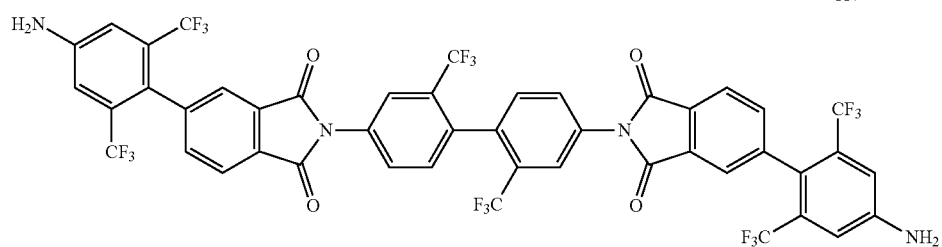
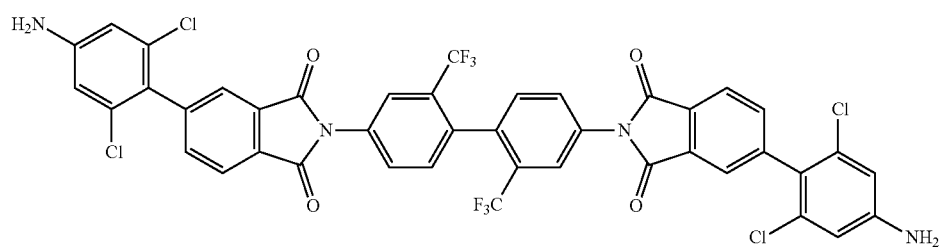

-continued
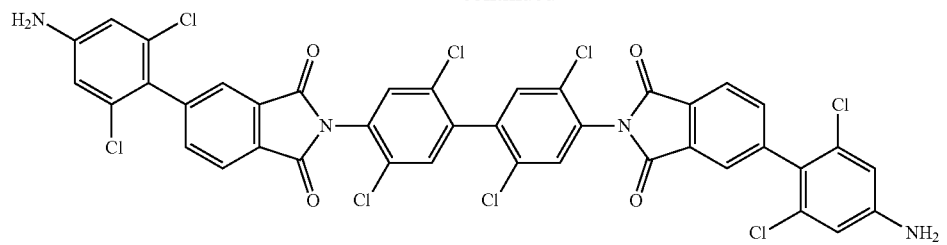
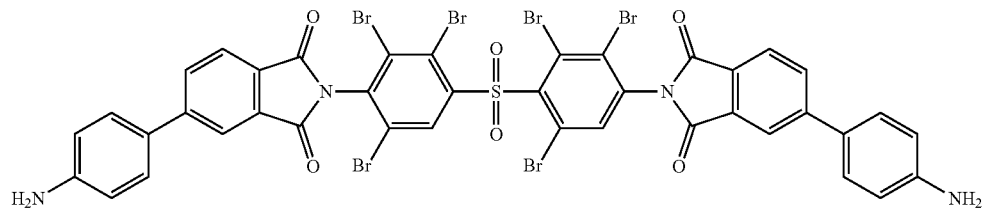
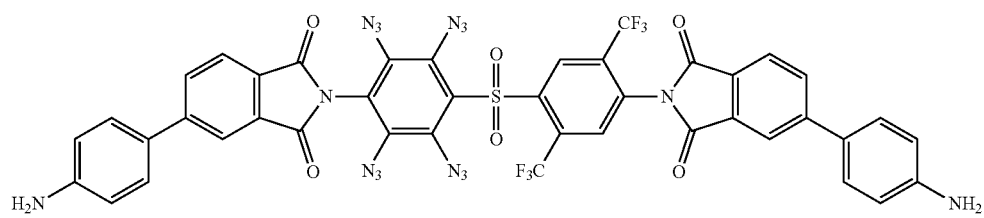
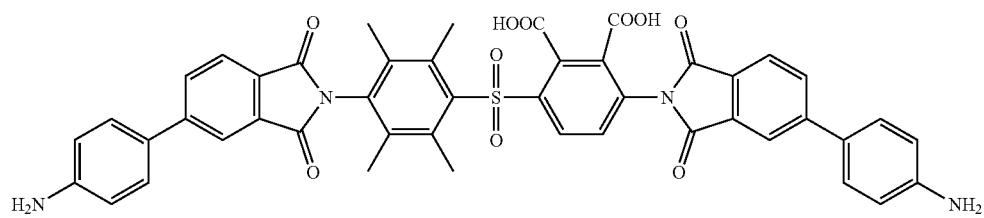
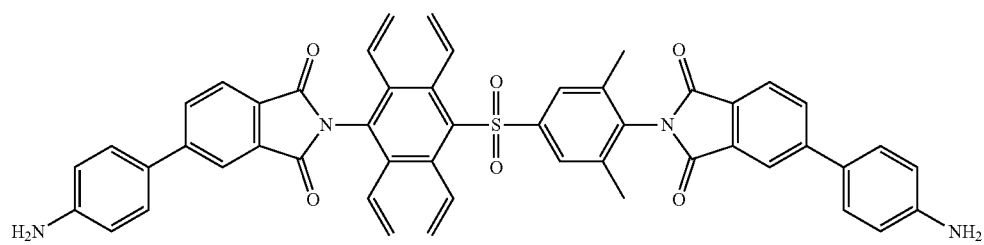
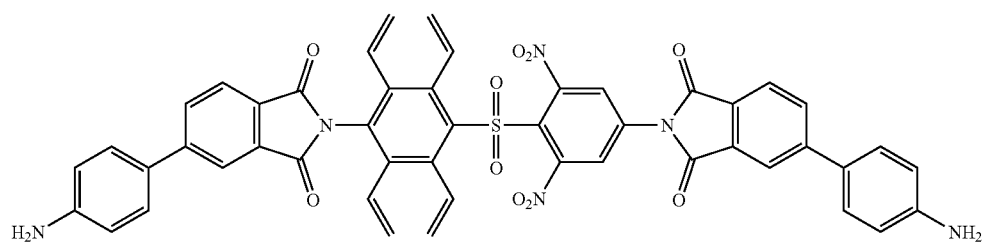
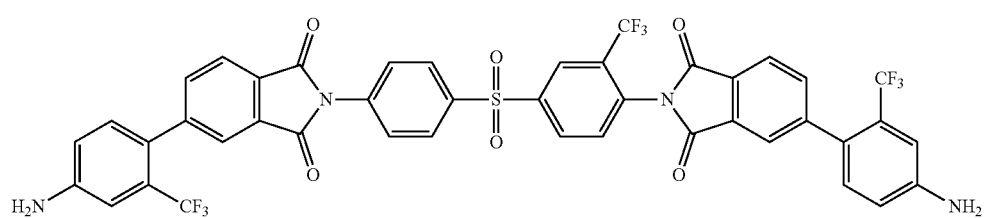

-continued
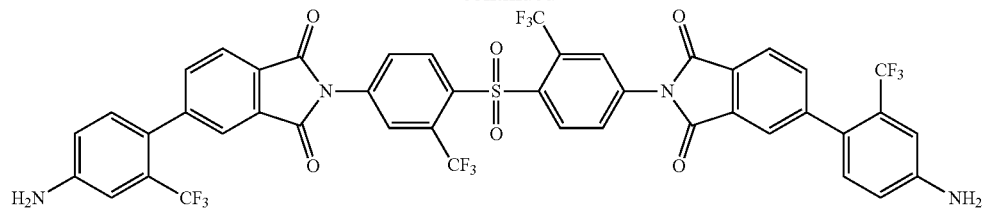
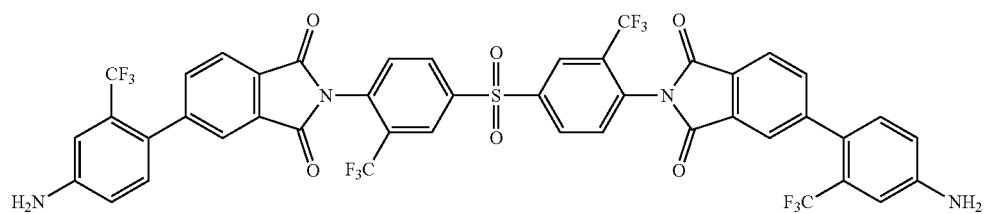
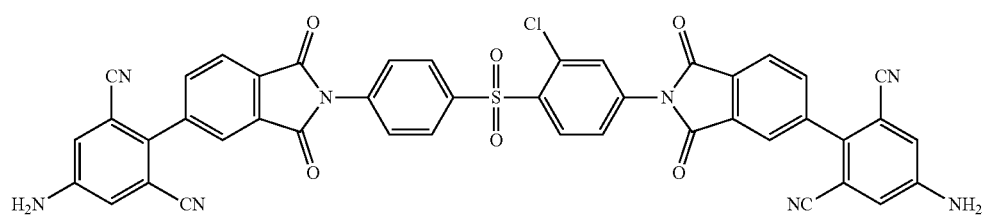
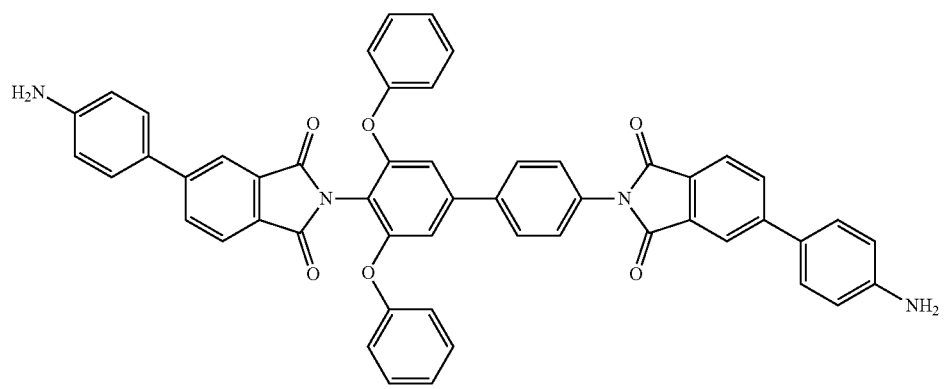
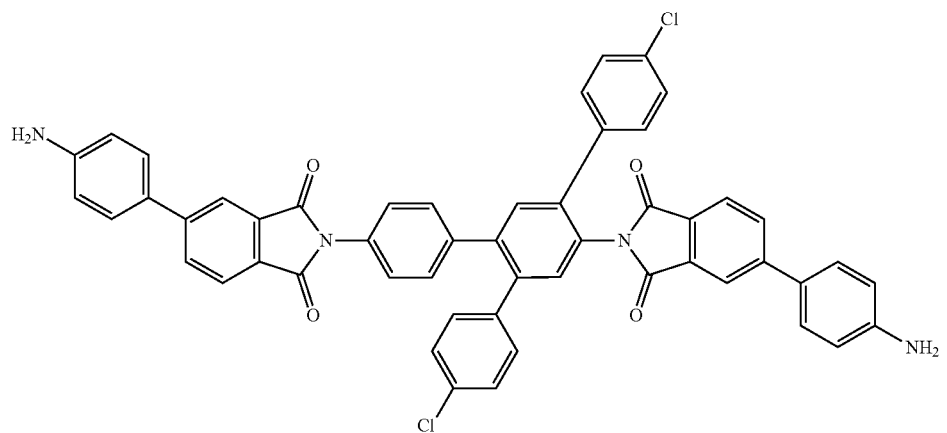

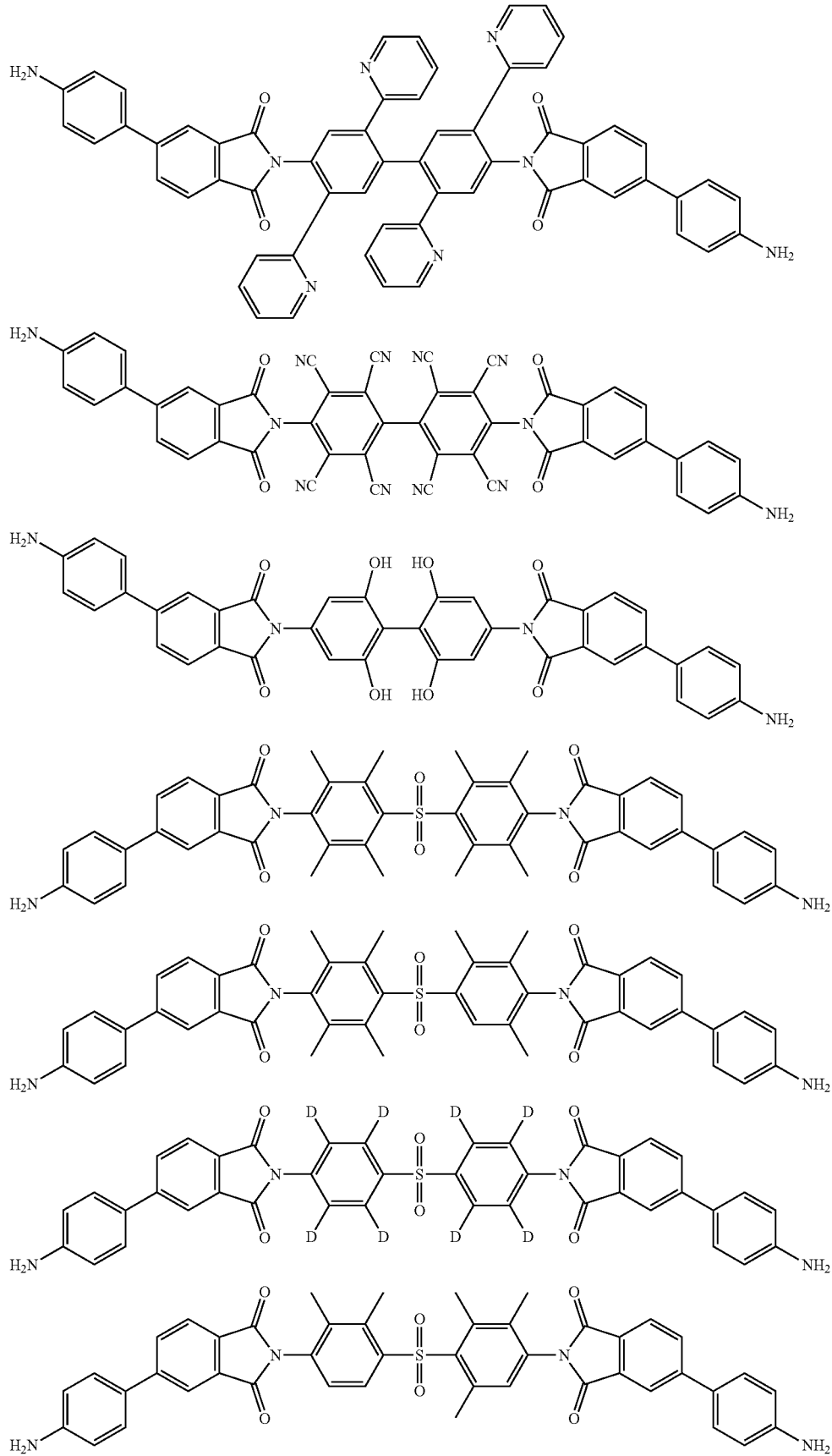

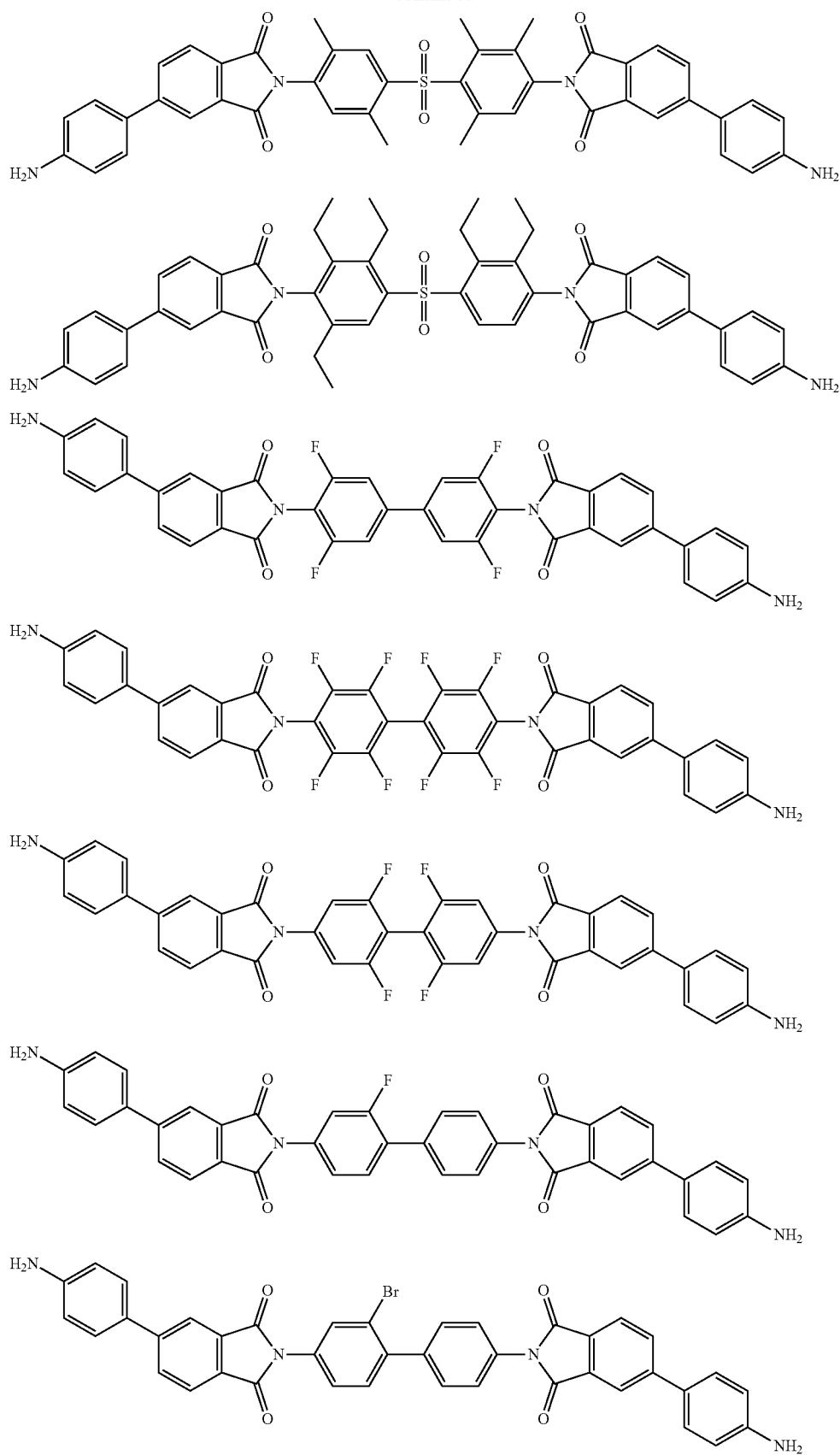

-continued
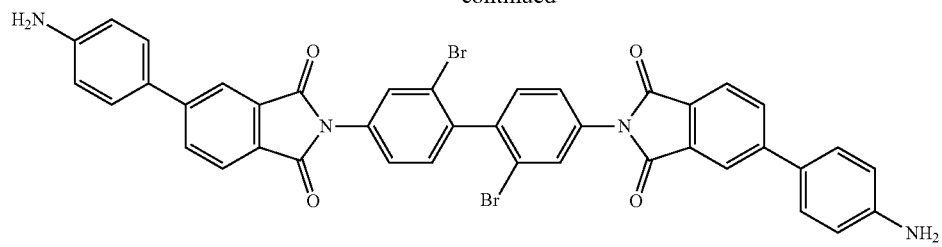
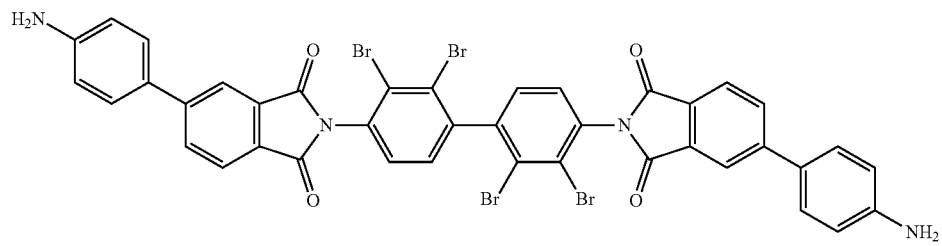
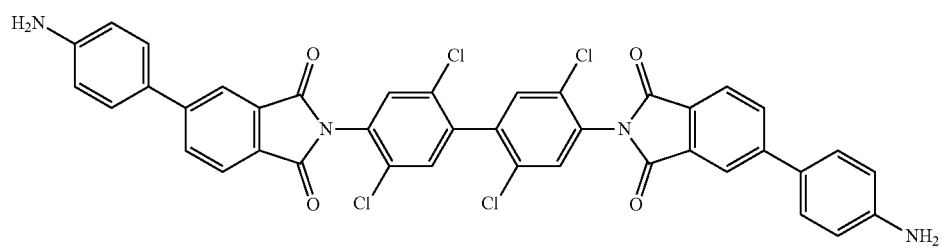
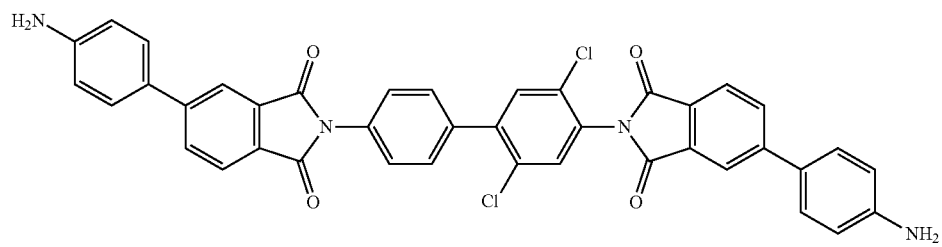
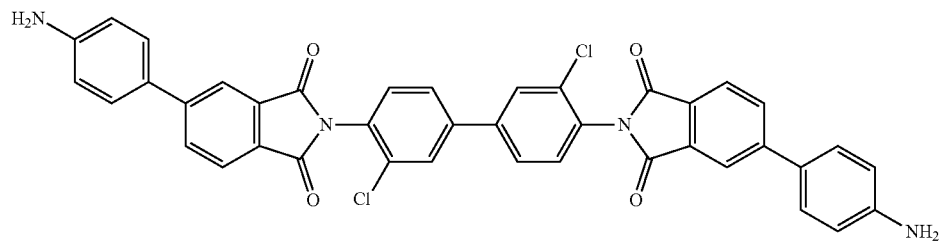
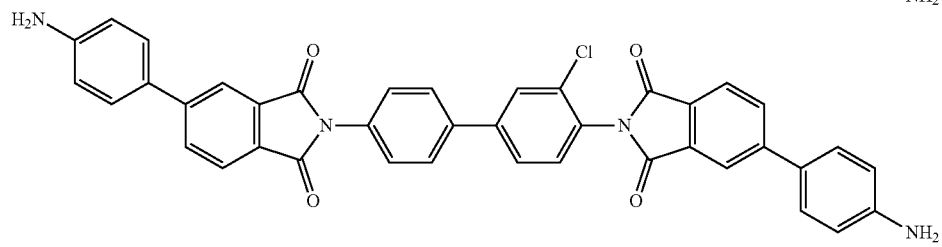

-continued
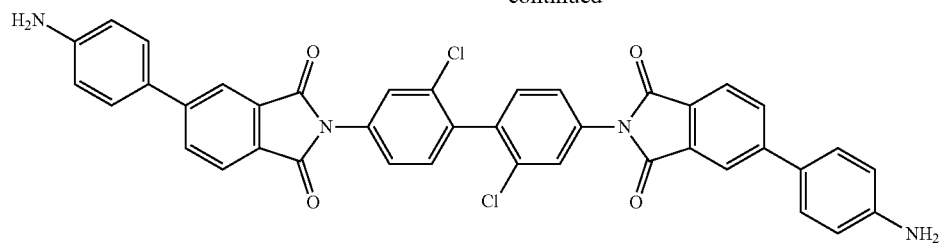
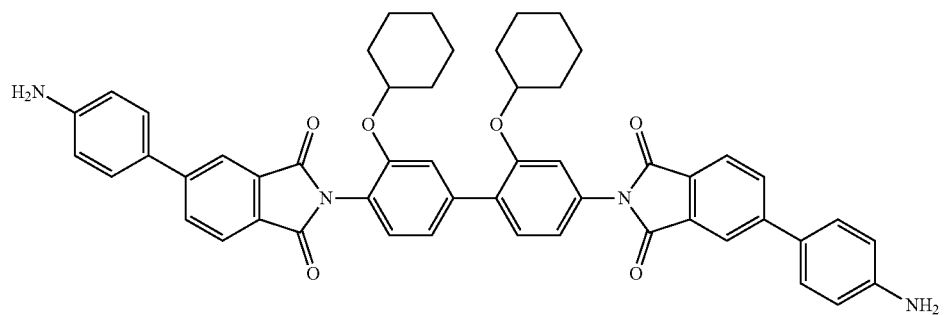
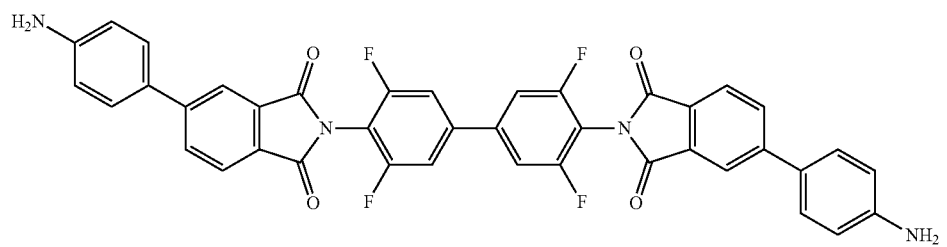
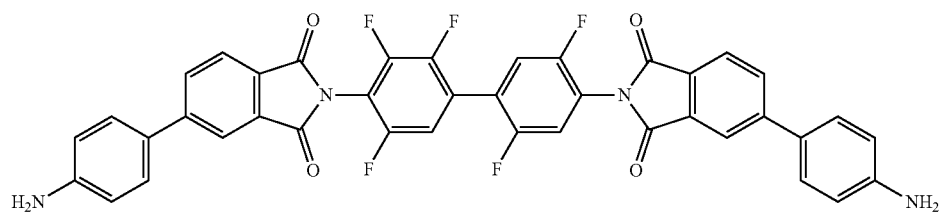
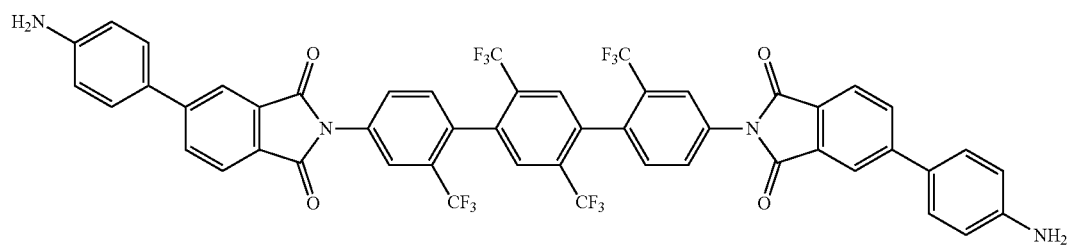
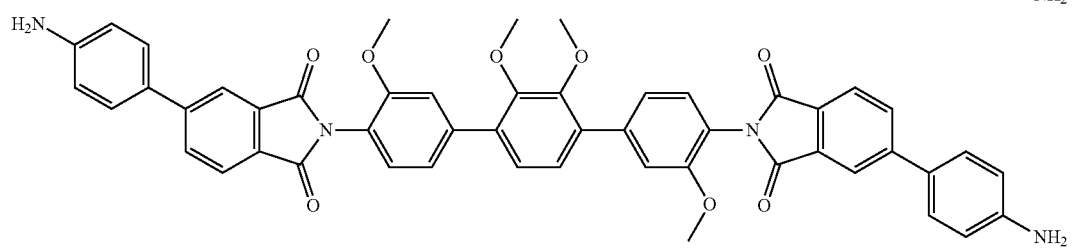

-continued
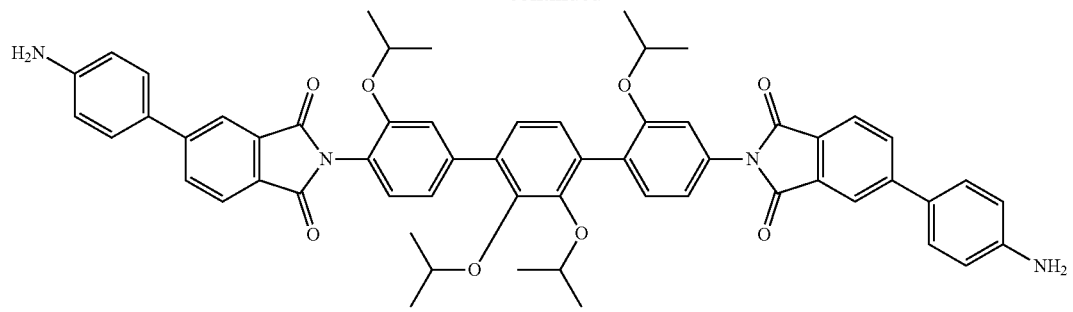
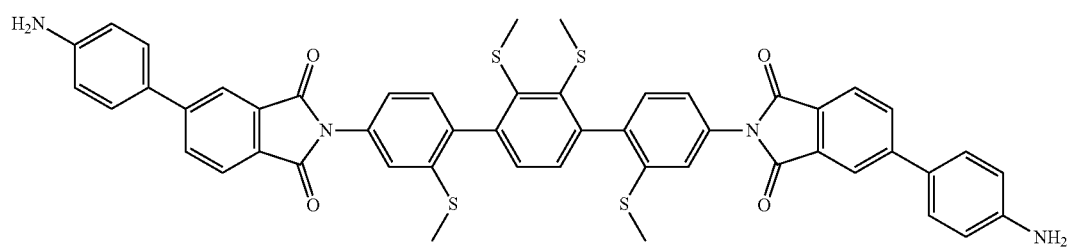
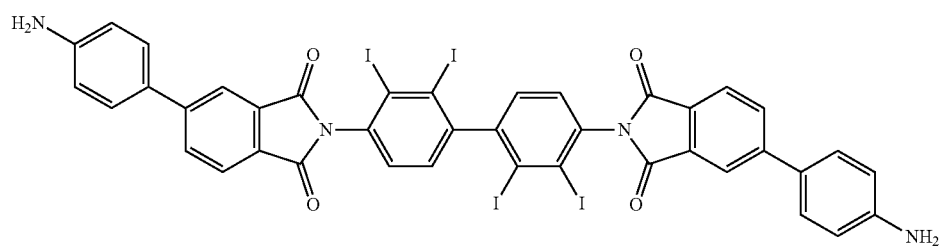
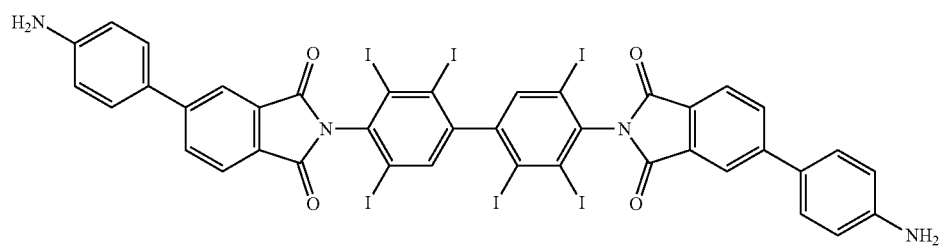
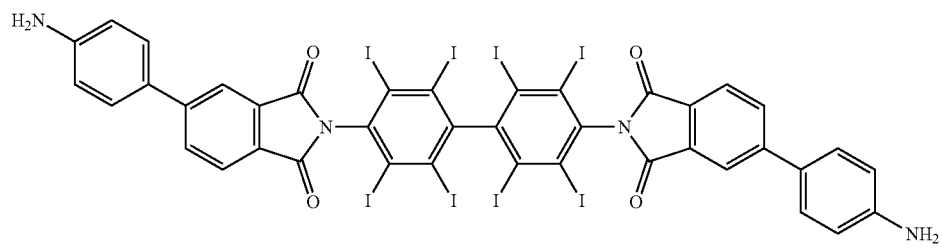 [SMILES: Nc1ccc(-c2ccc3c(c2)C(=O)N(c2c(F)cc(-c4cc(F)c(N5C(=O)c6ccc(-c7ccc(N)cc7)cc6C5=O)c(F)c4)cc2F)C3=O)cc1]
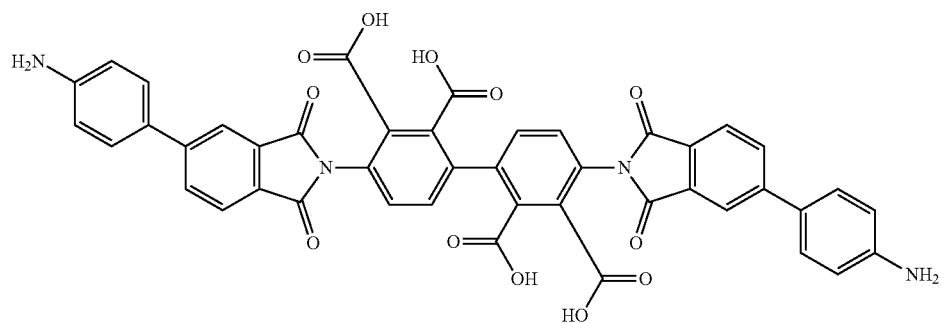

-continued
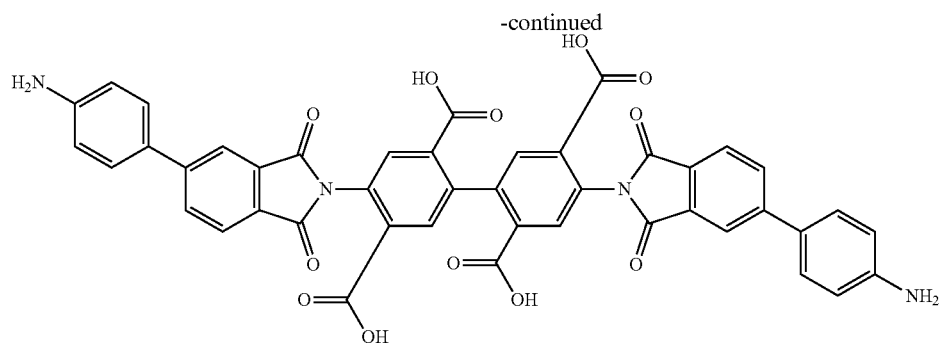
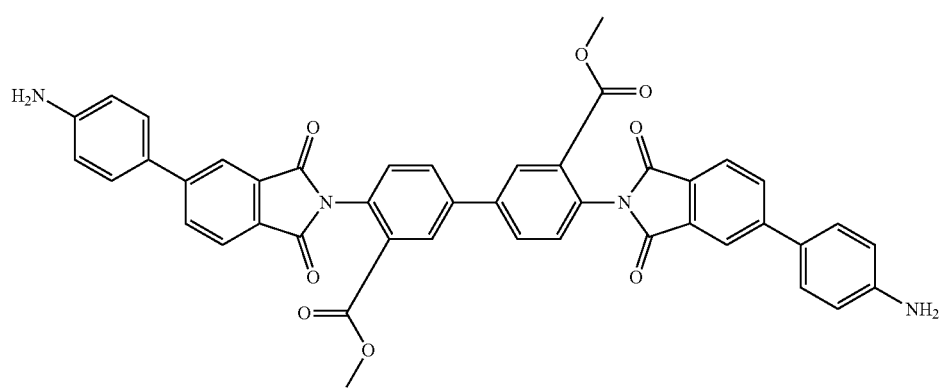
For example, the additional diamine compound may comprise a divalent organic group selected from the following formulas 5a to 5p:
According to an embodiment, the diamine compound of formula 1 may be selected from the compounds of the following structural formulas 1 to 21, but is not limited thereto:
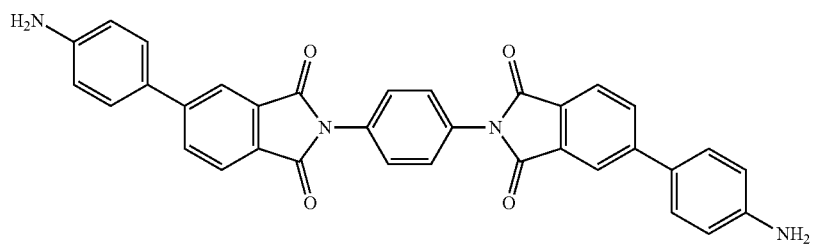
1
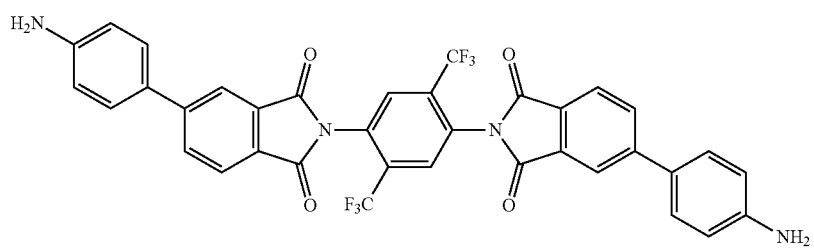
2

3
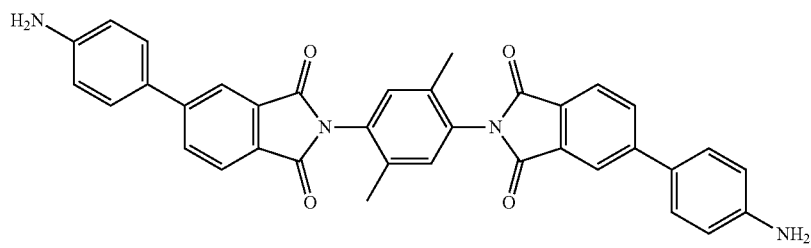
4
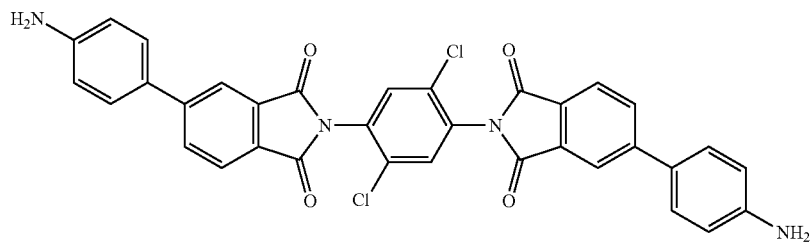
5
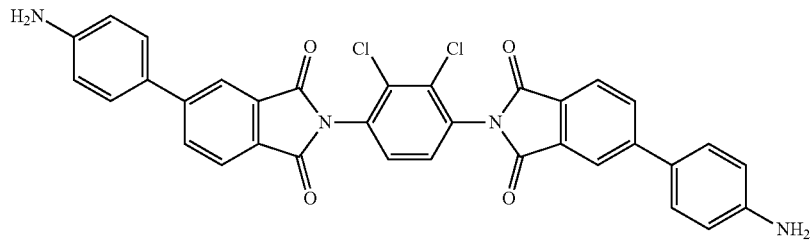
6
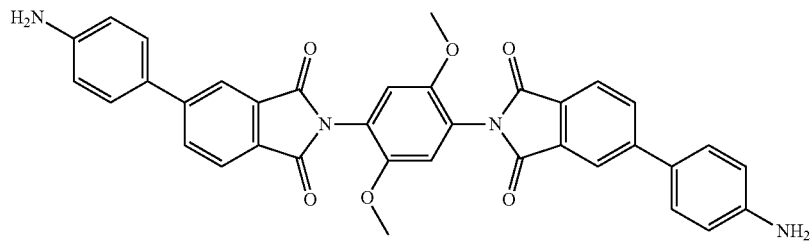
7
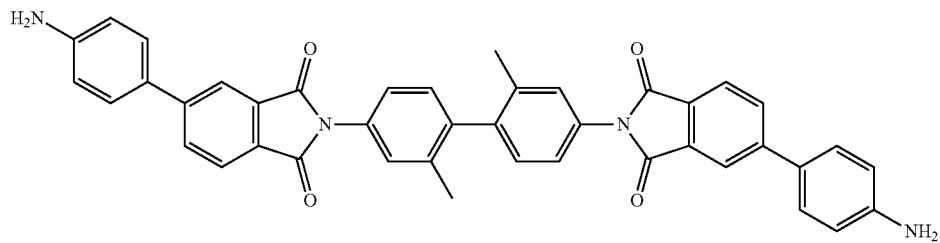
8
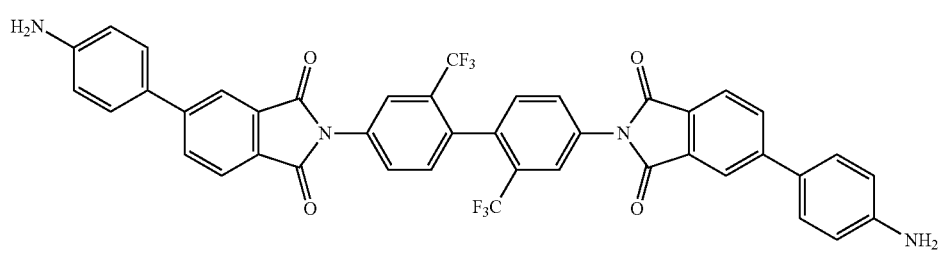

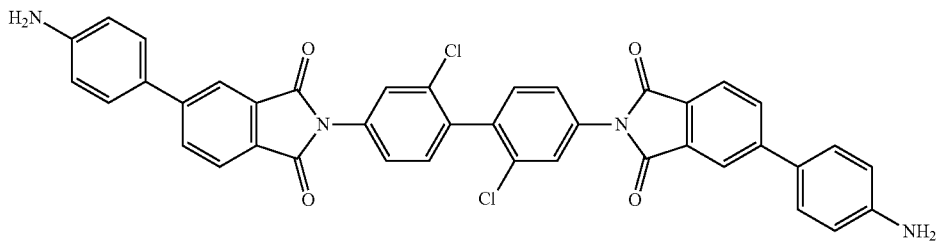
9
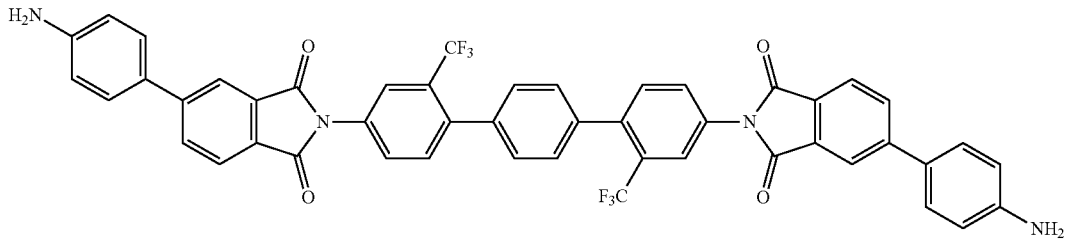
10
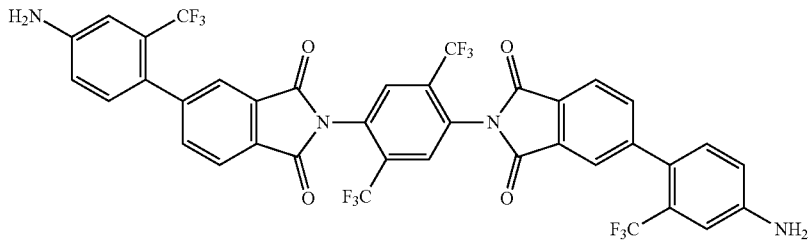
11
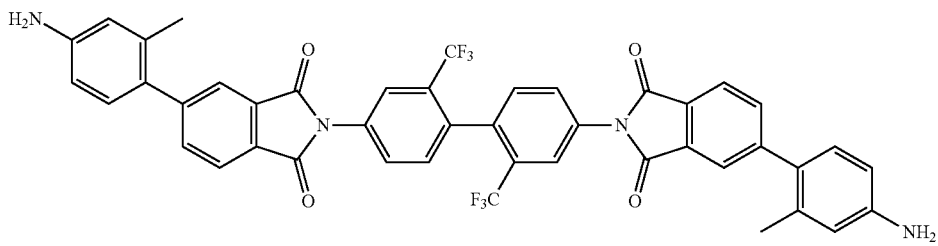
12
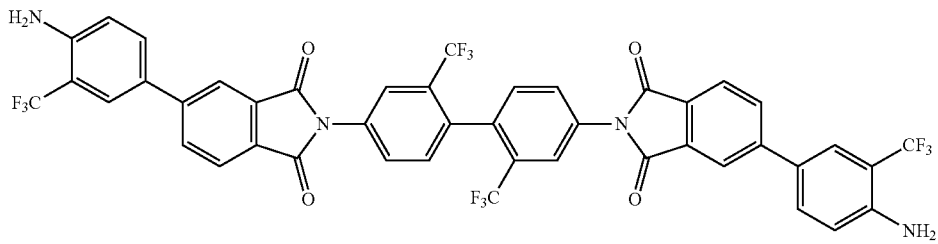
13
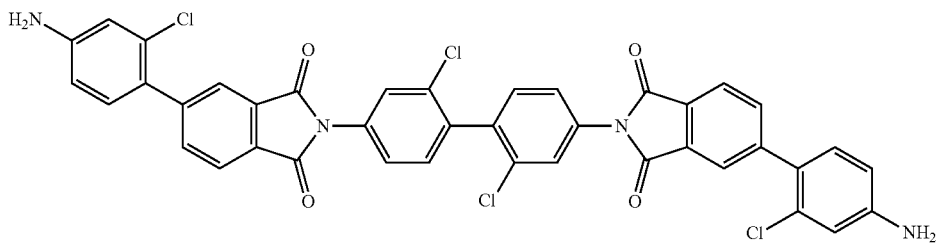
14

-continued
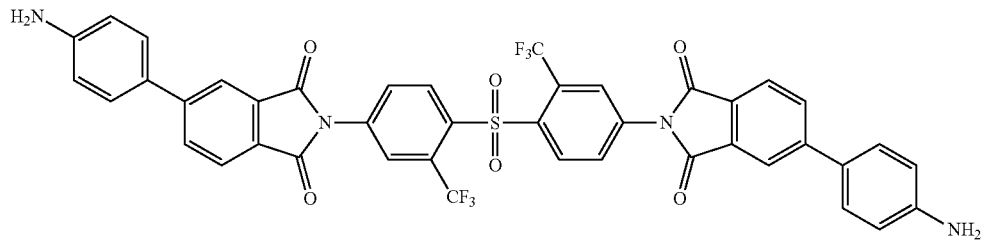
15
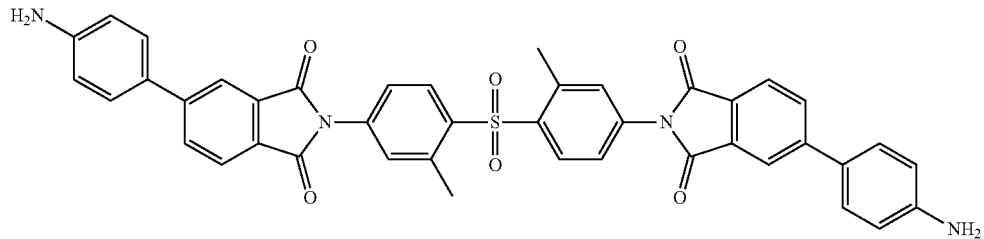
16
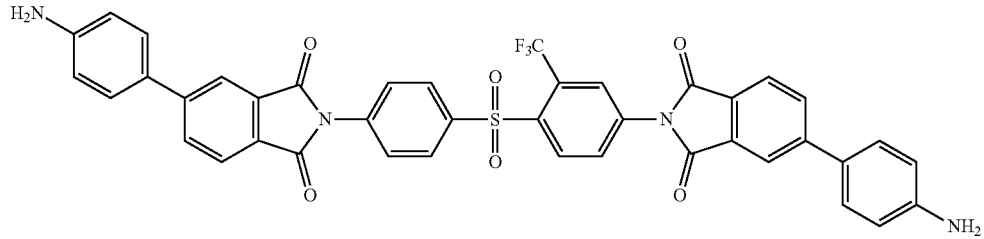
17
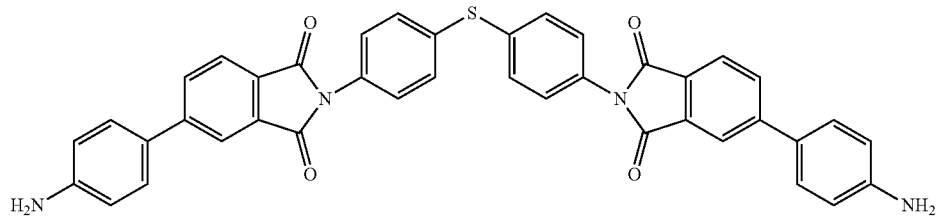
18
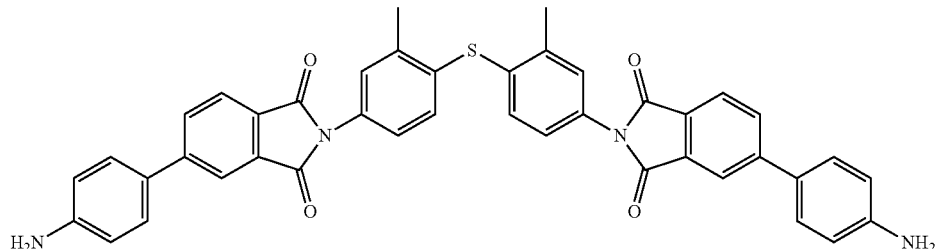
19
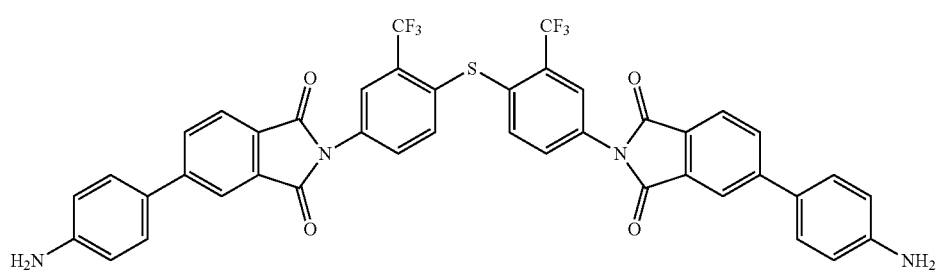
20

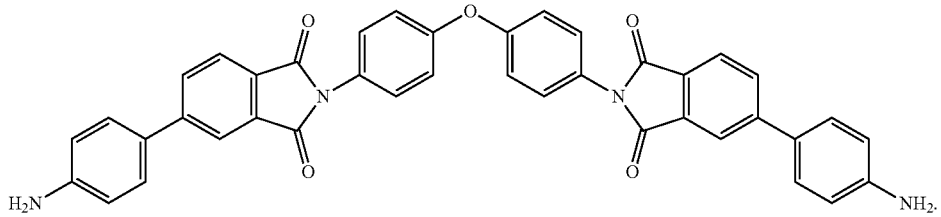

As described above, the diamine compound of the present invention has a structure having a phenylene linker (L) connecting imide rings and the imide rings directly bonded to aryl rings ($Ar_1$ and $Ar_2$) in the molecule. When used as a polymerization component, it can impart improved thermal and mechanical properties after curing.

The method for preparing the diamine compound of formula 1 according to the present invention is not particularly limited and can be prepared by a synthetic method known to those skilled in the art, for example, according to Reaction Scheme 1 below.

[Reaction Scheme 1]

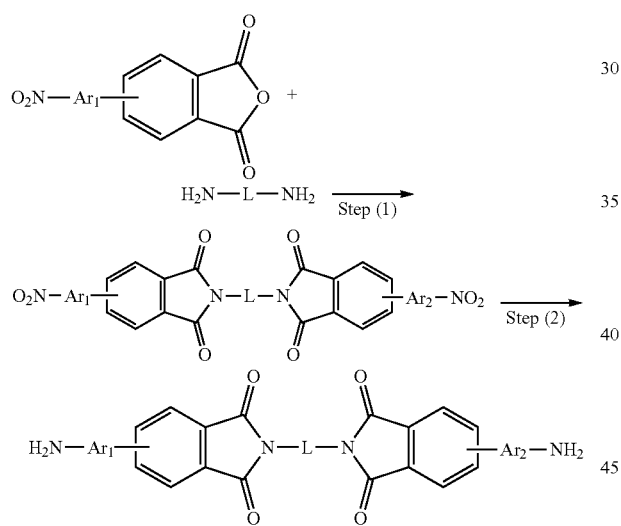

In Reaction Scheme 1, $Ar_1$, $Ar_2$ and L are the same as defined in the formula 1.

Step (1) of Reaction Scheme 1 may be carried out by reacting the reaction compounds in a solvent such as acetic acid or propionic acid with reflux for 10 to 14 hours, such as 12 hours.

In step (2) of Reaction Scheme 1, a reduction reaction may be carried out by injecting hydrogen gas in the presence of a Pd/C catalyst, wherein the solvent may be tetrahydrofuran (THF), N-methylpyrrolidone, etc.

After the step (2), recrystallization may be carried out by adding an alcohol such as ethanol or isopropanol to obtain a solid.

In addition, the present invention provides a polyimide precursor (polyamic acid) prepared by polymerizing a polymerization component including at least one diamine compound and at least one acid dianhydride, wherein the diamine compound comprises the diamine compound of the formula 1. The imidization reaction of the polyimide precursor can be performed to obtain a desired polyimide.

As the acid anhydride used for polymerization reaction, tetracarboxylic dianhydrides may be used, for example. For example, the tetracarboxylic dianhydride includes a tetracarboxylic dianhydride containing aliphatic, alicyclic or aromatic tetravalent organic group(s), or a combination thereof in the molecule, wherein the aliphatic, alicyclic or aromatic tetravalent organic group(s) is connected to each other via a crosslinking structure. Preferably, the tetracarboxylic dianhydride includes an acid dianhydride comprising a structure having a monocyclic or polycyclic aromatic group, a monocyclic or polycyclic alicyclic group, or two or more of them connected by a single bond or a functional group. Alternatively, it may include a tetracarboxylic dianhydride comprising a tetravalent organic group having aliphatic ring(s) or aromatic ring(s), in which each ring is a single ring structure, each ring is fused to form a heterocyclic structure, or each ring is connected by a single bond.

For example, the tetracarboxylic dianhydride may contain a tetravalent organic group selected from the following formulas 2a to 2e.

[Formula 2a]

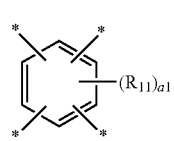

[Formula 2b]

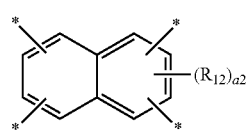

[Formula 2c]

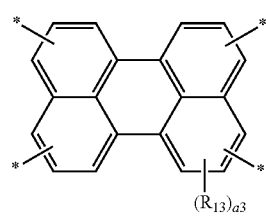

[Formula 2d]

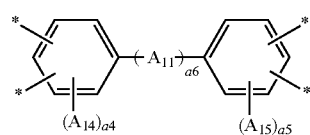

[Formula 2e]

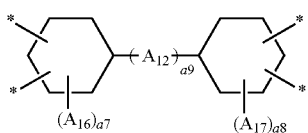

In the formulas 2a to 2e, $R_{11}$ to $R_{17}$ may be each independently selected from a halogen atom selected from F, Cl, Br and I, a hydroxyl group, a thiol group (—SH), a nitro group, a cyano group, an alkyl group having 1 to 10 carbon atoms, a halogenoalkoxy group having 1 to 10 carbon atoms, a halogenoalkyl group having 1 to 10 carbon atoms and an aryl group having 6 to 20 carbon atoms, a1 may be an integer of 0 to 2, a2 may be an integer of 0 to 4, a3, may be an integer of 0 to 8, a4, a5, a6, a7, a8 and a9 may be each independently an integer of 0 to 3, $A_{11}$ and $A_{12}$ may be each independently selected from the group consisting of a single bond, —O—, —CR'R''— (wherein, R' and R'' are each independently selected from the group consisting of a hydrogen atom, an alkyl group having 1 to 10 carbon atoms (e.g., methyl group, ethyl group, propyl group, isopropyl group, n-butyl, tert-butyl group, pentyl group, etc.) and a haloalkyl group having 1 to 10 carbon atoms (e.g., trifluoromethyl group, etc.)), —C(=O)—, —C(=O)O—, —C(=O)NH—, —S—, —SO—, —SO$_2$—, —O[CH$_2$CH$_2$O]$_y$— (y is an integer of 1 to 44), —NH(C=O)NH—, —NH(C=O)O—, a monocyclic or polycyclic cycloalkylene group having 6 to 18 carbon atoms (e.g., cyclohexylene group, etc.), a monocyclic or polycyclic arylene group having 6 to 18 carbon atoms (e.g., phenylene group, naphthalene group, fluorenylene group, etc.), and combinations thereof.

In addition, the tetracarboxylic dianhydride may comprise a tetravalent organic group selected from the following formulas 3a to 3n.

(3a)

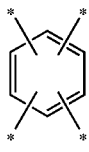

(3b)

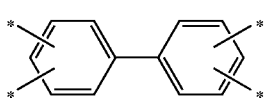

(3c)

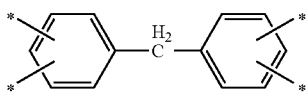

(3d)

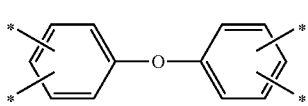

(3e)

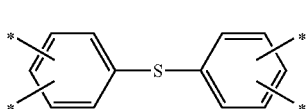

(3f)

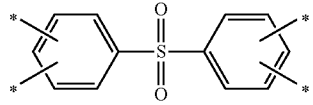

(3g)

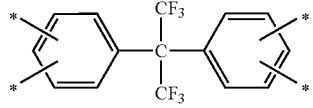

(3h)

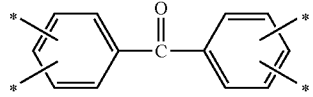

(3i)

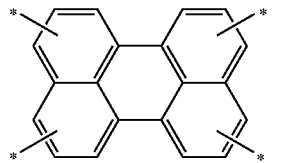

(3j)

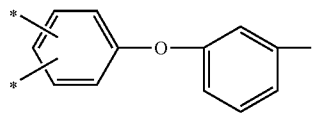

(3k)

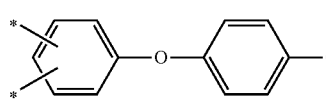

(3l)

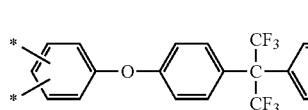

(3m)

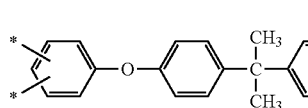

(3n)

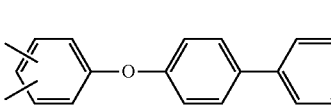

At least one hydrogen atom in the tetravalent organic group of the formulas 3a to 3n may be substituted with a substituent selected from a halogen atom selected from F, Cl, Br and I, a hydroxyl group, a thiol group, a nitro group, a cyano group, an alkyl group having 1 to 10 carbon atoms, a halogenoalkoxy group having 1 to 10 carbon atoms, a halogenoalkyl group having 1 to 10 carbon atoms and an aryl group having 6 to 20 carbon atoms. For example, the halogen atom may be fluorine, the halogenoalkyl group may be a fluoroalkyl group having 1 to 10 carbon atoms containing a fluorine atom, selected from a fluoromethyl group, a perfluoroethyl group, a trifluoromethyl group, etc. The alkyl group may be selected from a methyl group, an ethyl group, a propyl group, an isopropyl group, a t-butyl group, a pentyl group, and a hexyl group, and the aryl group is selected from a phenyl group and a naphthalenyl group. More preferably, it may be a fluorine atom or a substituent containing a fluorine atom such as a fluoroalkyl group.

According to one embodiment, in the polymerization of the polyimide precursor, one or more additional diamine may be further used in addition to the diamine compound of formula 1. For example, it may include a diamine compound comprising a divalent organic group selected from a monocyclic or polycyclic aromatic divalent organic group having 6 to 24 carbon atoms, a monocyclic or polycyclic alicyclic divalent organic group having 6 to 18 carbon atoms, or a divalent organic group having two or more of them connected by a single bond or a functional group. Alternatively, it may include a diamine compound comprising a divalent organic group having aliphatic ring(s) or aromatic ring(s) in which each ring is a single ring structure, each ring is fused to form a heterocyclic structure, or each ring is connected by a single bond.

For example, the additional diamine compound may comprise a divalent organic group selected from the following formulas 4a to 4e:

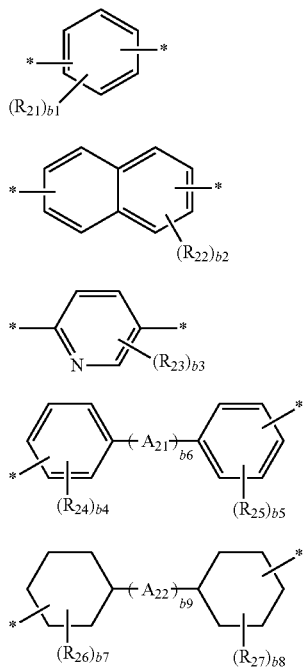

[Formula 4a]

[Formula 4b]

[Formula 4c]

[Formula 4d]

[Formula 4e]

In the formulas 4a to 4e, $R_{21}$ to $R_{27}$ may be each independently selected from a halogen atom selected from F, Cl, Br and I, a hydroxyl group, a thiol group, a nitro group, a cyano group, an alkyl group having 1 to 10 carbon atoms, a halogenoalkoxy group having 1 to 10 carbon atoms, a halogenoalkyl group having 1 to 10 carbon atoms and an aryl group having 6 to 20 carbon atoms, A21 and A22 may be each independently selected from the group consisting of a single bond, —O—, —CR'R''— (wherein, R' and R'' are each independently selected from the group consisting of a hydrogen atom, an alkyl group having 1 to 10 carbon atoms (e.g., methyl group, ethyl group, propyl group, isopropyl group, n-butyl, tert-butyl group, pentyl group, etc.) and a haloalkyl group having 1 to 10 carbon atoms (e.g., trifluoromethyl group, etc.)), —C(=O)—, —C(=O)O—, —C(=O)NH—, —S—, —SO—, —SO₂—, —O[CH₂CH₂O]$_y$— (y is an integer of 1 to 44), —NH(C=O)NH—, —NH(C=O)O—, a monocyclic or polycyclic cycloalkylene group having 6 to 18 carbon atoms (e.g., cyclohexylene group, etc.), a monocyclic or polycyclic arylene group having 6 to 18 carbon atoms (e.g., phenylene group, naphthalene group, fluorenylene group, etc.), and combinations thereof, b1 is an integer from 0 to 4, b2 is an integer from 0 to 6, b3 is an integer from 0 to 3, b4 and b5 are each independently an integer from 0 to 4, and b7 and b8 are each independently an integer from 0 to 4, and b6 and b9 are each independently an integer from 0 to 3.

For example, the additional diamine compound may comprise a divalent organic group selected from the following formulas 5a to 5p:

(5a)

(5b)

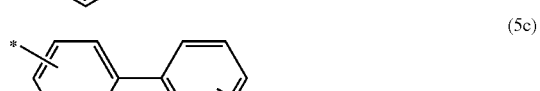

(5c)

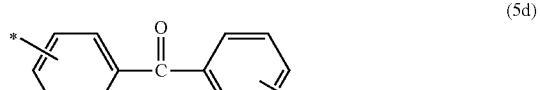

(5d)

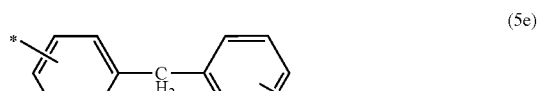

(5e)

(5f)

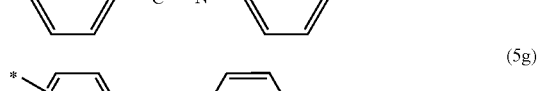

(5g)

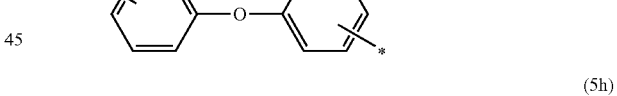

(5h)

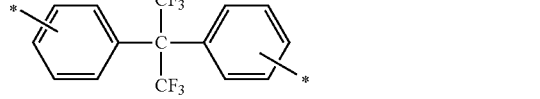

(5i)

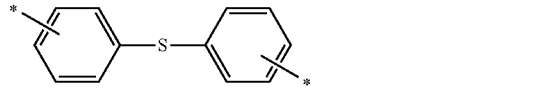

(5j)

(5k)

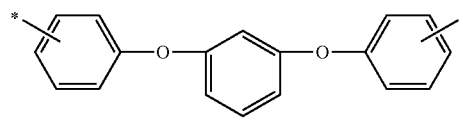

(5l)

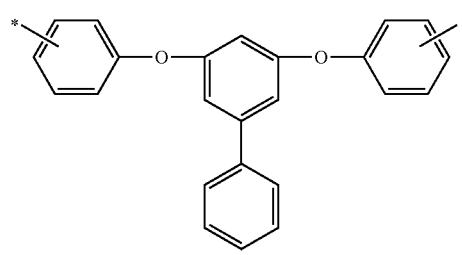

(5m)

(5n)

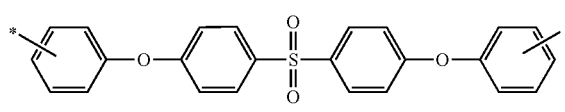

(5o)

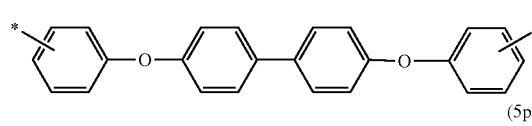

(5p)

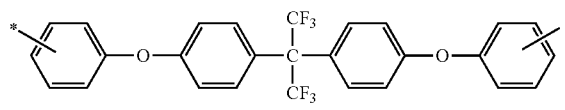

Alternatively, the additional diamine compound may comprise a divalent organic group in which aromatic ring(s) or aliphatic structure(s) form a rigid chain structure, for example, a divalent organic group having aliphatic ring(s) or aromatic ring(s) in which each ring is a single ring structure, each ring is connected by a single bond, or each ring is fused to form a heterocyclic structure.

According to one embodiment of the present invention, the reaction molar ratio of the total tetracarboxylic dianhydride to the diamine may be 1:1.1 to 1.1:1. For improvement of reactivity and processability, it is preferred that the total tetracarboxylic dianhydride is reacted in excess relative to the diamine compound, or that the diamine compound is reacted in excess relative to the total tetracarboxylic dianhydride.

According to one embodiment of the invention, the tetracarboxylic dianhydride and the diamine compound may be reacted in a molar ratio of 1:0.98 to 0.98:1, preferably 1:0.99 to 0.99:1.

The polymerization reaction may be carried out by a conventional polymerization method of a polyimide or a precursor thereof, such as solution polymerization.

The organic solvent that can be used in the polymerization reaction may include ketones such as γ-butyrolactone, 1,3-dimethyl-2-imidazolidinone, methyl ethyl ketone, cyclohexanone, cyclopentanone and 4-hydroxy-4-methyl-2-pentanone; aromatic hydrocarbons such as toluene, xylene and tetramethylbenzene; glycol ethers (Cellosolve) such as ethylene glycol monoethyl ether, ethylene glycol monomethyl ether, ethylene glycol monobutyl ether, diethylene glycol monoethyl ether, diethylene glycol monomethyl ether, diethylene glycol monobutyl ether, propylene glycol monomethyl ether, propylene glycol monoethyl ether, dipropylene glycol diethyl ether and triethylene glycol monoethyl ether; ethyl acetate, butyl acetate, ethylene glycol monoethyl ether acetate, ethylene glycol monobutyl ether acetate, diethylene glycol monoethyl ether acetate, dipropylene glycol monomethyl ether acetate, ethanol, propanol, ethylene glycol, propylene glycol, dimethylpropionamide (DMPA), diethylpropionamide (DEPA), dimethylacetamide (DMAc), N,N-diethylacetamide, dimethylformamide (DMF), diethylformamide (DEF), N-methylpyrrolidone (NMP), N-ethylpyrrolidone (NEP), N,N-dimethylmethoxyacetamide, dimethylsulfoxide, pyridine, dimethylsulfone, hexamethylphosphoramide, tetramethylurea, N-methylcaprolactam, tetrahydrofuran, m-dioxane, p-dioxane, 1,2-dimethoxyethane, bis(2-methoxyethyl)ether, 1,2-bis(2-methoxyethoxy)ethane, bis[2-(2-methoxyethoxy)]ether, Equamide M100 (3-methoxy-N,N-dimethylpropionamide, Idemitsu Kosan Co., Ltd.), Equamide B100 (3-butoxy-N,N-dimethylpropionamide, Idemitsu Kosan Co., Ltd.) and the like, and these solvents may be used alone or as a mixture of two or more.

According to one embodiment, the organic solvent may have a boiling point of 300° C. or less and a positive partition coefficient Log P at 25° C., more specifically, the partition coefficient Log P may be 0.01 to 3, or 0.01 to 2, or 0.01 to 1. The partition coefficient can be calculated using an ACD/LogP module of ACD/Percepta platform from ACD/Labs. The ACD/LogP module uses an algorithm based on QSPR (Quantitative Structure-Property Relationship) methodology using 2D molecular structures.

The solvent having a positive partition coefficient Log P refers to a hydrophobic solvent. According to the research of the present inventors, it is found that when the polyimide precursor composition is prepared using a specific solvent having a positive partition coefficient Log P, the edge back phenomenon is improved. In addition, in the present invention it is possible to control the edge back phenomenon of the solution without using additives for controlling surface tension of the material and smoothness of the coating film, such as a leveling agent, by using a solvent having a positive partition coefficient Log P as described above. Since additional additives are not used, it is possible to eliminate quality and process problems such as the presence of low-molecular substances in the final product, as well as more efficiently to form a polyimide film having uniform properties.

For example, in the process of coating the polyimide precursor composition on the glass substrate, an edge back phenomenon may occur due to shrinkage of the coating layer during curing or under the condition of standing the coating solution in a humidity condition. The edge back phenomenon of the coating solution may cause a variation in the thickness of the film. As a result, the film may be cut or have broken edges when cutting due to a lack of flex resistance of the film, causing problems of poor process workability and reduced yield.

In addition, when fine foreign substances having polarity are introduced into the polyimide precursor composition applied on the substrate, for the polyimide precursor composition including a polar solvent having a negative partition coefficient Log P, sporadic coating cracks or thickness change may occur based on location of the foreign substance due to polarity of the foreign substance. In case of using a hydrophobic solvent having a positive partition coefficient Log P, the occurrence of thickness change due to cracking of the coating may be reduced or suppressed even when fine foreign substances having polarity are introduced.

Specifically, in the polyimide precursor composition including a solvent having a positive Log P, an edge back ratio defined by the following Equation 1 may be 0% to 0.1% or less.

$$\text{Edge back ratio (\%)} = [(A-B)/A] \times 100 \quad \text{[Equation 1]}$$

wherein,

A: area of the polyimide precursor composition completely coated on the substrate (100 mm×100 mm), B: area after the edge back phenomenon occurs from the edge of the substrate with the polyimide precursor composition or the polyimide film coated thereon.

The edge back phenomenon of the polyimide precursor composition and the polyimide film may occur within 30 minutes after coating the polyimide precursor composition solution, and particularly, the film may be rolled up from the edge to make the thickness of the edge thicker.

After coating the polyimide precursor composition on a substrate and then standing it at a temperature of 20 to 30° C. and in a humidity condition of 40% or more, more specifically, in a humidity condition of 40% to 80%, that is, in each humidity condition of 40%, 50%, 60%, 70% and 80% for 10 minutes or more, for example 40 minutes or more, the edge back ratio of the coated composition solution may be 0.1% or less, preferable 0.05%, more preferably almost 0%.

The edge back ratio as described above is maintained even after curing by heat treatment, and specifically the edge back ratio may be 0.05% or less, more preferably almost 0%.

By solving this edge back phenomenon, the polyimide precursor composition according to the present invention can obtain a polyimide film having more uniform characteristics, thereby further improving the yield of the manufacturing process.

In addition, the solvent used in the polymerization reaction can have a density of 1 g/cm³ or less as measured by standard ASTM D1475. If the density is more than 1 g/cm³, the relative viscosity may increase and the process efficiency may be reduced.

The polymerization reaction may be carried out in an inert gas or a nitrogen stream and may be carried out under anhydrous condition.

The reaction temperature during the polymerization reaction may be −20 to 80° C., preferably 0 to 80° C. If the reaction temperature is too high, the reactivity may become high and the molecular weight may become large, and the viscosity of the precursor composition may increase, which may be unfavorable in the process.

The polyimide precursor composition containing polyamic acid may be in the form of a solution dissolved in an organic solvent. For example, when the polyimide precursor is synthesized in an organic solvent, the solution may be the reaction solution as obtained, or may be obtained by diluting this reaction solution with another solvent. When the polyimide precursor is obtained as a solid powder, it may be dissolved in an organic solvent to prepare a solution.

According to one embodiment, the content of the composition may be adjusted by adding an organic solvent such that the total polyimide precursor content is 8 to 25% by weight, preferably 10 to 25% by weight, more preferably 10 to 20% by weight. The polyimide precursor composition may be adjusted to have a viscosity of 3,000 cP or more and 10,000 cP or less, preferably 4,000 cP or more and 9,000 cP or less, more preferably 4,000 cP or more and 8,000 cP or less. When the viscosity of the polyimide precursor composition exceeds 10,000 cP, the efficiency of defoaming during processing of the polyimide film is lowered. It results in not only the lowered efficiency of process but also the deteriorated surface roughness of the produced film due to bubble generation. It may lead to the deteriorated electrical, optical and mechanical properties.

Then, the polyimide precursor resulted from the polymerization reaction may be imidized by chemical or thermal imidization to prepare a transparent polyimide film.

According to one embodiment, the polyimide film may be manufactured by a method comprising:

applying the polyimide precursor composition onto a substrate; and heating and curing the applied polyimide precursor composition.

As the substrate, a glass substrate, a metal substrate, a plastic substrate, or the like can be used without any particular limitation. Among them, a glass substrate may be preferable which is excellent in thermal and chemical stabilities during the imidization and curing process for the polyimide precursor and can be easily separated even without any treatment with additional release agent while not damaging the polyimide film formed after curing.

The applying process may be carried out according to a conventional application method. Specifically, a spin coating method, a bar coating method, a roll coating method, an air knife method, a gravure method, a reverse roll method, a kiss roll method, a doctor blade method, a spray method, a dipping method, a brushing method, or the like may be used. Of these, it is more preferred to carry out by a casting method which allows a continuous process and enables to increase an imidization rate of polyimide.

In addition, the polyimide precursor composition may be applied on the substrate in the thickness range such that the polyimide film to be finally produced has a thickness suitable for a display substrate. For example, it may be applied in an amount such that the thickness is 10 to 30 μm.

After the application of the polyimide precursor composition, a drying process for removing the solvent remained in the polyimide precursor composition may be further optionally performed prior to the curing process.

The drying process may be carried out according to a conventional method. Specifically, the drying process may be carried out at a temperature of 140° C. or lower, or from 80° C. to 140° C. If the drying temperature is lower than 80° C., the drying process becomes longer. If the drying temperature exceeds 140° C., the imidization proceeds rapidly, making it difficult to form a polyimide film having a uniform thickness.

Then, the polyimide precursor composition is applied on a substrate and heat-treated in an IR oven, in a hot air oven, or on a hot plate. The heat treatment temperature may range from 300 to 500° C., preferably from 320 to 480° C. The heat treatment may be performed in a multi-step heating process within the above temperature range. The heat treatment process may be performed for 20 to 70 minutes, and preferably for 20 to 60 minutes.

The residual stress immediately after curing of the polyimide film prepared as described above may be 40 MPa or less, and the residual stress change after standing the polyimide film at 25° C. and 50% humidity for 3 hours may be 5 MPa or less.

The polyimide film may have a yellowness of 15 or less, and preferably 13 or less. Further, the polyimide film may have a haze of 2% or less, and preferably 1% or less.

In addition, the polyimide film may have a transmittance at 450 nm of 75% or more, a transmittance at 550 nm of 85% or more, and a transmittance at 630 nm of 90% or more.

The polyimide film may have high heat resistance, for example, a thermal decomposition temperature (Td_1%) in which mass loss is 1% may be 500° C. or higher.

The polyimide film prepared as described above may have a modulus of 0.1 to 4 GPa. When the modulus (modulus of elasticity) is less than 0.1 GPa, the film has low rigidity and is easily fragile to external impact. When the modulus exceeds 4 GPa, the coverlay film has excellent rigidity, but cannot secure sufficient flexibility.

In addition, the polyimide film may have an elongation of 20% or more, preferably 50% or more, and a tensile strength of 130 MPa or more, preferably 140 MPa or more.

In addition, the polyimide film according to the present invention may have excellent thermal stability against a temperature change. For example, it may have a thermal expansion coefficient of −10 to 100 ppm/° C., preferably from −7 to 90 ppm/° C., more preferably 80 ppm/° C. or less, after n+1 times (n is an integer of at least 0) heating and cooling processes in a temperature range of 100 to 350° C.

In addition, the polyimide film according to the present invention may have a retardation in a thickness direction ($R_{th}$) of −150 nm to +150 nm, preferably −130 nm to +130 nm, thereby exhibiting optical isotropy to improve visual sensibility.

According to one embodiment, the polyimide film may have an adhesive force to a carrier substrate of 5 gf/in or more, and preferably 10 gf/in or more.

In addition, the present invention provides a flexible device comprising the polyimide film as a substrate.

In one embodiment, the flexible device can be manufactured by a method comprising applying the polyimide precursor composition on a carrier substrate, and then heating it to form a polyimide film, and then forming a device on the polyimide film; and peeling from the carrier substrate the polyimide film having the device formed thereon.

The flexible device may be, for example, a thin film transistor, a liquid crystal display (LCD), an electronic paper, an organic EL display, a plasma display panel (PDP), or an IC card.

Hereinafter, embodiments of the present invention will be described in detail so that those skilled in the art can easily carry out the present invention. The present invention may, however, be embodied in many different forms and should not be construed as limited to the embodiments set forth herein.

<Synthesis Example 1> Preparation of Compound 1

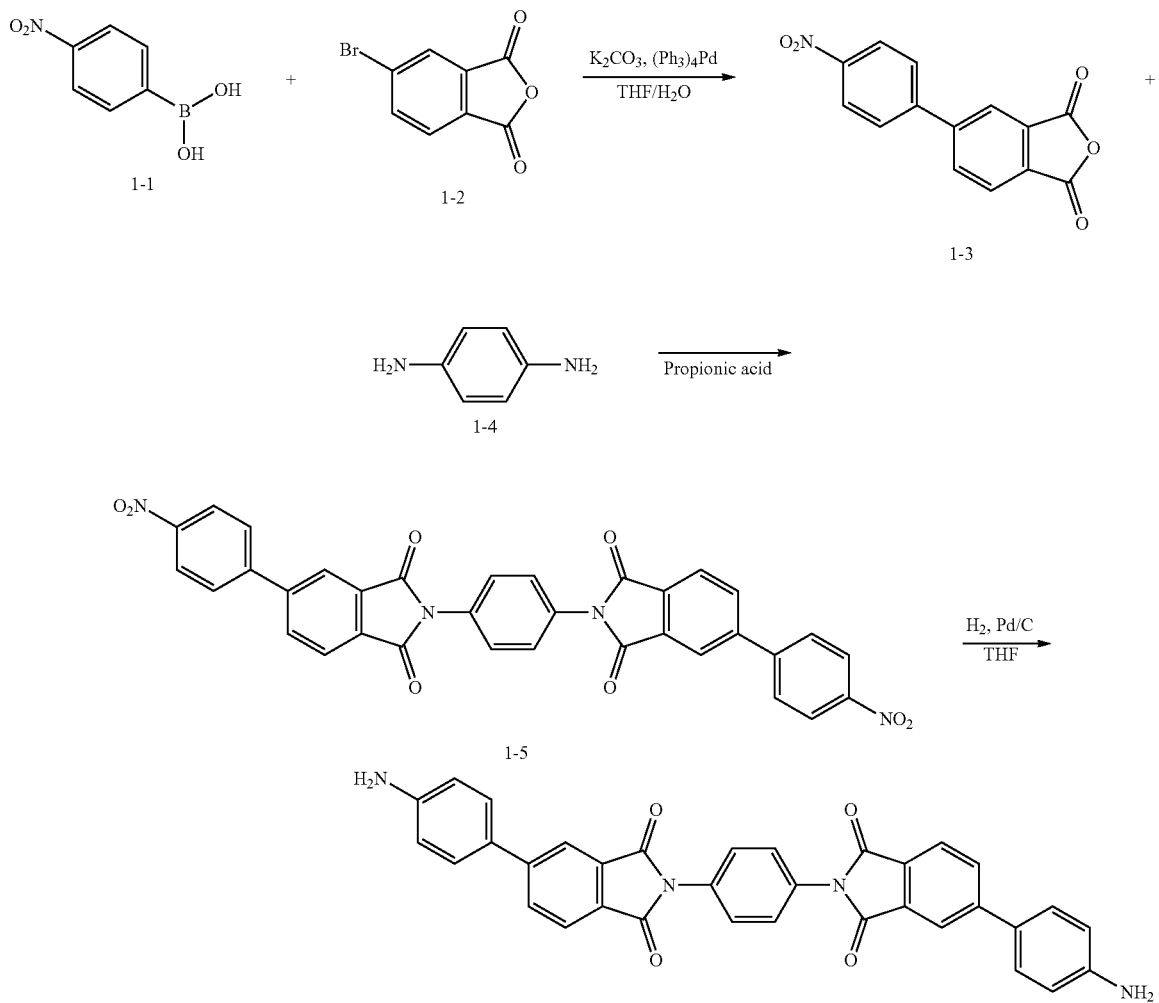

Preparation of Compound 1-3

Compound 1-1 (108.0 g, 0.65 mol) and compound 1-2 (73.0 g, 0.32 mol) were dissolved in THF (500 mL) in a nitrogen atmosphere, and potassium carbonate (135.2 g, 0.97 mol) was dissolved in water (250 mL), and then heated to 100° C. Palladium tetratriphenylphosphine (11.29 g) was added to the reaction mixture with reflux and stirred for 12 hours. After completion of the reaction, the reaction mixture was cooled to room temperature, and then ethyl acetate (250 mL) was added to separate an organic layer. The separated organic layer was dried over anhydrous magnesium sulfate, and the solvent was removed through a vacuum distillation apparatus (BUCHI Rotavapor R-300) to obtain compound 1-3 (60.3 g, yield 69%).

Preparation of Compound 1-5

Compound 1-3 (20.0 g, 74.3 mmol) and compound 1-4 (4.0 g, 37.1 mmol) were added to propionic acid (500 mL) with reflux and stirred for 12 hours. After completion of the reaction, the reaction mixture was cooled to room temperature, and ethanol (500 mL) was added to disperse the resulting solid. After filtering the reaction mixture, the obtained solid was washed with water and ethanol (1:1, volume ratio) to obtain compound 1-5 (21.5 g, yield 95%).

Preparation of Compound 1

Compound 1-5 (21.5 g, 35.3 mmol) was dissolved in THF (200 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (200 mL) to obtain compound 1 (19.0 g, yield 98%).

HR LC/MS/MS m/z calcd for $C_{34}H_{22}N_4O_4$ (M+): 550.1641; found: 550.1639

<Synthesis Example 2> Preparation of Compound 2

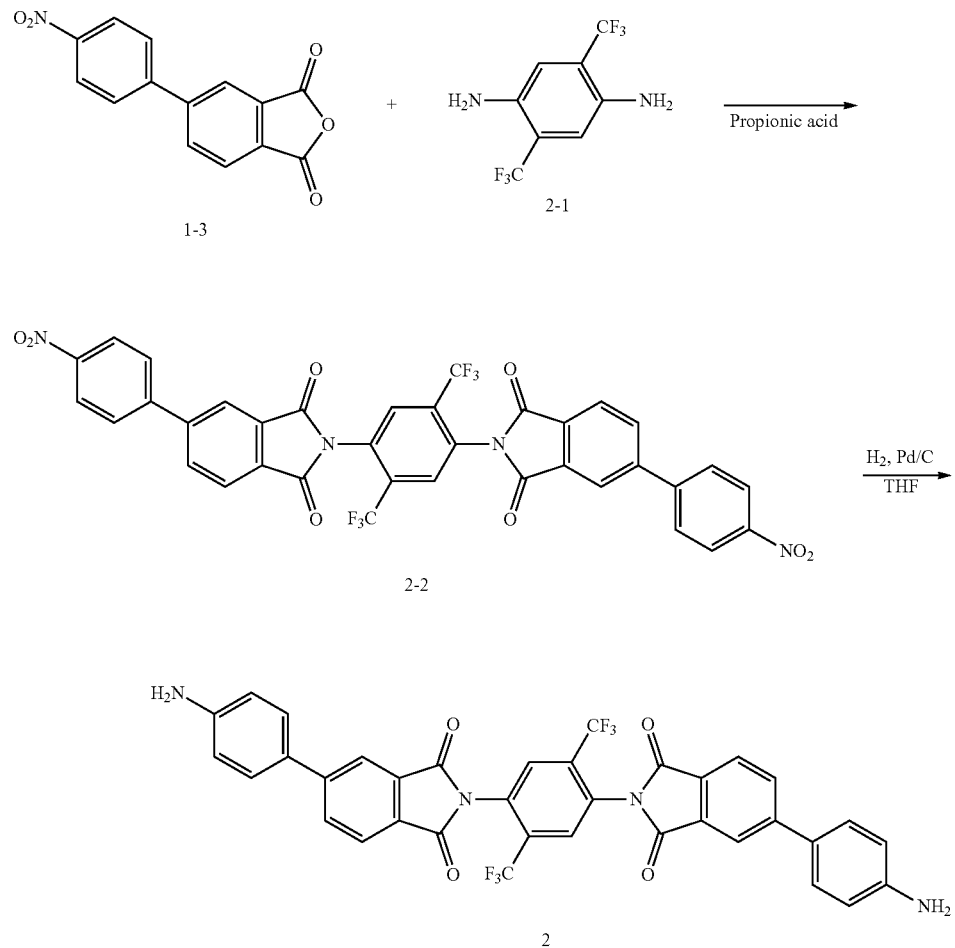

Preparation of Compound 2-2

Compound 1-3 (20.0 g, 74.3 mmol) and compound 2-1 (9.07 g, 37.1 mmol) were added to propionic acid (500 mL) with reflux and stirred for 12 hours. After completion of the reaction, the reaction mixture was cooled to room temperature, and ethanol (500 mL) was added to disperse the resulting solid. After filtering the reaction mixture, the obtained solid was washed with water and ethanol (1:1, volume ratio) to obtain compound 2-2 (24.9 g, yield 90%).

Preparation of Compound 2

Compound 2-2 (24.9 g, 33.3 mmol) was dissolved in THF (200 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (200 mL) to obtain compound 2 (21.7 g, yield 95%).

HR LC/MS/MS m/z calcd for $C_{36}H_{20}F_6N_4O_4$ (M+): 687.1422; found: 687.1420

<Synthesis Example 3> Preparation of Compound 3

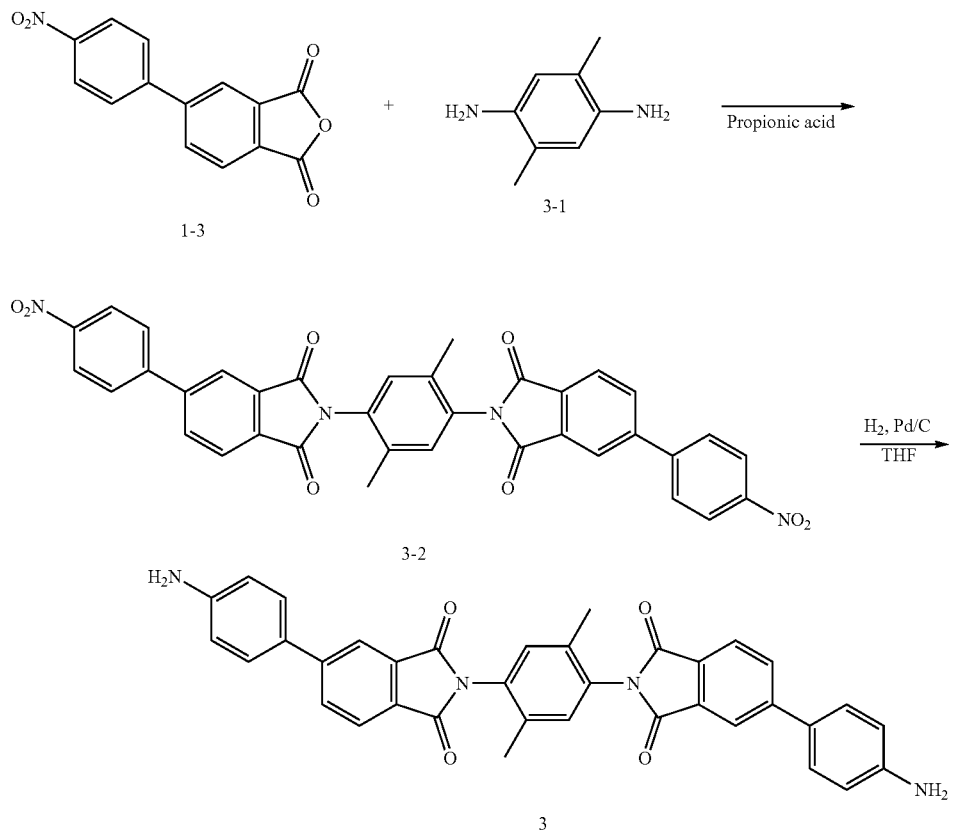

Preparation of Compound 3-2

Compound 1-3 (20.0 g, 74.3 mmol) and compound 3-1 (5.05 g, 37.1 mmol) were added to propionic acid (500 mL) with reflux and stirred for 12 hours. After completion of the reaction, the reaction mixture was cooled to room temperature, and ethanol (500 mL) was added to disperse the resulting solid. After filtering the reaction mixture, the obtained solid was washed with water and ethanol (1:1, volume ratio) to obtain compound 3-2 (21.8 g, yield 92%).

Preparation of Compound 3

Compound 3-2 (21.8 g, 34.2 mmol) was dissolved in THF (200 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (200 mL) to obtain compound 3 (19.5 g, yield 99%).

HR LC/MS/MS m/z calcd for $C_{36}H_{26}N_4O_4$ (M+): 578.1954; found: 578.1949

<Synthesis Example 4> Preparation of Compound 4

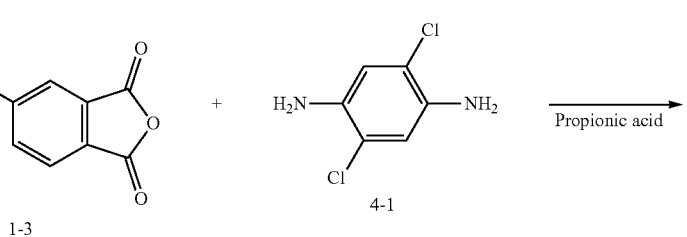

-continued

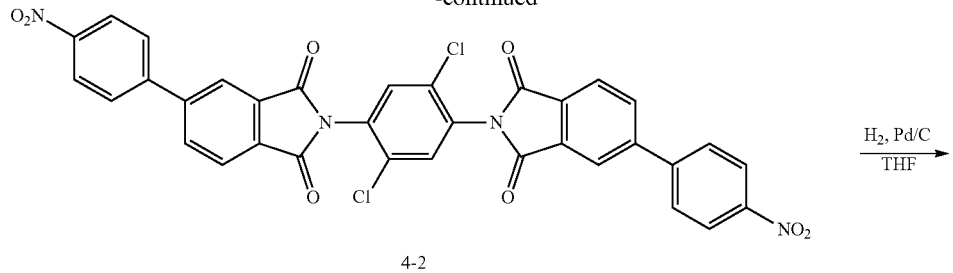
4-2

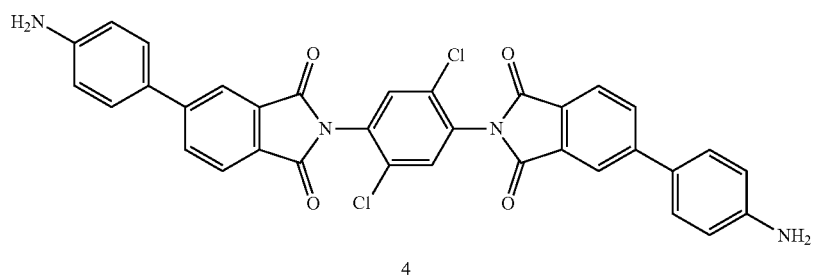
4

Preparation of Compound 4-2

Compound 1-3 (20.0 g, 74.3 mmol) and compound 4-1 (6.57 g, 37.1 mmol) were added to propionic acid (500 mL) with reflux and stirred for 12 hours. After completion of the reaction, the reaction mixture was cooled to room temperature, and ethanol (500 mL) was added to disperse the resulting solid. After filtering the reaction mixture, the obtained solid was washed with water and ethanol (1:1, volume ratio) to obtain compound 4-2 (22.1 g, yield 88%).

Preparation of Compound 4

Compound 4-2 (22.1 g, 32.6 mmol) was dissolved in THF (200 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (200 mL) to obtain compound 4 (16.1 g, yield 80%).

HR LC/MS/MS m/z calcd for $C_{34}H_{20}Cl_2N_4O_4$ (M+): 618.0862; found: 618.0859

<Synthesis Example 5> Preparation of Compound 5

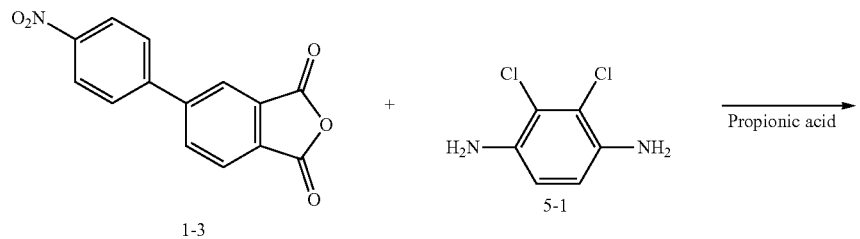

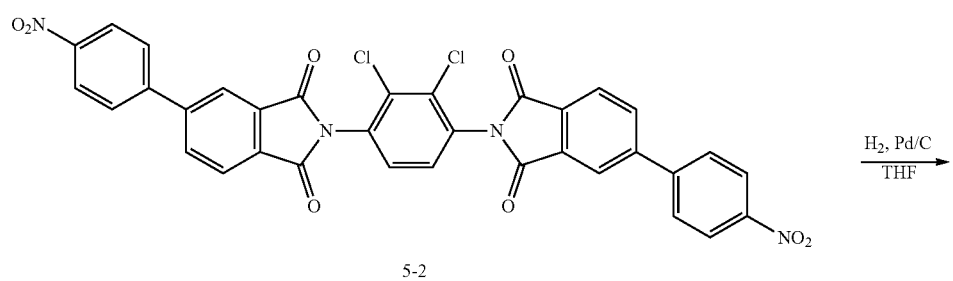
5-2

-continued

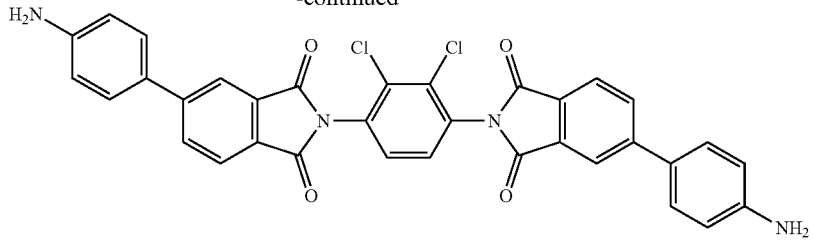

5

Preparation of Compound 5-2

Compound 1-3 (20.0 g, 74.3 mmol) and compound 5-1 (6.57 g, 37.1 mmol) were added to propionic acid (500 mL) with reflux and stirred for 12 hours. After completion of the reaction, the reaction mixture was cooled to room temperature, and ethanol (500 mL) was added to disperse the resulting solid. After filtering the reaction mixture, the obtained solid was washed with water and ethanol (1:1, volume ratio) to obtain compound 5-2 (22.9 g, yield 91%).

Preparation of Compound 5

Compound 5-2 (22.9 g, 32.6 mmol) was dissolved in THF (200 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (200 mL) to obtain compound 5 (20.0 g, yield 96%).

HR LC/MS/MS m/z calcd for $C_{34}H_{20}Cl_2N_4O_4$ (M+): 618.0862; found: 618.0860

<Synthesis Example 6> Preparation of Compound 6

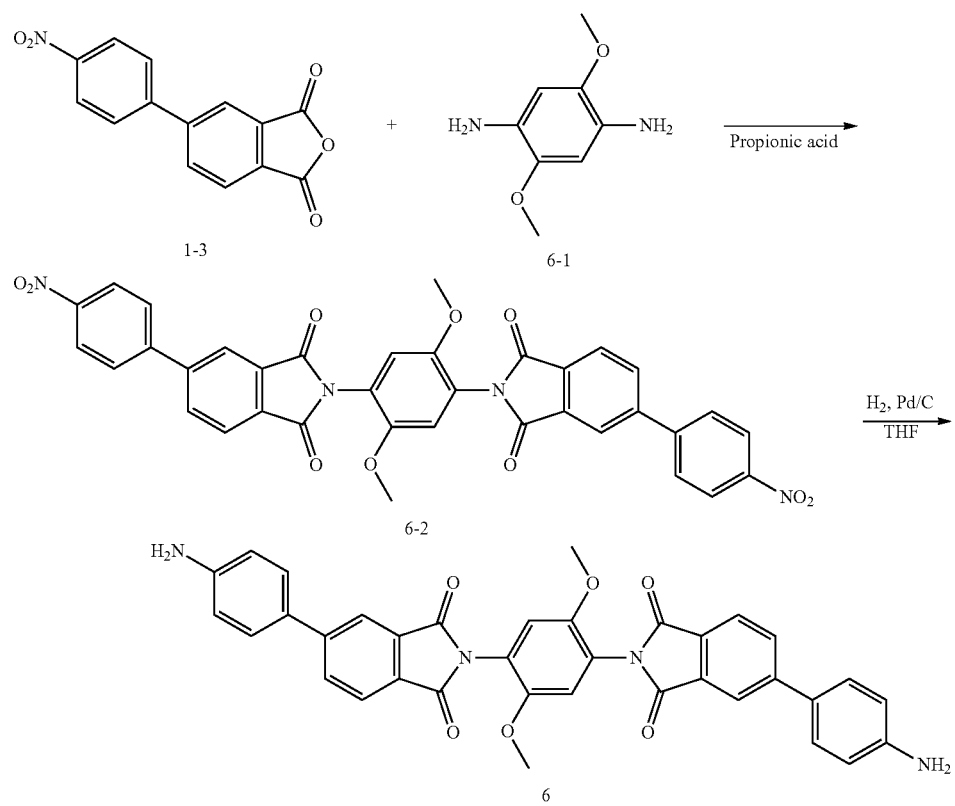

Preparation of Compound 6-2

Compound 1-3 (20.0 g, 74.3 mmol) and compound 6-1 (6.24 g, 37.1 mmol) were added to propionic acid (500 mL) with reflux and stirred for 12 hours. After completion of the reaction, the reaction mixture was cooled to room temperature, and ethanol (500 mL) was added to disperse the resulting solid. After filtering the reaction mixture, the obtained solid was washed with water and ethanol (1:1, volume ratio) to obtain compound 6-2 (23.6 g, yield 95%).

Preparation of Compound 6

Compound 6-2 (23.6 g, 35.3 mmol) was dissolved in THF (200 mL), and a Pd/C catalyst was added, followed by heating to 60° C. The reaction mixture was stirred for 4

<Synthesis Example 7> Preparation of Compound 7

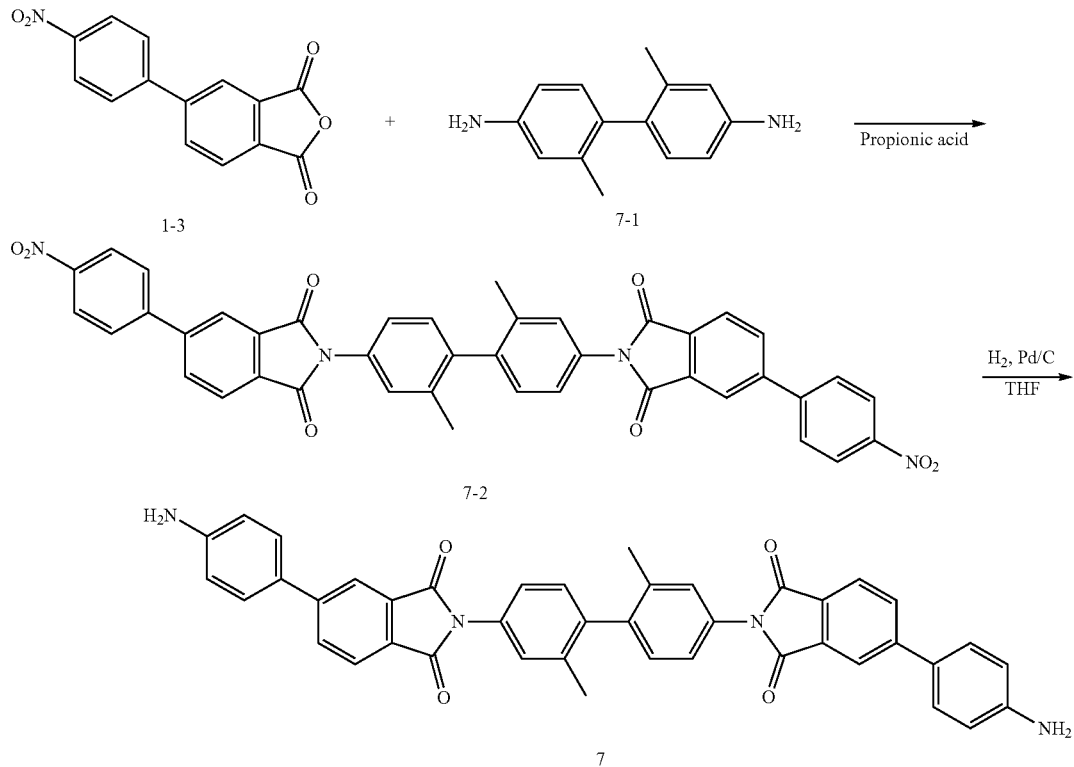

Preparation of Compound 7-2

Compound 1-3 (20.0 g, 74.3 mmol) and compound 7-1 (7.88 g, 37.1 mmol) were added to propionic acid (500 mL) with reflux and stirred for 12 hours. After completion of the reaction, the reaction mixture was cooled to room temperature, and ethanol (500 mL) was added to disperse the resulting solid. After filtering the reaction mixture, the obtained solid was washed with water and ethanol (1:1, volume ratio) to obtain compound 7-2 (23.6 g, yield 89%).

Preparation of Compound 7

Compound 7-2 (23.6 g, 33.0 mmol) was dissolved in THF (200 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (200 mL) to obtain compound 7 (19.9 g, yield 92%).

HR LC/MS/MS m/z calcd for $C_{42}H_{30}N_4O_4$ (M+): 654.2267; found: 654.2264

<Synthesis Example 8> Preparation of Compound 8

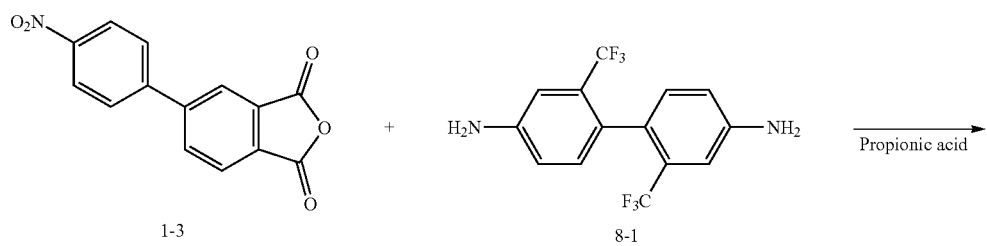

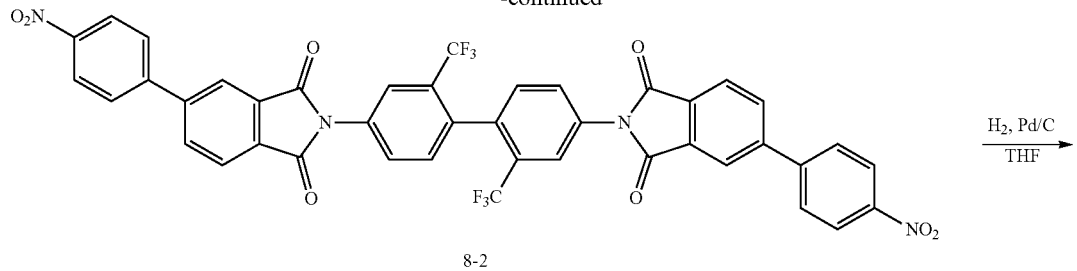

8-2

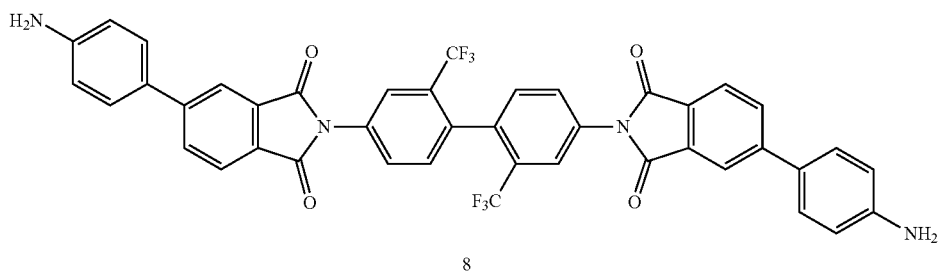

8

Preparation of Compound 8-2

Compound 1-3 (20.0 g, 74.3 mmol) and compound 8-1 (11.8 g, 37.1 mmol) were added to propionic acid (500 mL) with reflux and stirred for 12 hours. After completion of the reaction, the reaction mixture was cooled to room temperature, and ethanol (500 mL) was added to disperse the resulting solid. After filtering the reaction mixture, the obtained solid was washed with water and ethanol (1:1, volume ratio) to obtain compound 8-2 (29.3 g, yield 96%).

Preparation of Compound 8

Compound 8-2 (29.3 g, 35.6 mmol) was dissolved in THF (200 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (250 mL) to obtain compound 8 (24.2 g, yield 89%).

HR LC/MS/MS m/z calcd for $C_{42}H_{24}F_6N_4O_4$ (M+): 762.1702; found: 762.1700

<Synthesis Example 9> Preparation of Compound 9

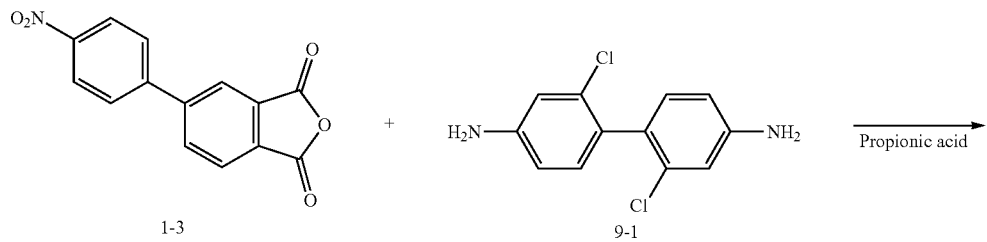

1-3     9-1

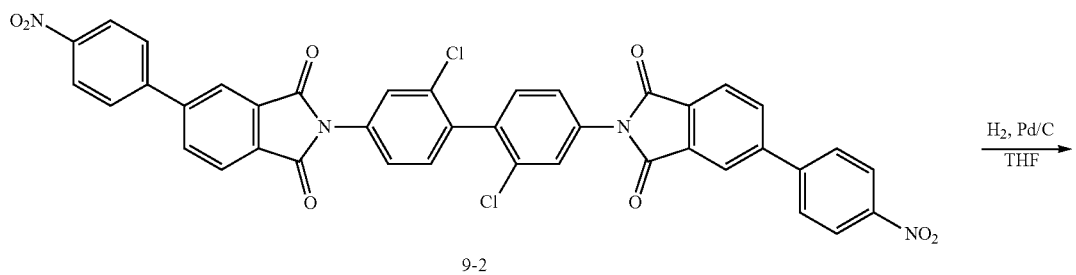

9-2

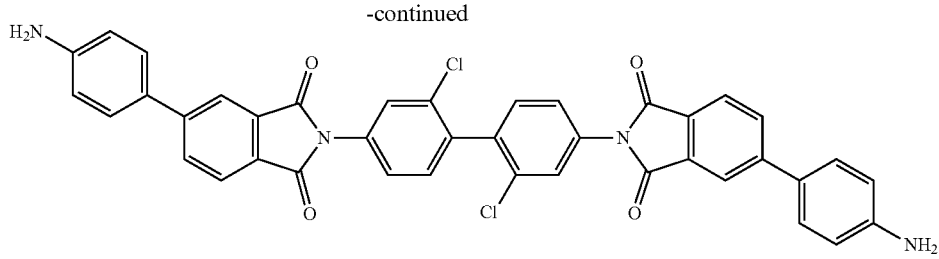

9

Preparation of Compound 9-2

Compound 1-3 (20.0 g, 74.3 mmol) and compound 9-1 (11.8 g, 37.1 mmol) were added to propionic acid (500 mL) with reflux and stirred for 12 hours. After completion of the reaction, the reaction mixture was cooled to room temperature, and ethanol (250 mL) was added to disperse the resulting solid. After filtering the reaction mixture, the obtained solid was washed with water and ethanol (1:1, volume ratio) to obtain compound 9-2 (29.3 g, yield 96%).

Preparation of Compound 9

Compound 9-2 (29.3 g, 35.6 mmol) was dissolved in THF (200 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (250 mL) to obtain compound 9 (22.0 g, yield 89%).

HR LC/MS/MS m/z calcd for $C_{40}H_{24}C_{12}N_4O_4$ (M+): 694.1175; found: 694.1172

<Synthesis Example 10> Preparation of Compound 10

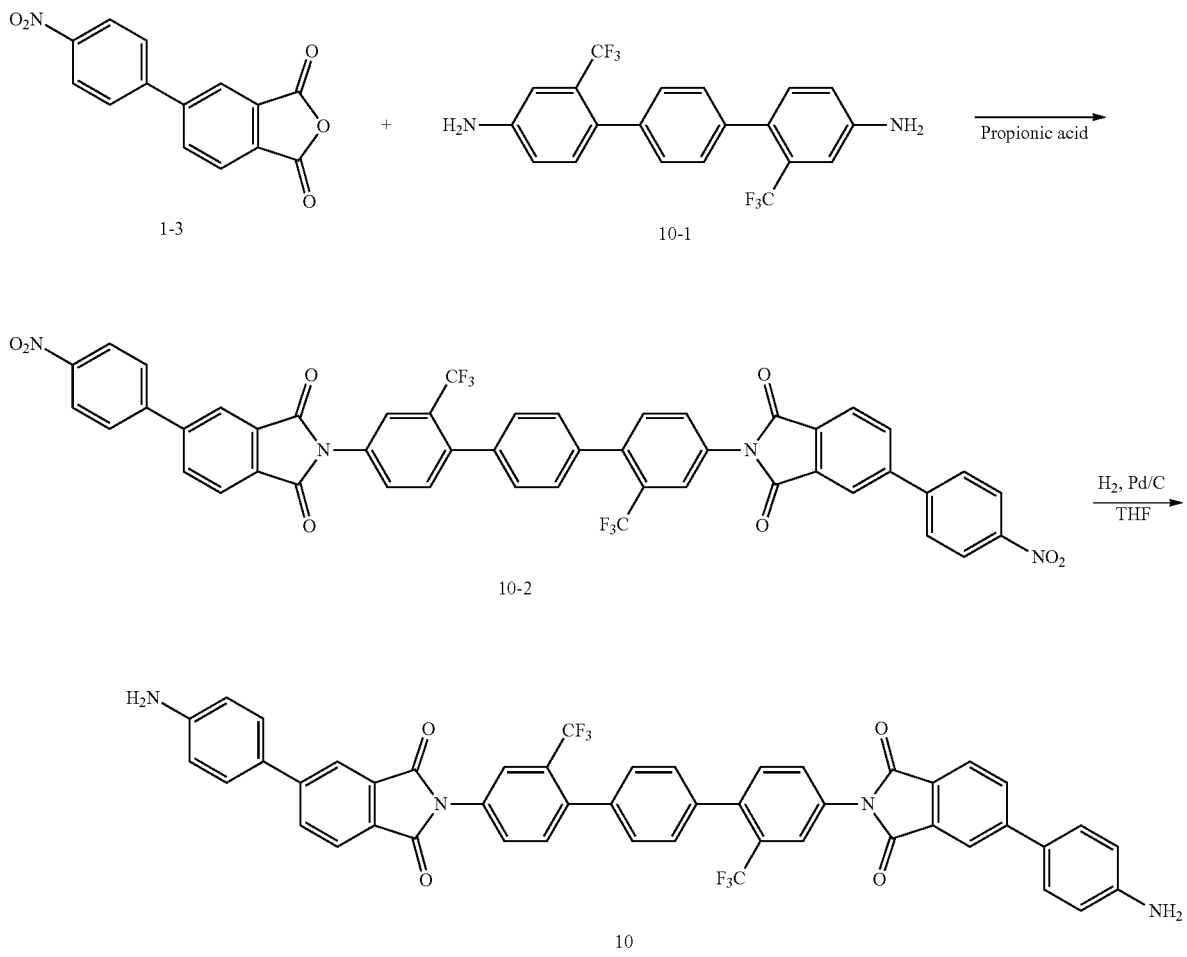

Preparation of Compound 10-2

Compound 1-3 (20.0 g, 74.3 mmol) and compound 10-1 (14.7 g, 37.1 mmol) were added to propionic acid (500 mL) with reflux and stirred for 12 hours. After completion of the reaction, the reaction mixture was cooled to room temperature, and ethanol (500 mL) was added to disperse the resulting solid. After filtering the reaction mixture, the obtained solid was washed with water and ethanol (1:1, volume ratio) to obtain compound 10-2 (32.7 g, yield 98%).

Preparation of Compound 10

Compound 10-2 (32.7 g, 36.4 mmol) was dissolved in THF (200 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (300 mL) to obtain compound 10 (27.4 g, yield 90%).

HR LC/MS/MS m/z calcd for $C_{48}H_{28}F_6N_4O_4$ (M+): 838.2015; found: 838.2011

<Synthesis Example 11> Preparation of Compound 11

Preparation of Compound 11-3

Compound 11-1 (20 g, 85.4 mmol) and compound 1-2 (9.7 g, 42.7 mmol) were dissolved in THF (500 mL) in a nitrogen atmosphere, and potassium carbonate (11.8 g, 85.4 mmol) was dissolved in water (250 mL), and then heated to 100° C. Palladium tetratriphenylphosphine (1.48 g) was added to the reaction mixture with reflux and stirred for 12 hours. After completion of the reaction, the reaction mixture was cooled to room temperature, and then ethyl acetate (250 mL) was added to separate an organic layer. The separated organic layer was dried over anhydrous magnesium sulfate, and the solvent was removed through a vacuum distillation apparatus to obtain compound 11-3 (11.5 g, yield 80%).

Preparation of Compound 11-5

Compound 11-3 (11.5 g, 34.1 mmol) and compound 11-4 (4.1 g, 17.1 mmol) were added to propionic acid (500 mL) with reflux and stirred for 12 hours. After completion of the reaction, the reaction mixture was cooled to room temperature, and ethanol (500 mL) was added to disperse the resulting solid. After filtering the reaction mixture, the obtained solid was washed with water and ethanol (1:1, volume ratio) to obtain compound 11-5 (14.4 g, yield 96%).

Preparation of Compound 11

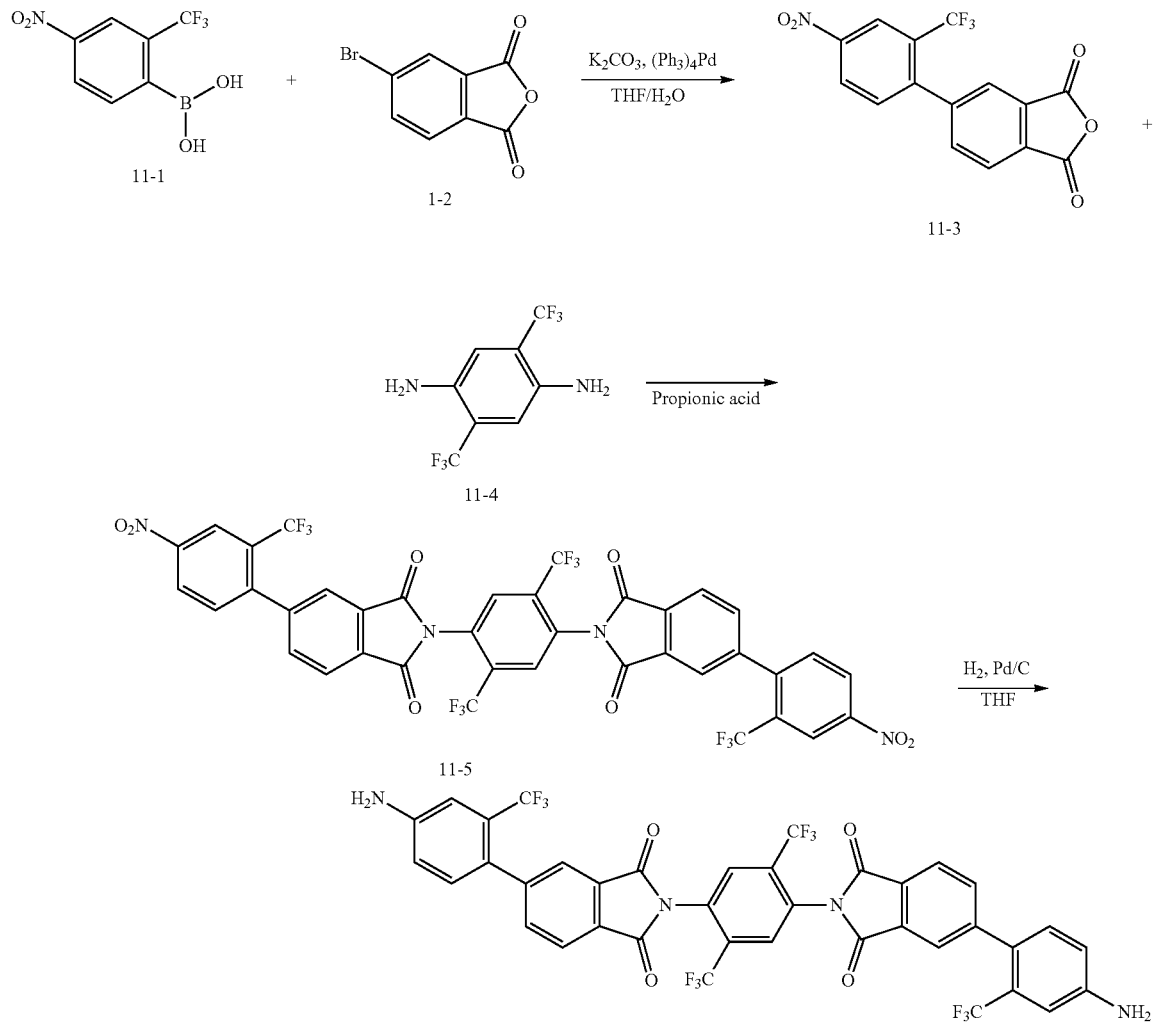

Compound 11-5 (14.4 g, 16.3 mmol) was dissolved in THF (200 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (150 mL) to obtain compound 11 (12.7 g, yield 95%).

HR LC/MS/MS m/z calcd for $C_{38}H_{18}F_{12}N_4O_4$ (M+): 822.1136; found: 822.1131

<Synthesis Example 12> Preparation of Compound 12 separated organic layer was dried over anhydrous magnesium sulfate, and the solvent was removed through a vacuum distillation apparatus to obtain compound 12-3 (24.1 g, yield 77%).

Preparation of Compound 12-5

Compound 12-3 (24.1 g, 58.4 mmol) and compound 12-4 (13.6 g, 42.7 mmol) were added to propionic acid (500 mL) with reflux and stirred for 12 hours. After completion of the reaction, the reaction mixture was cooled to room temperature, and ethanol (500 mL) was added to disperse the resulting solid. After filtering the reaction mixture, the obtained solid was washed with water and ethanol (1:1, volume ratio) to obtain compound 12-5 (32.6 g, yield 90%).

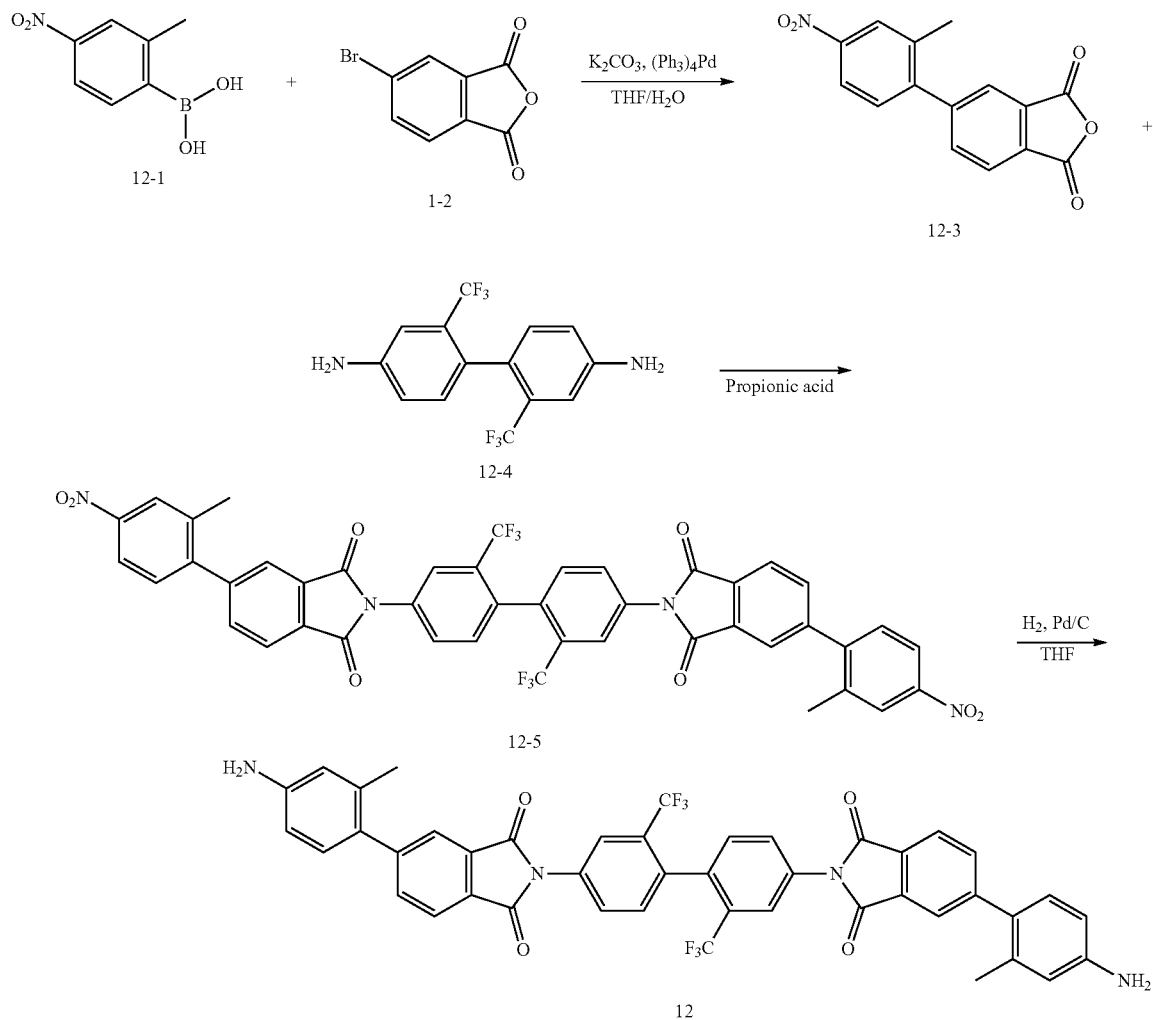

Preparation of Compound 12-3

Compound 12-1 (30 g, 166.6 mmol) and compound 1-2 (25.2 g, 111.1 mmol) were dissolved in THF (500 mL) in a nitrogen atmosphere, and potassium carbonate (23.0 g, 166.6 mmol) was dissolved in water (250 mL), and then heated to 100° C. Palladium tetratriphenylphosphine (3.84 g) was added to the reaction mixture with reflux and stirred for 12 hours. After completion of the reaction, the reaction mixture was cooled to room temperature, and then ethyl acetate (250 mL) was added to separate an organic layer. The Preparation of Compound 12

Compound 12-5 (32.6 g, 38.4 mmol) was dissolved in THF (200 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (250 mL) to obtain compound 12 (24.3 g, yield 80%).

HR LC/MS/MS m/z calcd for $C_{44}H_{28}F_6N_4O_4$ (M+): 790.2015; found: 790.2012

<Synthesis Example 13> Preparation of Compound 13

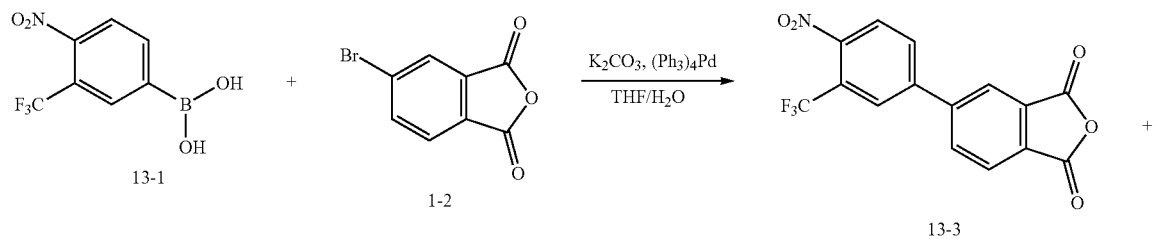

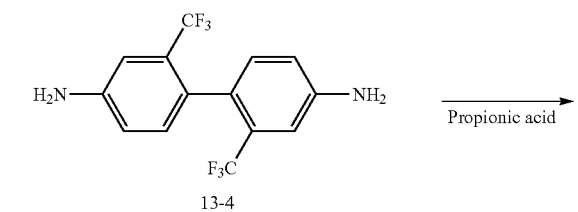

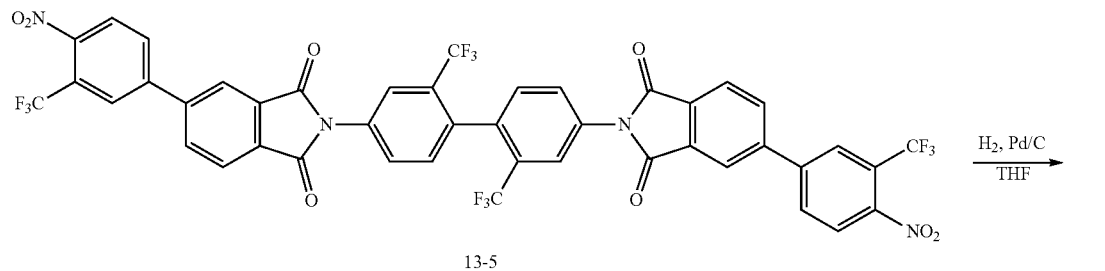

Preparation of Compound 13-3

Compound 13-1 (30 g, 128.2 mmol) and compound 1-2 (19.4 g, 85.4 mmol) were dissolved in THF (500 mL) in a nitrogen atmosphere, and potassium carbonate (17.7 g, 128.2 mmol) was dissolved in water (250 mL), and then heated to 100° C. Palladium tetratriphenylphosphine (2.96 g) was added to the reaction mixture with reflux and stirred for 12 hours. After completion of the reaction, the reaction mixture was cooled to room temperature, and then ethyl acetate (250 mL) was added to separate an organic layer. The separated organic layer was dried over anhydrous magnesium sulfate, and the solvent was removed through a vacuum distillation apparatus to obtain compound 13-3 (22.1 g, yield 77%).

Preparation of Compound 13-5

Compound 13-3 (22.1 g, 65.8 mmol) and compound 13-4 (10.5 g, 32.9 mmol) were added to propionic acid (500 mL) with reflux and stirred for 12 hours. After completion of the reaction, the reaction mixture was cooled to room temperature, and ethanol (500 mL) was added to disperse the resulting solid. After filtering the reaction mixture, the obtained solid was washed with water and ethanol (1:1, volume ratio) to obtain compound 13-5 (28.9 g, yield 92%).

Preparation of Compound 13

Compound 13-5 (28.9 g, 30.2 mmol) was dissolved in THF (200 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (250 mL) to obtain compound 13 (25.8 g, yield 95%).

HR LC/MS/MS m/z calcd for $C_{44}H_{22}F_{12}N_4O_4$ (M+): 898.1449; found: 898.1444

<Synthesis Example 14> Preparation of Compound 14

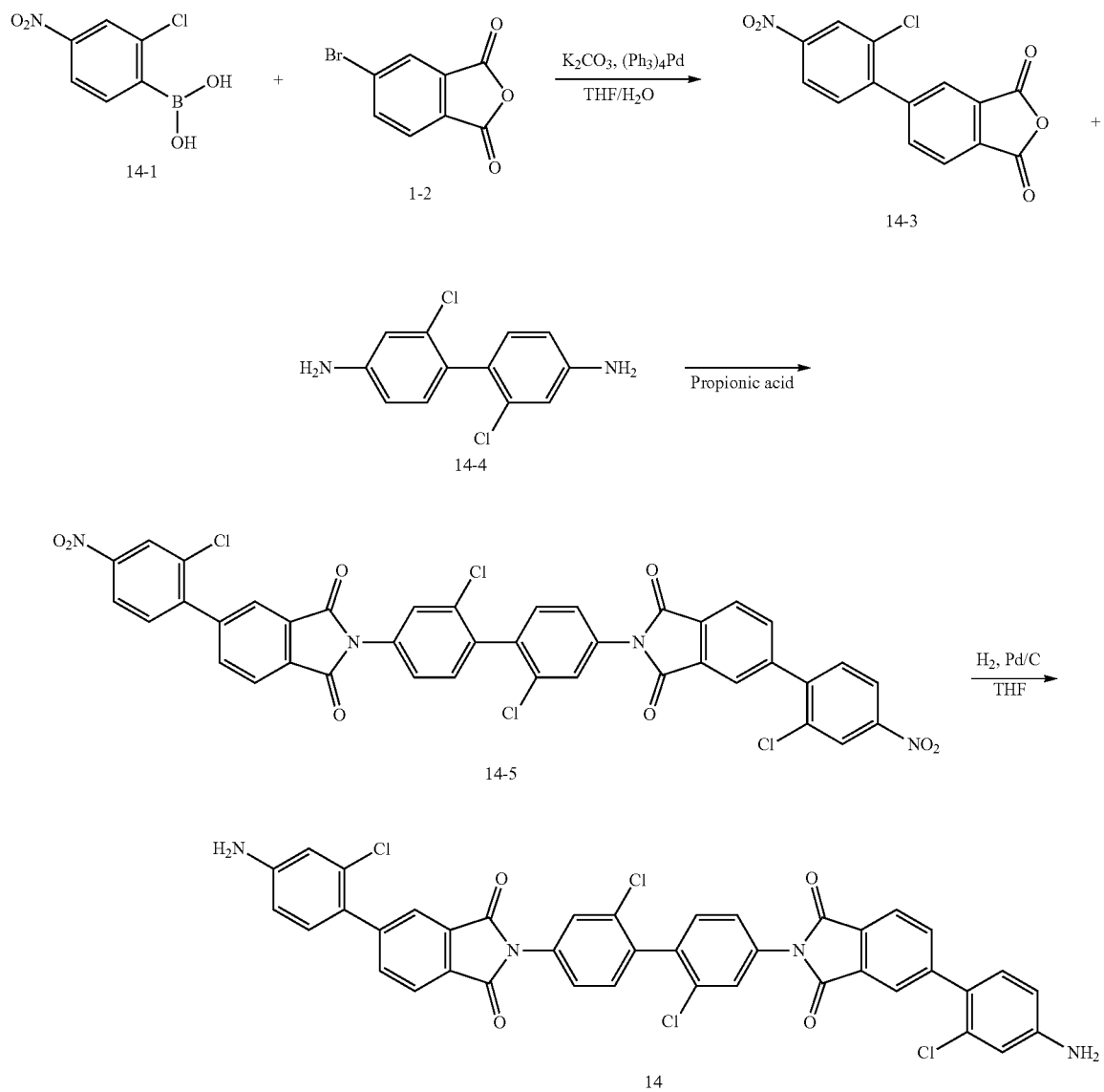

Preparation of Compound 14-3

Compound 14-1 (30 g, 149.2 mmol) and compound 1-2 (22.5 g, 99.5 mmol) were dissolved in THF (500 mL) in a nitrogen atmosphere, and potassium carbonate (20.6 g, 149.2 mmol) was dissolved in water (250 mL), and then heated to 100° C. Palladium tetratriphenylphosphine (3.43 g) was added to the reaction mixture with reflux and stirred for 12 hours. After completion of the reaction, the reaction mixture was cooled to room temperature, and then ethyl acetate (250 mL) was added to separate an organic layer. The separated organic layer was dried over anhydrous magnesium sulfate, and the solvent was removed through a vacuum distillation apparatus to obtain compound 14-3 (26.4 g, yield 88%).

Preparation of Compound 14-5

Compound 14-3 (26.4 g, 87.2 mmol) and compound 14-4 (11.0 g, 43.6 mmol) were added to propionic acid (500 mL) with reflux and stirred for 12 hours. After completion of the reaction, the reaction mixture was cooled to room temperature, and ethanol (500 mL) was added to disperse the resulting solid. After filtering the reaction mixture, the obtained solid was washed with water and ethanol (1:1, volume ratio) to obtain compound 14-5 (33.4 g, yield 93%).

Preparation of Compound 14

Compound 14-5 (33.4 g, 40.5 mmol) was dissolved in THF (200 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (300 mL) to obtain compound 14 (26.9 g, yield 87%).

HR LC/MS/MS m/z calcd for $C_{40}H_{22}Cl_4N_4O_4$ (M+): 764.0366; found: 764.0363

<Synthesis Example 15> Preparation of Compound 15

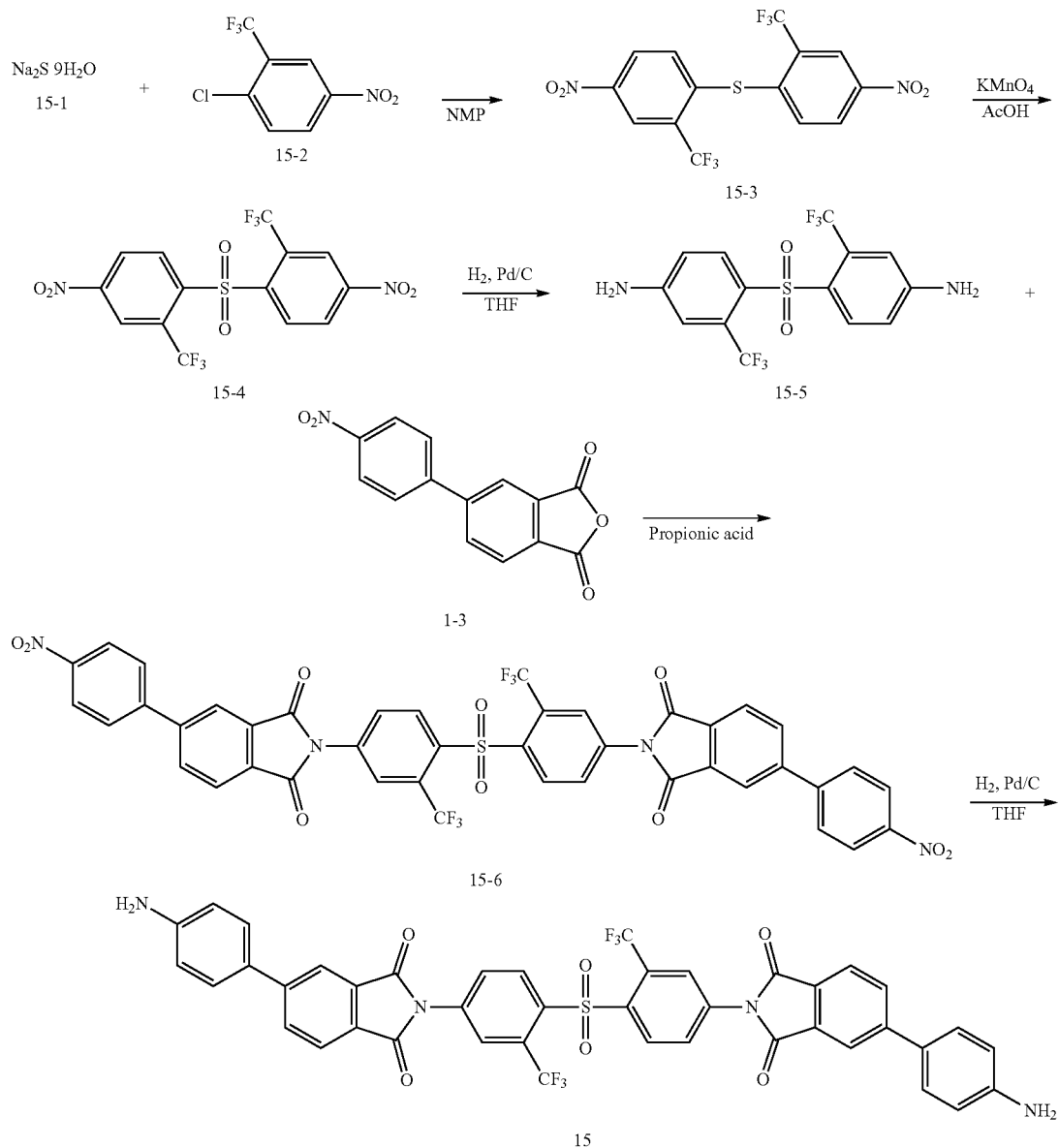

Preparation of Compound 15-3

Compound 15-2 (50.0 g, 0.22 mmol) was dissolved in N-methylpyrrolidone (NMP) (500 mL), and compound 15-1 (26.6 g, 0.11 mol) was added in several portions, and then heated to 140° C. and stirred for 6 hours. After completion of the reaction, water (1000 mL) was added to the reaction mixture and filtered to obtain a solid. The obtained solid was washed with water and ethanol (1:1, volume ratio) to obtain compound 15-3 (19.6 g, yield 43%).

Preparation of Compound 15-4

After dispersing compound 15-3 (19.6 g, 47.7 mmol) in glacial acetic acid (300 mL), potassium permanganate (18.8 g, 119 mmol) was added at 0° C. and stirred for 1 hour, then warmed to room temperature and stirred for 6 hours. After completion of the reaction, water (600 mL) was added to the reaction mixture and filtered to obtain a solid. The obtained solid was recrystallized from ethanol (300 mL) to obtain compound 15-4 (19.4 g, yield 92%).

Preparation of Compound 15-5

Compound 15-4 (19.4 g, 43.7 mmol) was dissolved in THF (200 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (150 mL) to obtain compound 15-5 (14.9 g, yield 89%).

Preparation of Compound 15-6

Compound 15-5 (14.9 g, 38.9 mmol) and compound 1-3 (20.9 g, 77.9 mmol) were added to propionic acid (500 mL)

with reflux and stirred for 12 hours. After completion of the reaction, the reaction mixture was cooled to room temperature, and ethanol (500 mL) was added to disperse the resulting solid. After filtering the reaction mixture, the obtained solid was washed with water and ethanol (1:1, volume ratio) to obtain compound 15-6 (33.3 g, yield 97%).

Preparation of Compound 15

Compound 15-6 (33.3 g, 37.6 mmol) was dissolved in THF (400 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (300 mL) to obtain compound 15 (28.2 g, yield 91%).

HR LC/MS/MS m/z calcd for $C_{42}H_{24}F_6SN_4O_6$ (M+): 826.1321; found: 826.1319

<Synthesis Example 16> Preparation of Compound 16

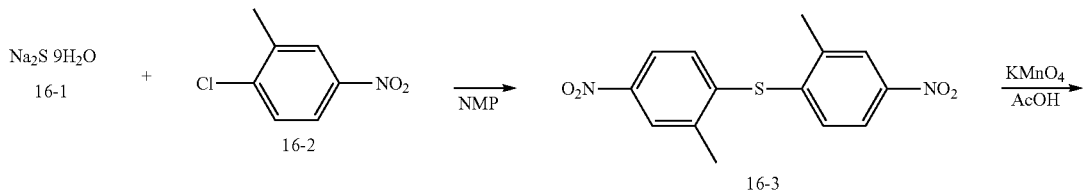

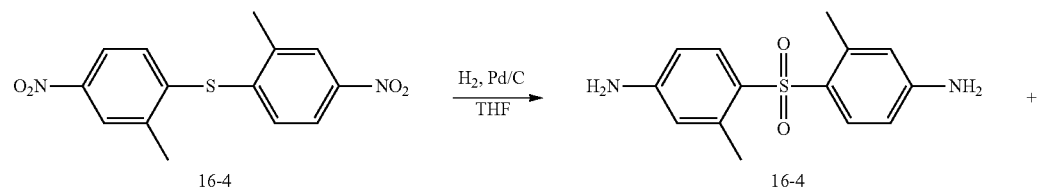

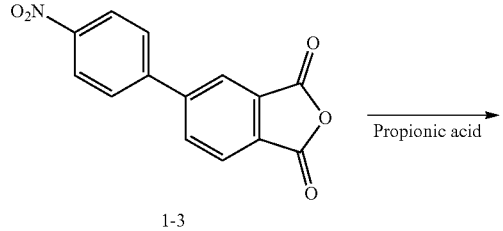

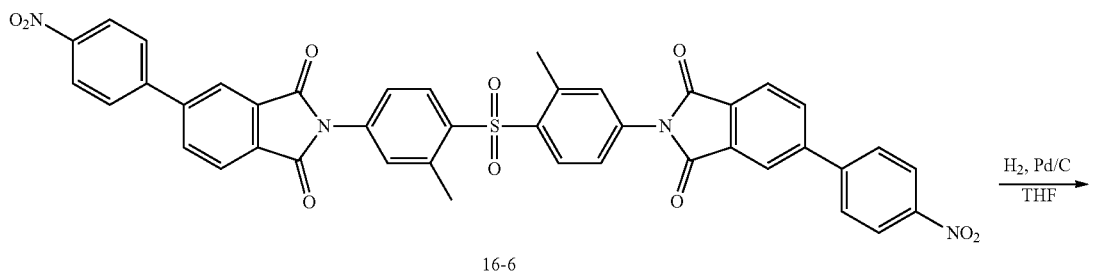

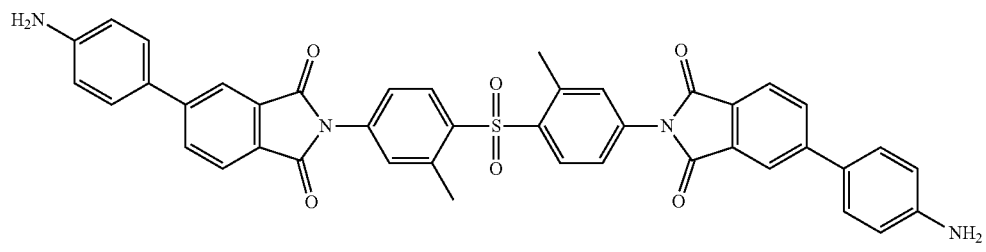

Preparation of Compound 16-3

Compound 16-2 (42.7 g, 0.25 mmol) was dissolved in NMP (500 mL), and compound 16-1 (30.0 g, 0.12 mol) was added in several portions, and then heated to 140° C. and stirred for 6 hours. After completion of the reaction, water (1000 mL) was added to the reaction mixture and filtered to obtain a solid, and the obtained solid was washed with water and ethanol (1:1, volume ratio) to obtain compound 16-3 (20.5 g, yield 54%).

Preparation of Compound 16-4

After dispersing compound 16-3 (20.5 g, 67.5 mmol) in glacial acetic acid (300 mL), potassium permanganate (26.6 g, 168.7 mmol) was added at 0° C. and stirred for 1 hour, then warmed to room temperature and stirred for 6 hours. After completion of the reaction, water (600 mL) was added to the reaction mixture and filtered to obtain a solid. The obtained solid was recrystallized from ethanol (200 mL) to obtain compound 16-4 (19.7 g, yield 87%).

Preparation of Compound 16-5

Compound 16-4 (19.7 g, 58.6 mmol) was dissolved in THF (200 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (150 mL) to obtain compound 16-5 (14.7 g, yield 91%).

Preparation of Compound 16-6

Compound 16-5 (14.7 g, 53.3 mmol) and compound 1-3 (28.7 g, 106.7 mmol) were added to propionic acid (500 mL) with reflux and stirred for 12 hours. After completion of the reaction, the reaction mixture was cooled to room temperature, and ethanol (500 mL) was added to disperse the resulting solid. After filtering the reaction mixture, the obtained solid was washed with water and ethanol (1:1, volume ratio) to obtain compound 16-6 (39.4 g, yield 95%).

Preparation of Compound 16

Compound 16-6 (39.4 g, 50.7 mmol) was dissolved in THF (500 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (350 mL) to obtain compound 16 (33.8 g, yield 93%).

HR LC/MS/MS m/z calcd for $C_{42}H_{30}SN_4O_6$ (M+): 718.1886; found: 718.1883

<Synthesis Example 17> Preparation of Compound 17

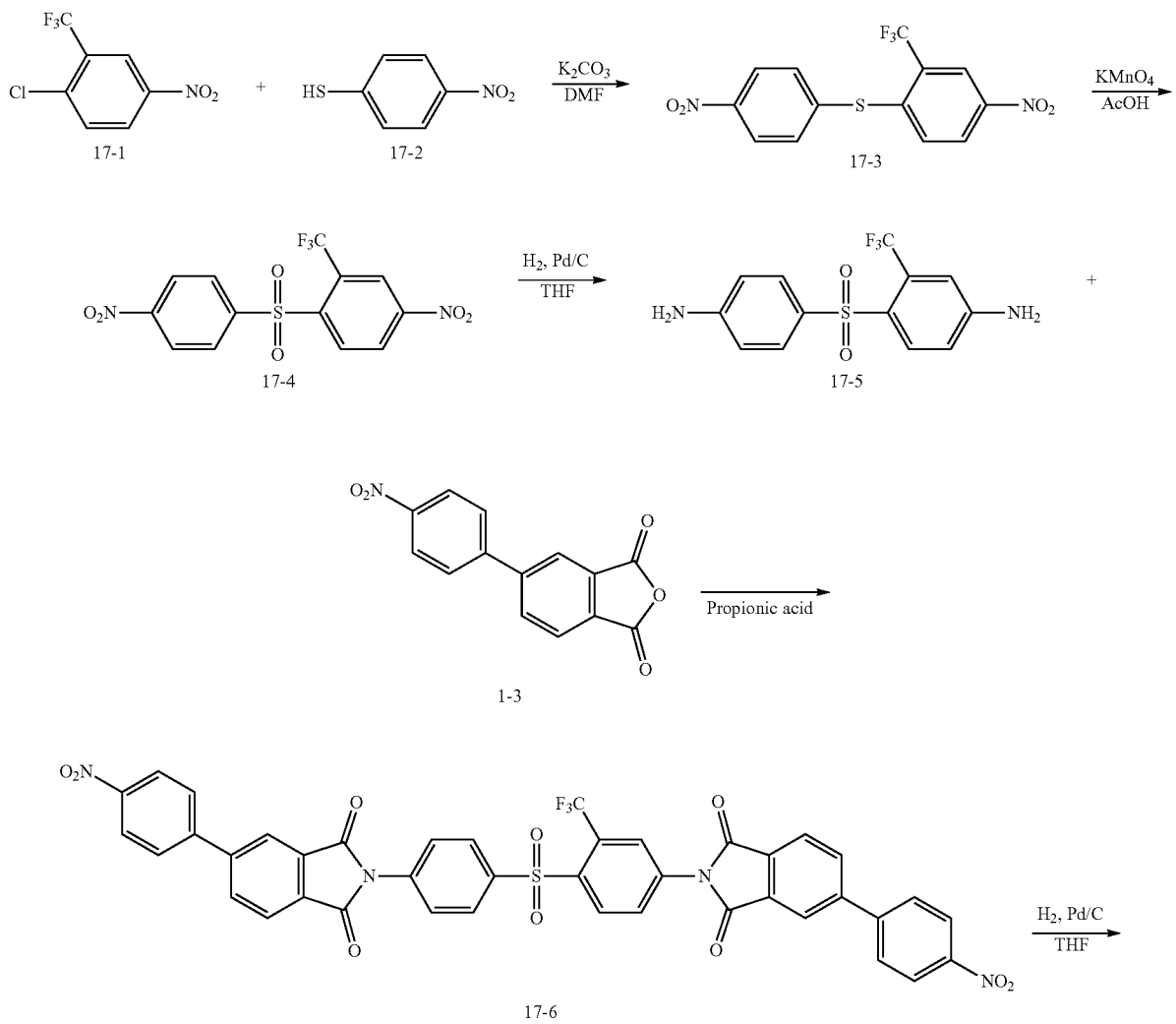

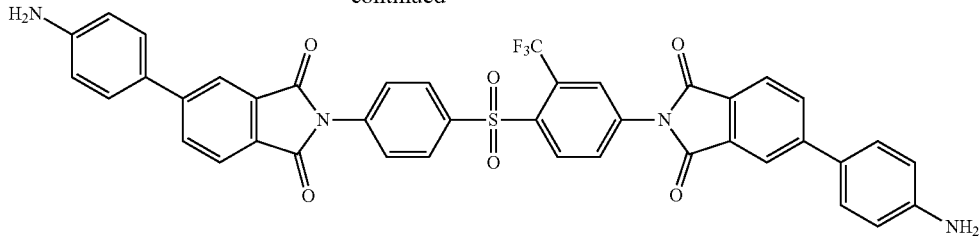

17

Preparation of Compound 17-3

Compound 17-1 (30.0 g, 0.13 mol) and compound 17-2 (31.0 g, 0.2 mol) were dissolved in dimethylformamide (DMF) (600 mL) and potassium carbonate was added, followed by heating to 150° C. After completion of the reaction, water (1000 mL) was added to the reaction mixture and filtered to obtain a solid. The obtained solid was recrystallized from ethanol (350 mL) to obtain compound 17-3 (34.8 g, yield 76%).

Preparation of Compound 17-4

After dispersing compound 17-3 (34.8 g, 101.3 mmol) in glacial acetic acid (400 mL), potassium permanganate (40.0 g, 253.3 mmol) was added at 0° C. and stirred for 1 hour, then warmed to room temperature and stirred for 6 hours. After completion of the reaction, water (800 mL) was added to the reaction mixture and filtered to obtain a solid. The obtained solid was recrystallized from ethanol (300 mL) to obtain compound 17-4 (32.3 g, yield 85%).

Preparation of Compound 17-5

Compound 17-4 (32.3 g, 85.9 mmol) was dissolved in THF (300 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol to obtain compound 17-5 (25.8 g, yield 95%).

Preparation of Compound 17-6

Compound 17-5 (25.8 g, 81.6 mmol) and compound 1-3 (43.9 g, 163.3 mmol) were added to propionic acid (500 mL) with reflux and stirred for 12 hours. After completion of the reaction, the reaction mixture was cooled to room temperature, and ethanol (500 mL) was added to disperse the resulting solid. After filtering the reaction mixture, the obtained solid was washed with water and ethanol (1:1, volume ratio) to obtain compound 17-6 (58.7 g, yield 88%).

Preparation of Compound 17

Compound 17-6 (58.7 g, 71.8 mmol) was dissolved in THF (600 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (500 mL) to obtain compound 17 (50.1 g, yield 92%).

HR LC/MS/MS m/z calcd for $C_{41}H_{25}F_3SN_4O_6$ (M+): 758.1447; found: 758.1443

<Synthesis Example 18> Preparation of Compound 18

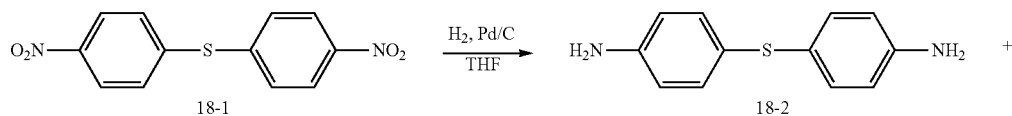

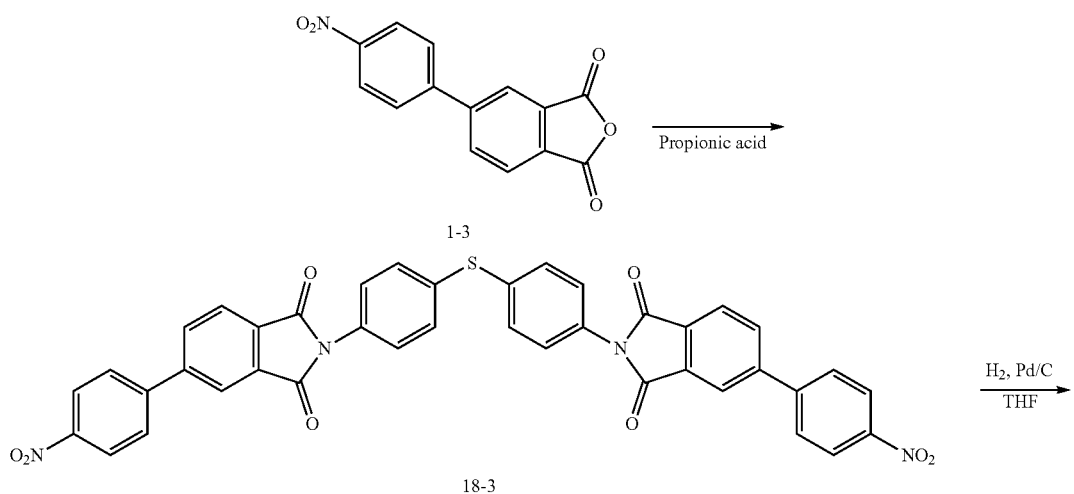

-continued

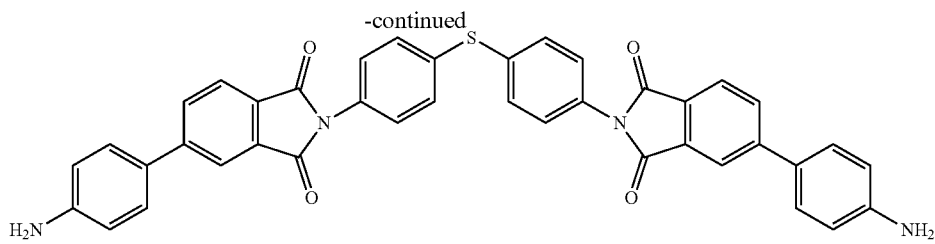

18

Preparation of Compound 18-2

Compound 18-1 (15.0 g, 54.3 mmol) was dissolved in THF (200 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (100 mL) to obtain compound 18-2 (11.0 g, yield 94%).

Preparation of Compound 18-3

Compound 18-2 (11.0 g, 51.0 mmol) and compound 1-3 (27.4 g, 102.1 mmol) were added to propionic acid (400 mL) with reflux and stirred for 12 hours. After completion of the reaction, the reaction mixture was cooled to room temperature, and ethanol (400 mL) was added to disperse the resulting solid. After filtering the reaction mixture, the obtained solid was washed with water and ethanol (1:1, volume ratio) to obtain compound 18-3 (31.5 g, yield 86%).

Preparation of Compound 18

Compound 18-3 (31.5 g, 43.9 mmol) was dissolved in THF (300 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (250 mL) to obtain compound 18 (26.5 g, yield 93%).

HR LC/MS/MS m/z calcd for $C_{40}H_{26}SN_4O_4$ (M+): 658.1675; found: 658.1670

<Synthesis Example 19> Preparation of Compound 19

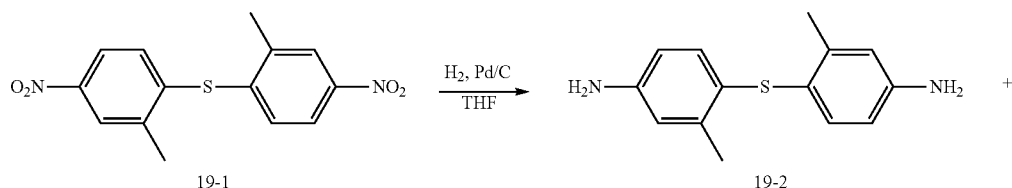

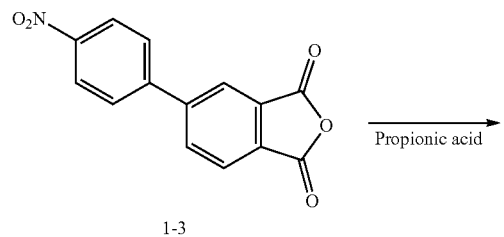

1-3

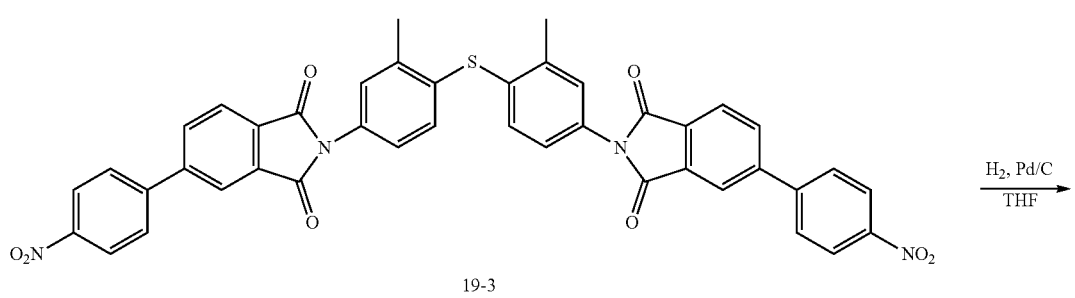

19-3

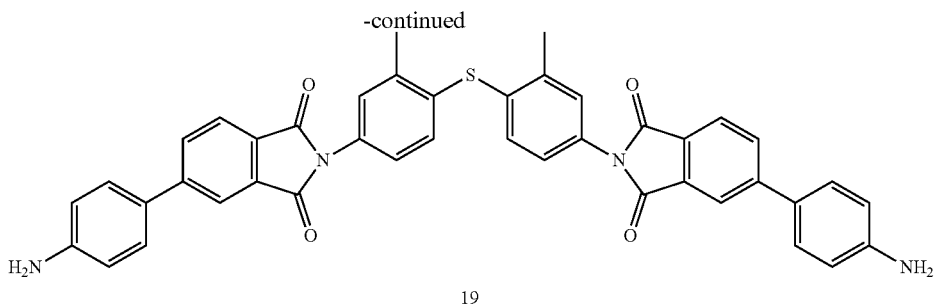

19

Preparation of Compound 19-2

Compound 19-1 (15.0 g, 49.3 mmol) was dissolved in THF (200 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (110 mL) to obtain compound 19-2 (11.7 g, yield 98%).

Preparation of Compound 19-3

Compound 19-2 (11.7 g, 48.3 mmol) and compound 1-3 (26.0 g, 96.7 mmol) were added to propionic acid (400 mL) with reflux and stirred for 12 hours. After completion of the reaction, the reaction mixture was cooled to room temperature, and ethanol (400 mL) was added to disperse the resulting solid. After filtering the reaction mixture, the obtained solid was washed with water and ethanol (1:1, volume ratio) to obtain compound 19-3 (34.9 g, yield 97%).

Preparation of Compound 19

Compound 19-3 (34.9 g, 46.9 mmol) was dissolved in THF (400 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (300 mL) to obtain compound 19 (27.3 g, yield 85%).

HR LC/MS/MS m/z calcd for $C_{42}H_{30}SN_4O_4$ (M+): 686.1988; found: 686.1986

<Synthesis Example 20> Preparation of Compound 20

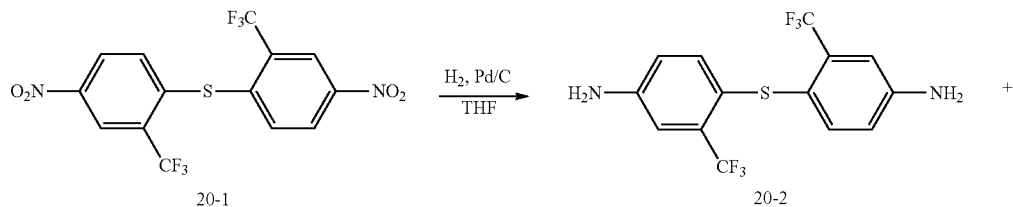

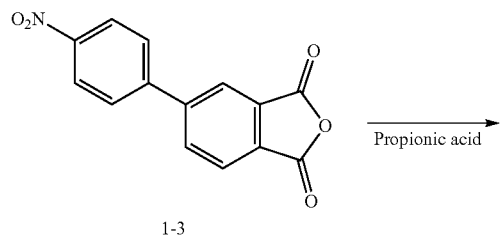

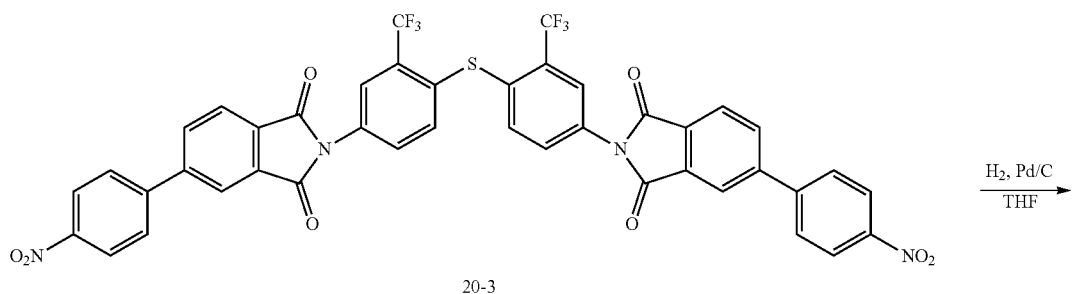

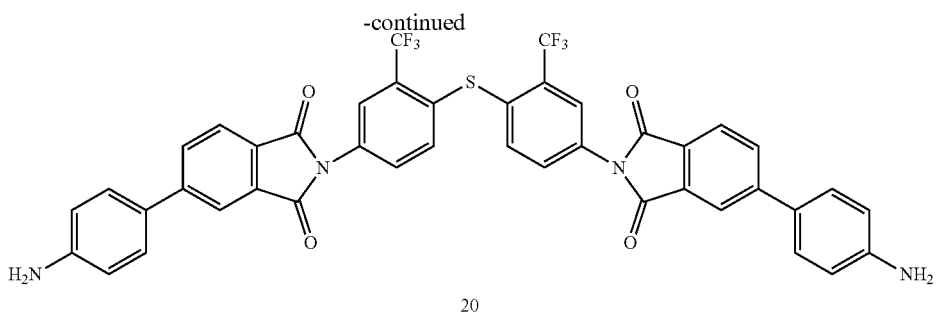

20

Preparation of Compound 20-2

Compound 20-1 (15.0 g, 36.4 mmol) was dissolved in THF (200 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (150 mL) to obtain compound 20-2 (12.1 g, yield 95%).

Preparation of Compound 20-3

Compound 20-2 (12.1 g, 34.5 mmol) and compound 1-3 (18.6 g, 69.1 mmol) were added to propionic acid (300 mL) with reflux and stirred for 12 hours. After completion of the reaction, the reaction mixture was cooled to room temperature, and ethanol (300 mL) was added to disperse the resulting solid. After filtering the reaction mixture, the obtained solid was washed with water and ethanol (1:1, volume ratio) to obtain compound 20-3 (26.5 g, yield 90%).

Preparation of Compound 20

Compound 20-3 (26.5 g, 31.1 mmol) was dissolved in THF (300 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (250 mL) to obtain compound 20 (22.4 g, yield 91%).

HR LC/MS/MS m/z calcd for $C_{42}H_{24}F_6SN_4O_4$ (M+): 794.1422; found: 794.1419

<Synthesis Example 21> Preparation of Compound 21

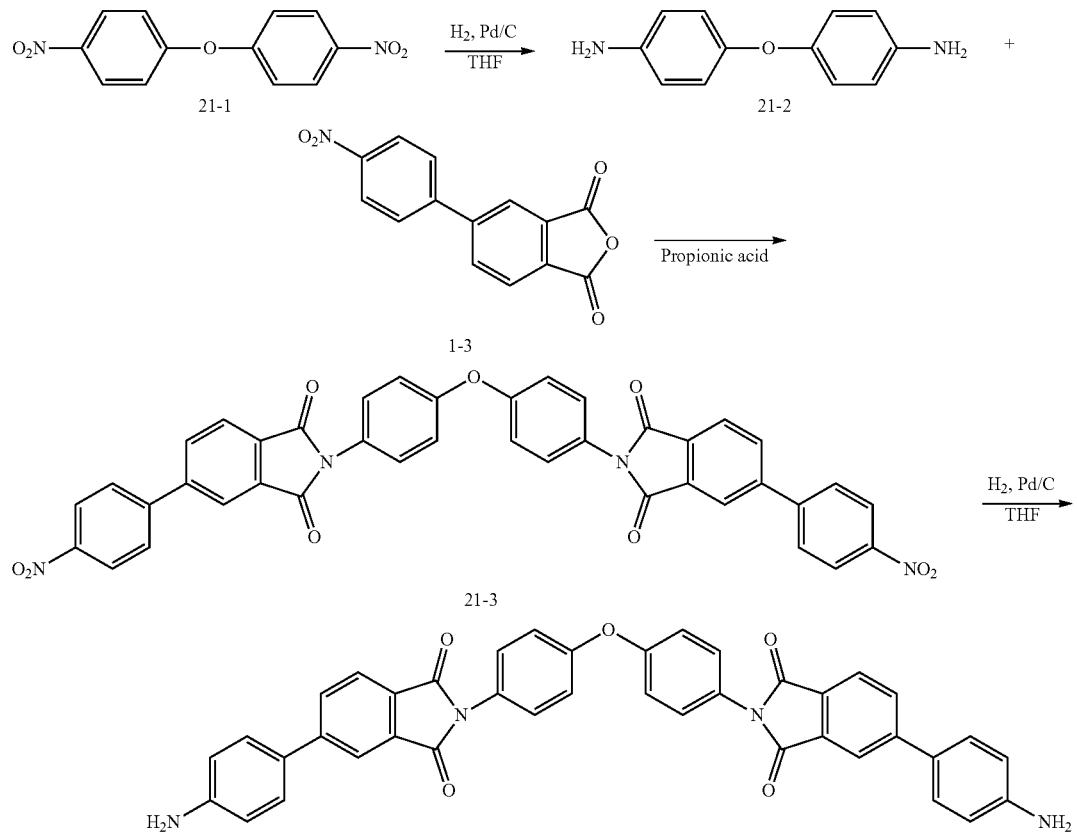

Preparation of Compound 21-2

Compound 21-1 (15.0 g, 57.6 mmol) was dissolved in THF (200 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (100 mL) to obtain compound 21-2 (10.6 g, yield 92%).

Preparation of Compound 21-3

Compound 21-2 (10.6 g, 53.0 mmol) and compound 1-3 (28.5 g, 106.1 mmol) were added to propionic acid (400 mL) with reflux and stirred for 12 hours. After completion of the reaction, the reaction mixture was cooled to room temperature, and ethanol (400 mL) was added to disperse the resulting solid. After filtering the reaction mixture, the obtained solid was washed with water and ethanol (1:1, volume ratio) to obtain compound 21-3 (36.1 g, yield 97%).

Preparation of Compound 21

Compound 21-3 (36.1 g, 51.4 mmol) was dissolved in THF (300 mL), and a Pd/C catalyst was added, followed by heating to 60° C. The reaction mixture was stirred for 4 hours while injecting hydrogen gas continuously. After completion of the reaction, the reaction mixture was cooled to room temperature and filtered to obtain a solid. The obtained solid was recrystallized from ethanol (300 mL) to obtain compound 21 (29.4 g, yield 89%).

HR LC/MS/MS m/z calcd for $C_{40}H_{26}N_4O_5$ (M+): 642.1903; found: 642.1901

Example 1

An organic solvent, DEAc (N,N-diethylacetamide) (100 mL) was charged into a reactor in a nitrogen stream, and then 24.2 g (0.031 mol) of the diamine compound 8 prepared in Synthesis Example 8 was added to dissolve it while maintaining the reactor temperature at 25° C. To the solution with the compound 8 added, 9.12 g (0.031 mol) of BPDA (biphenyl-tetracarboxylic acid dianhydride) as an acid anhydride was added at the same temperature and stirred for 24 hours to obtain a polyimide precursor composition.

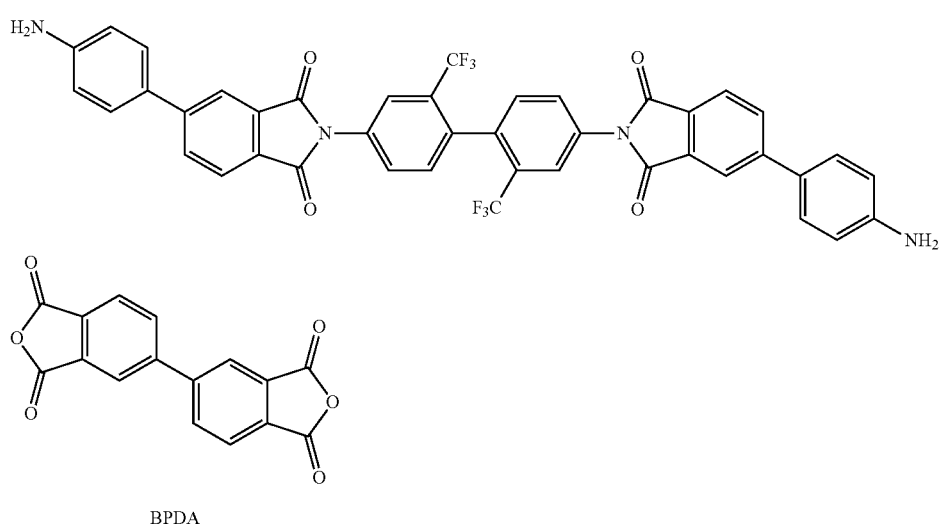

8

BPDA

Example 2

An organic solvent, DEAc (150 mL) was charged into a reactor in a nitrogen stream, and then 33.8 g (0.041 mol) of the diamine compound 15 prepared in Synthesis Example 15 was added to dissolve it while maintaining the reactor temperature at 25° C. To the solution with the compound 15 added, 12.1 g (0.041 mol) of BPDA as an acid anhydride was added at the same temperature and stirred for 24 hours to obtain a polyimide precursor composition.

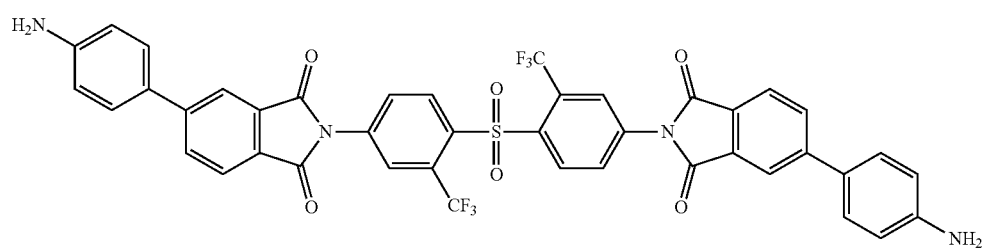

15

Example 3

An organic solvent, DEAc (150 mL) was charged into a reactor in a nitrogen stream, and then 30.5 g (0.040 mol) of the same diamine compound 8 as used in Example 1 was added to dissolve it while maintaining the reactor temperature at 25° C. To the solution with the compound 8 added, 17.7 g (0.040 mol) of 6-FDA (4,4'-(hexafluoroisopropylidene)diphthalic anhydride) as an acid anhydride was added at the same temperature and stirred for 24 hours to obtain a polyimide precursor composition.

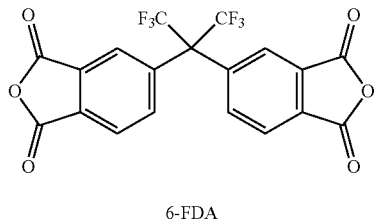 [SMILES: O=C1OC(=O)c2cc(C(c3ccc4c(c3)C(=O)OC4=O)(C(F)(F)F)C(F)(F)F)ccc21]

6-FDA

Example 4

An organic solvent, DEAc (200 mL) was charged into a reactor in a nitrogen stream, and then 37.2 g (0.045 mol) of the same diamine compound 15 as used in Example 2 was added to dissolve it while maintaining the reactor temperature at 25° C. To the solution with the compound 15 added, 20.0 g (0.045 mol) of 6-FDA as an acid anhydride was added at the same temperature and stirred for 24 hours to obtain a polyimide precursor composition.

Comparative Example 1

An organic solvent, DEAc (150 mL) was charged into a reactor in a nitrogen stream, and then 27.8 g (0.087 mol) of TFMB (2,2'-bis(trifluoromethyl)benzidine) as a diamine compound was added to dissolve it while maintaining the reactor temperature at 25° C. To the solution with TFMB added, 25.6 g (0.087 mol) of BPDA as an acid anhydride was added at the same temperature and stirred for 24 hours to obtain a polyimide precursor composition.

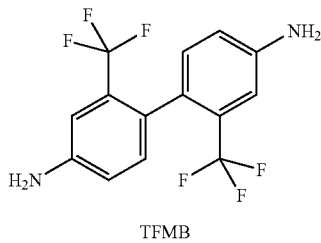 [SMILES: Nc1ccc(-c2ccc(N)cc2C(F)(F)F)c(C(F)(F)F)c1]

TFMB

Comparative Example 2

An organic solvent, DEAc (100 mL) was charged into a reactor in a nitrogen stream, and then 22.4 g (0.070 mol) of TFMB as a diamine compound was added to dissolve it while maintaining the reactor temperature at 25° C. To the solution with TFMB added, 31.1 g (0.070 mol) of 6-FDA as an acid anhydride was added at the same temperature and stirred for 24 hours to obtain a polyimide precursor composition.

Comparative Example 3

A polyimide precursor composition was obtained according to the same process as in Example 1, except that the following control compound C, in which an aryl ring was not bonded to both amide rings, was used instead of the diamine compound 8.

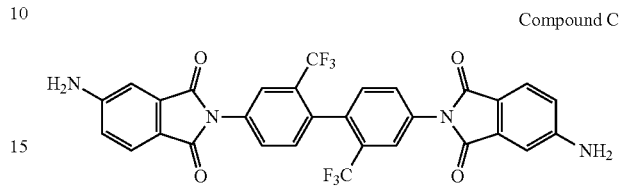

Compound C

Comparative Example 4

A polyimide precursor composition was obtained according to the same process as in Example 3, except that the following control compound C, in which an aryl ring was not bonded to both amide rings, was used instead of the diamine compound 8.

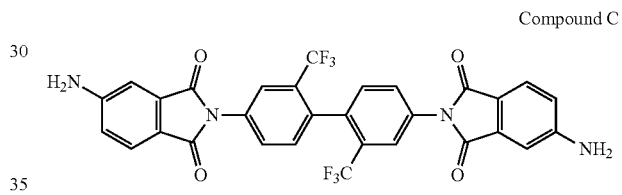

Compound C

The solid content and viscosity of each of the polyimide precursor compositions obtained in Examples 1 to 4 and Comparative Examples 1 to 4 are shown in Table 1 below.

Experimental Example 1

Each of the polyimide precursor compositions (solutions) prepared in Examples 1 to 4 and Comparative Examples 1 to 4 was spin coated on a glass substrate. The glass substrate coated with each polyimide precursor solution was placed in an oven, heated at a rate of 5° C./min and cured at 80° C. for 30 minutes and at 430° C. for 30 minutes to prepare each polyimide film.

<Evaluation of Properties of Polyimide Film>
1. Thermal Expansion Coefficient (CTE)

Each of the polyimides film obtained in Experimental Example 1 was cut to 5×20 mm to prepare a specimen, and then the specimen was loaded using an accessory of TMA (thermomechanical analyzer) (Q400, TA Instruments). A length of the film to be actually measured was equal to 16 mm. A pulling force of the film specimen was set at 0.02 N. The first temperature-rising step was carried out at a heating rate of 5° C./min from 100 to 350° C. and the cooling step was carried out at a cooling rate of 4° C./min from 350 to 100° C. The change in the thermal expansion was measured with TMA (Q400, TA Instruments).

2. Thermal Decomposition Temperature Using a thermogravimetric analyzer (TGA) (TGA 8000, PerkinElmer), the temperature (Td1%) when the weight loss of the polyimide film specimen was 1% in a nitrogen atmosphere was measured.

The measured CTE and Td1% values of the polyimide film are shown in Table 1 below.

TABLE 1

| Composition of Polyimide precursor solution | | Example 1 (BPDA-compound 8) | Example 2 (BPDA-compound 15) | Example 3 (6-FDA-compound 8) | Example 4 (6-FDA-compound 15) | Comp. Example 1 (BPDA-TFMB) | Comp. Example 2 (6-FDA-TFMB) | Comp. Example 3 (BPDA-Compound C) | Comp. Example 4 (6-FDA-Compound C) |
|---|---|---|---|---|---|---|---|---|---|
| Solid content (wt %) | | 11.68 | 18.75 | 12.59 | 10.23 | 10.33 | 16.5 | 22 | 29.97 |
| Viscosity (cP) | | 4500 | 4625 | 3692 | 3750 | 4200 | 3500 | 4500 | 462 |
| Curing condition (SiO₂ substrate) | | 430° C. (5° C./min) 30 min | 430° C. (5° C./min) 30 min | 430° C. (5° C./min) 30 min | 430° C. (5° C./min) 30 min | 430° C. (5° C./min) 30 min | 430° C. (5° C./min) 30 min | 430° C. (5° C./min) 30 min | 430° C. (5° C./min) 30 min |
| Film thickness (μm) | | 10.04 | 10.46 | 10.04 | 10.02 | 10.27 | 10.32 | 10.04 | 10.46 |
| Thermal Property | 1$^{st}$ heating CTE (ppm/° C.) | 5.55 | 5.28 | 29.09 | 20.11 | 42.44 | 54.17 | 10.55 | 46.67 |
| | Td1% (° C.) | 559 | 567 | 508 | 511 | 555 | 501 | 557 | 505 |

As can be seen from Table 1 above, polyimide films (Examples 1 to 4) prepared by using the polyimide precursor composition containing the novel diamine compound according to the present invention had a lower CTE value compared to the polyimide films of Comparative Examples 1 to 4 prepared by using a diamine compound having a different structure from the diamine compound of the present invention under the conditions of using the same acid anhydride. It indicates that the polyimide film according to the present invention has very little shrinkage behavior or change due to heating, from which it can be seen that the polyimide film according to the present invention has excellent heat resistance.

While the present invention has been particularly shown and described with reference to specific embodiments thereof, it will be apparent to those skilled in the art that this specific description is merely a preferred embodiment and that the scope of the invention is not limited thereby. It is therefore intended that the scope of the invention be defined by the claims appended hereto and their equivalents.

What is claimed is:

1. A diamine compound represented by the following formula 1:

[Formula 1]

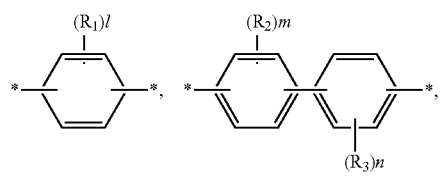

In the formula 1,
L is a linker selected from

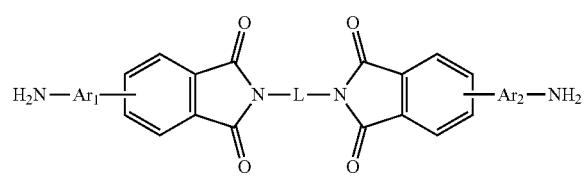

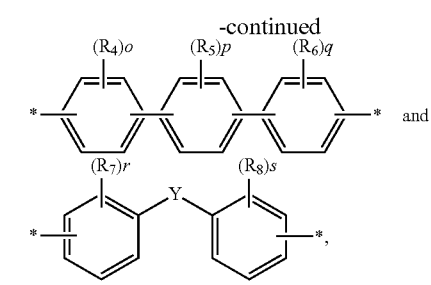

$Ar_1$ and $Ar_2$ are each independently a divalent organic group selected from

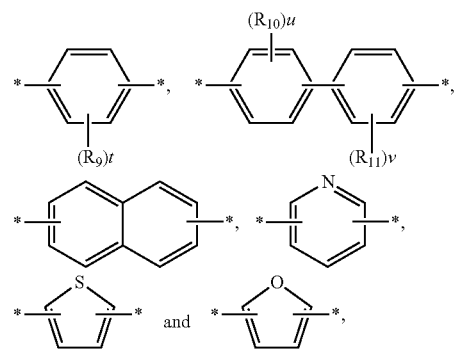

$R_1$ to $R_{11}$ are each independently hydrogen, deuterium, a halogen atom, a cyano group, a hydroxy group, a substituted or unsubstituted alkyl group having 1 to 30 carbon atoms, a substituted or unsubstituted haloalkyl group having 1 to 30 carbon atoms, a substituted or unsubstituted alkylsilyl group having 1 to 30 carbon atoms, a substituted or unsubstituted arylsilyl group having 6 to 30 carbon atoms, a substituted or unsubstituted alkylamino group having 1 to 30 carbon atoms, a substituted or unsubstituted arylamino group having 6 to 30 carbon atoms, a substituted or unsubstituted alkoxy group having 1 to 30 carbon atoms, a substituted or unsubstituted alkylthio group having 1 to 30 carbon atoms, a substituted or unsubstituted arylthiol group having 6 to 30 carbon atoms, a substituted or unsubstituted aryl group having 6 to 30 carbon atoms, a substituted or unsubstituted aralkyl group having 6 to 30 carbon atoms, a substituted or unsubstituted aryloxy group having 6 to 30 carbon atoms, a —COOH group, a substituted or unsubstituted cycloalkyl group having 3 to 30 carbon atoms, an amide group, a substituted or unsubstituted cycloalkyloxy group having 3 to 30 carbon atoms, a substituted or unsubstituted cycloalkylthio group having 1 to 30 carbon atoms, an ester group, —$CD_3$, an azide group, a nitro group, or a substituted or unsubstituted (3-30 membered) heteroaryl group comprising at least one selected from B, N, O, S, P (=O), Si and P, Y is selected from

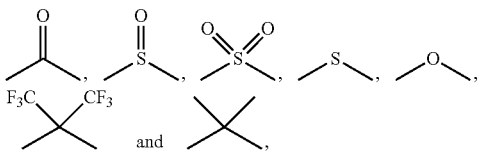

and l, m, n, o, p, q, r, s, t, u and v are each an integer of 0 to 4, and when l, m, n, o, p, q, r, s, t, u and v are integers of 2 to 4, each of $R_1$ to $R_{11}$ is the same or different.

2. The diamine compound according to claim 1, wherein L in the formula 1 is a linker selected from—

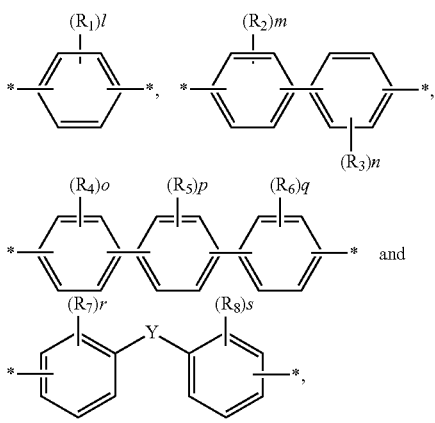

$Ar_1$ and $Ar_2$ are each independently

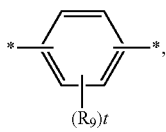

$R_1$ to $R_8$ are each independently a halogen atom, or an alkyl group having 1 to 6 carbon atoms or an alkoxy group having 1 to 6 carbon atoms, which are unsubstituted or substituted with a halogen atom, $R_9$ is a halogen atom, or an alkyl group having 1 to 6 carbon atoms which is unsubstituted or substituted with a halogen atom, Y is selected from and

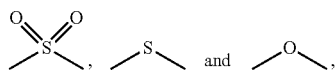

l, m, n, o, p, q, r, s and t are each an integer of 0 to 2.

3. The diamine compound according to claim 1, wherein L in the formula 1 is phenyl which is unsubstituted or substituted with one or more substituents selected from the group consisting of trifluoromethyl, methyl, chlorine (Cl) and methoxy; biphenyl which is unsubstituted or substituted with one or more substituents selected from the group consisting of methyl, trifluoromethyl and chlorine (Cl); terphenyl which is unsubstituted or substituted with trifluoromethyl; bis(trifluoromethylphenyl)sulfone, bis(methylphenyl)sulfone, {(trifluoromethylphenyl)sulfonyl}phenyl, diphenylsulfide, bis(methylphenyl)sulfide, bis(trifluoromethylphenyl)sulfide or diphenyl ether, $Ar_1$ and $Ar_2$ are each independently phenyl which is unsubstituted or substituted with one or more substituents selected from the group consisting of methyl, trifluoromethyl and chlorine (Cl), l is an integer of 0 to 2, and m, n, o, p, q, r, s and t are each an integer of 0 or 1.

4. The diamine compound according to claim 1, wherein the diamine compound of formula 1 is selected from compounds of the following structural formulae 1 to 21:

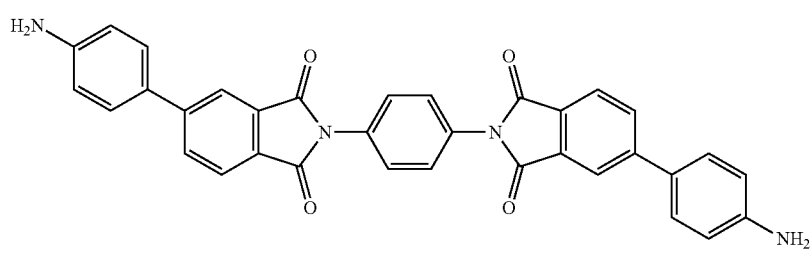
1
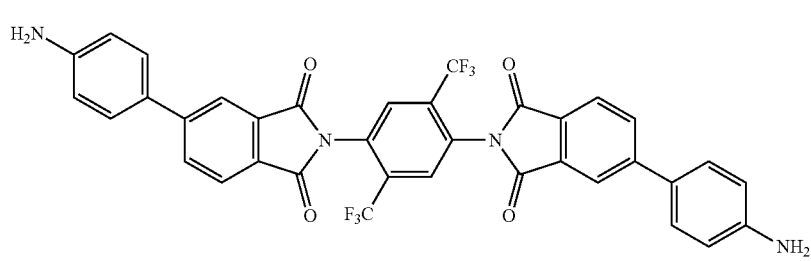
2
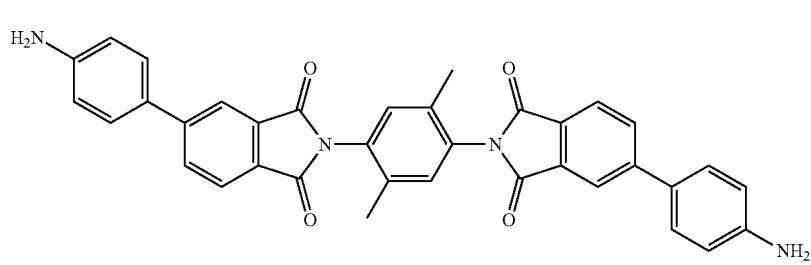
3
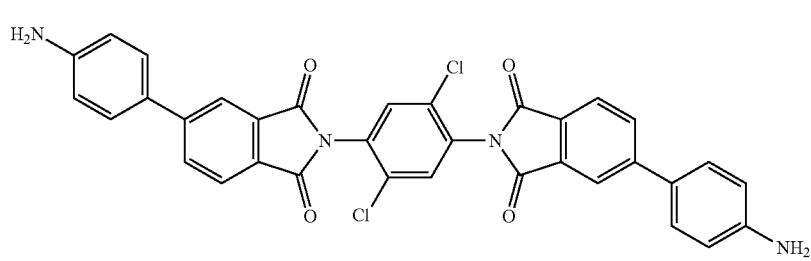
4
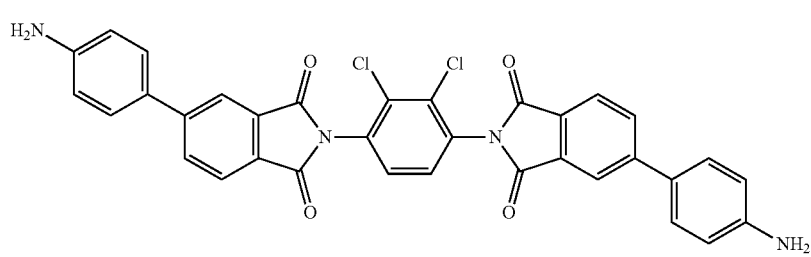
5
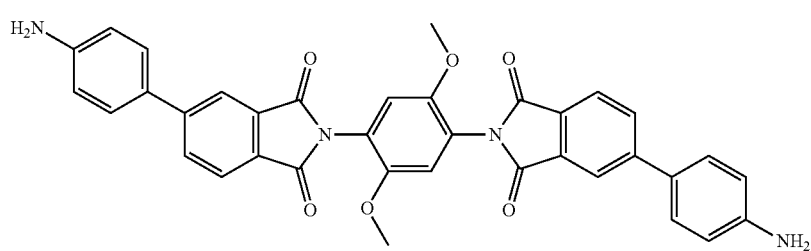
6

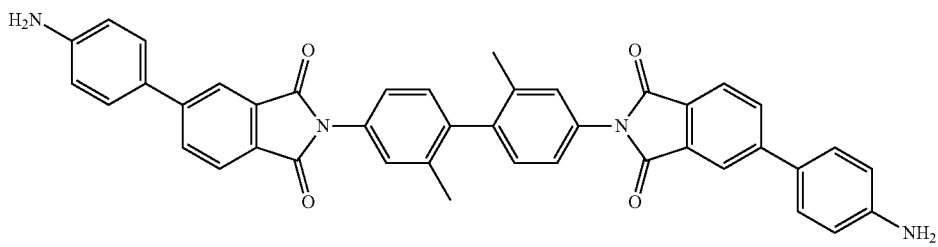
7
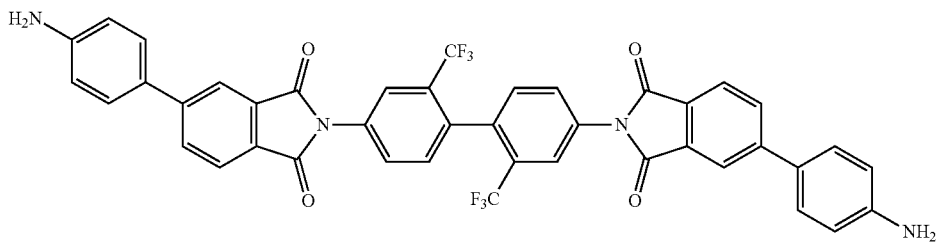
8
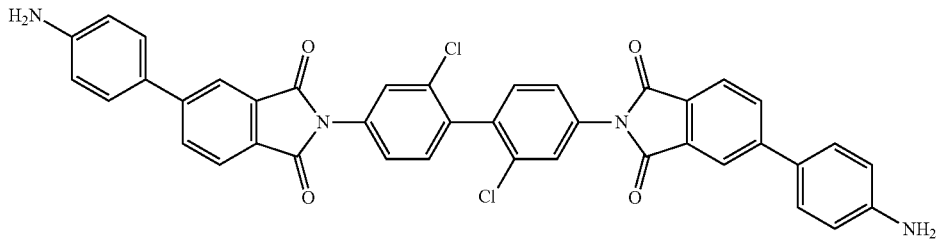
9
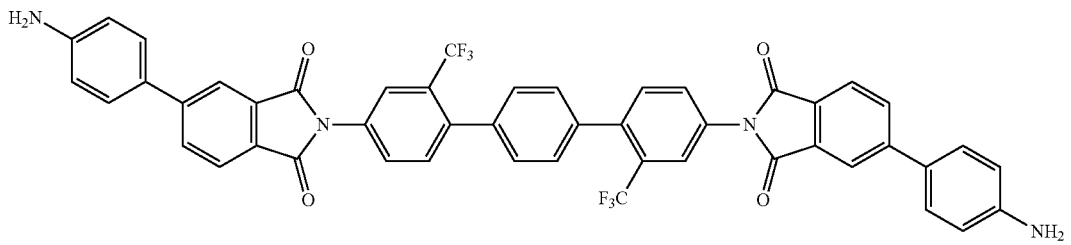
10
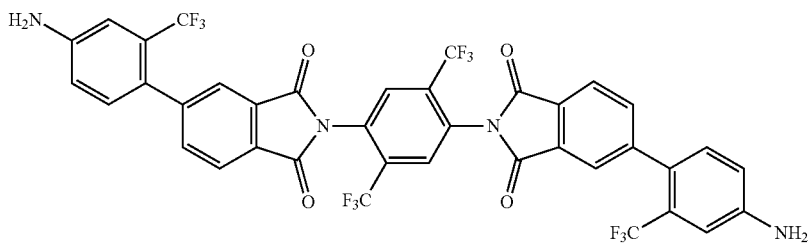
11
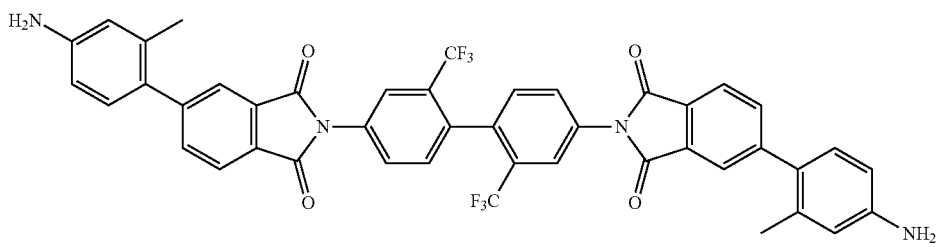
12

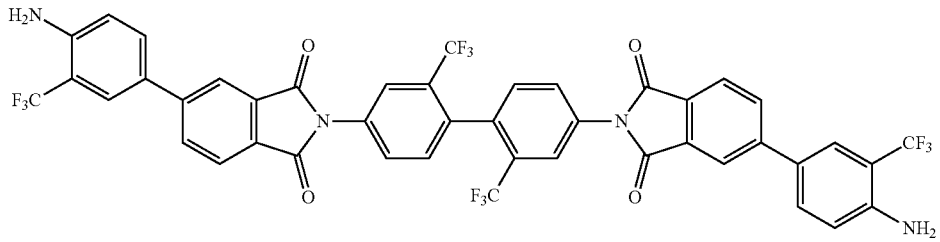
13
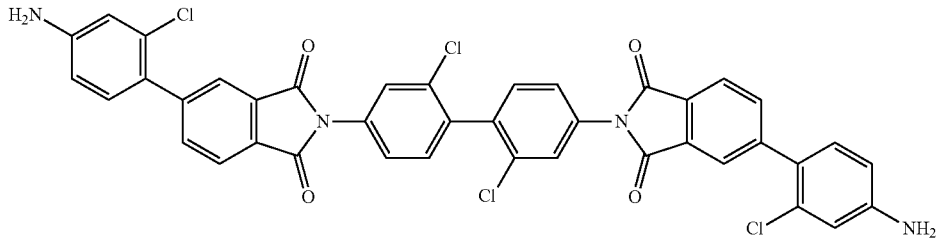
12
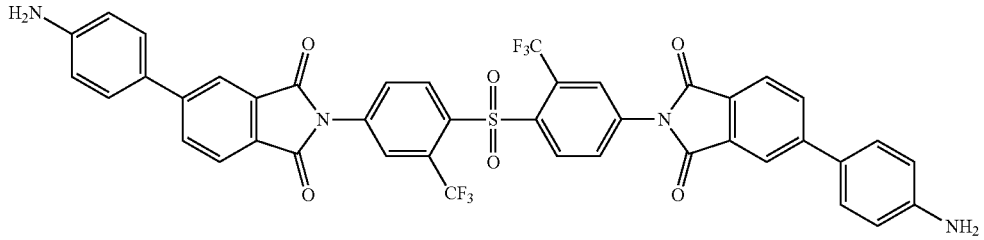
15
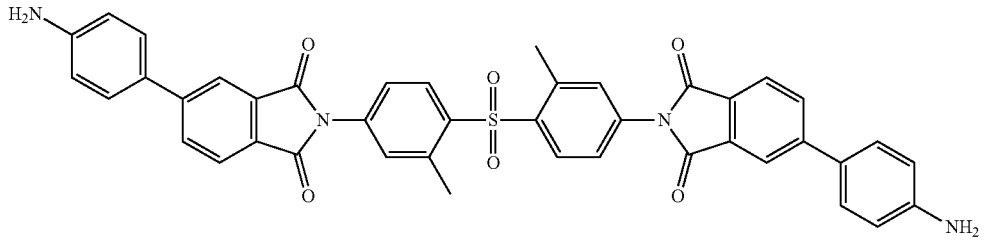
16
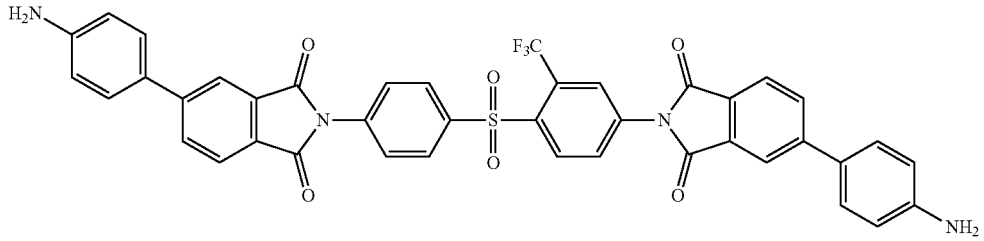
17
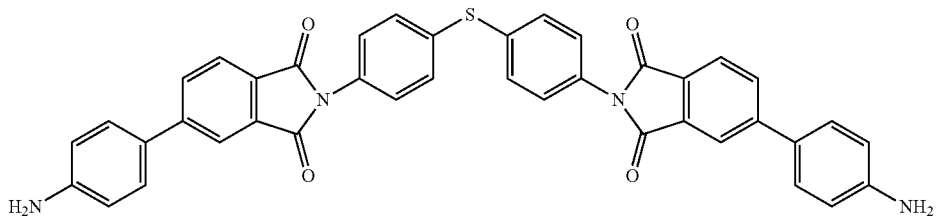
18

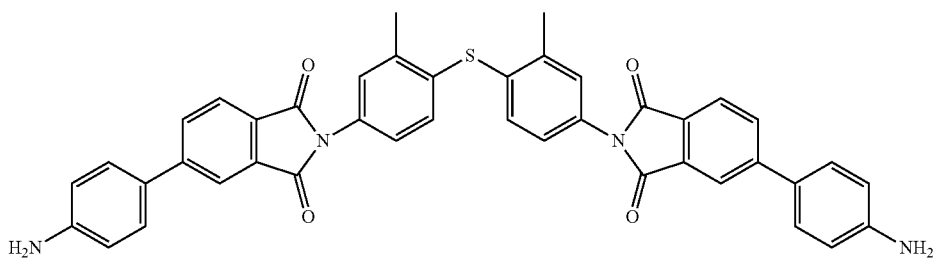

19

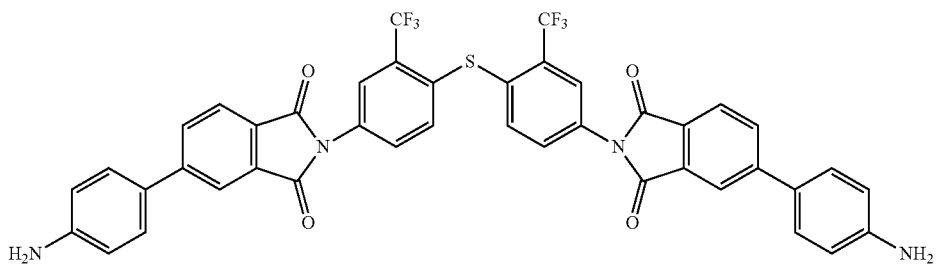

20

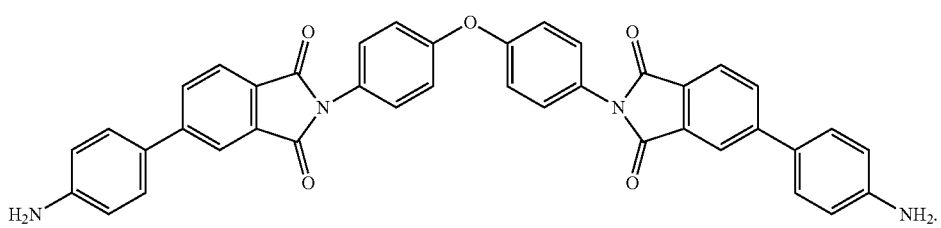

21

5. A polyimide precursor comprising a polymerized product of a composition comprising the diamine compound of formula 1 according to claim 1 and at least one acid dianhydride.

6. The polyimide precursor according to claim 5, wherein the acid anhydride comprises BPDA (biphenyl-tetracarboxylic acid dianhydride), 6-FDA (4,4'-(hexafluoroisopropylidene)diphthalic anhydride) or a mixture thereof.

7. A polyimide film formed from the polyimide precursor according to claim 5.

8. A flexible device including the polyimide film according to claim 7 as a substrate.

9. A polyimide precursor comprising a polymerized product of a composition comprising the diamine compound of formula 1 according to claim 2 and at least one acid dianhydride.

10. A polyimide precursor comprising a polymerized product of a composition comprising the diamine compound of formula 1 according to claim 3 and at least one acid dianhydride.

11. A polyimide precursor comprising a polymerized product of a composition comprising the diamine compound of formula 1 according to claim 4 and at least one acid dianhydride.

12. The polyimide precursor according to claim 9, wherein the acid anhydride comprises BPDA (biphenyl-tetracarboxylic acid dianhydride), 6-FDA (4,4'-(hexafluoroisopropylidene)diphthalic anhydride) or a mixture thereof.

13. The polyimide precursor according to claim 10, wherein the acid anhydride comprises BPDA (biphenyl-tetracarboxylic acid dianhydride), 6-FDA (4,4'-(hexafluoroisopropylidene)diphthalic anhydride) or a mixture thereof.

14. The polyimide precursor according to claim 11, wherein the acid anhydride comprises BPDA (biphenyl-tetracarboxylic acid dianhydride), 6-FDA (4,4'-(hexafluoroisopropylidene)diphthalic anhydride) or a mixture thereof.

15. A polyimide film formed from the polyimide precursor according to claim 9.

16. A polyimide film formed from the polyimide precursor according to claim 10.

17. A polyimide film formed from the polyimide precursor according to claim 11.

18. A flexible device including the polyimide film according to claim 15 as a substrate.

19. A flexible device including the polyimide film according to claim 16 as a substrate.

20. A flexible device including the polyimide film according to claim 17 as a substrate.

* * * * *